12 United States Patent
Ban et al.

(10) Patent No.: US 12,383,608 B2
(45) Date of Patent: Aug. 12, 2025

(54) WT1 HELPER PEPTIDES AND COMBINATIONS OF WT1 HELPER PEPTIDE AND CONJUGATE OF CANCER ANTIGEN PEPTIDES

(71) Applicants: Sumitomo Pharma Co., Ltd., Osaka (JP); INTERNATIONAL INSTITUTE OF CANCER IMMUNOLOGY, INC., Suita (JP)

(72) Inventors: Hitoshi Ban, Nishinomiya (JP); Masashi Goto, Ibaraki (JP); Yosuke Takanashi, Osaka (JP)

(73) Assignees: SUMITOMO PHARMA CO., LTD., Osaka (JP); INTERNATIONAL INSTITUTE OF CANCER IMMUNOLOGY, INC., Suita (JP)

( * ) Notice: Subject to any disclaimer, the term of this patent is extended or adjusted under 35 U.S.C. 154(b) by 238 days.

(21) Appl. No.: 16/464,950

(22) PCT Filed: Nov. 29, 2017

(86) PCT No.: PCT/JP2017/042760
§ 371 (c)(1),
(2) Date: May 29, 2019

(87) PCT Pub. No.: WO2018/101309
PCT Pub. Date: Jun. 7, 2018

(65) Prior Publication Data
US 2020/0016255 A1  Jan. 16, 2020

(30) Foreign Application Priority Data
Nov. 30, 2016  (JP) .................. 2016-233042

(51) Int. Cl.
*A61K 39/00* (2006.01)
*A61P 35/00* (2006.01)

(52) U.S. Cl.
CPC ...... *A61K 39/001153* (2018.08); *A61K 39/00* (2013.01); *A61P 35/00* (2018.01)

(58) Field of Classification Search
None
See application file for complete search history.

(56) References Cited

U.S. PATENT DOCUMENTS

| | | |
|---|---|---|
| 7,030,212 B1 | 4/2006 | Sugiyama et al. |
| 7,326,767 B1 | 2/2008 | Stauss et al. |
| 7,390,871 B2 | 6/2008 | Sugiyama et al. |
| 7,517,950 B2 | 4/2009 | Sugiyama et al. |
| 7,547,439 B1 | 6/2009 | Huang et al. |
| 7,608,685 B1 | 10/2009 | Sugiyama et al. |
| 7,807,792 B2 | 10/2010 | Sugiyama et al. |
| 7,939,627 B2 | 5/2011 | Nishihara et al. |
| 8,105,604 B2 | 1/2012 | Sugiyama |
| 8,575,308 B2 | 11/2013 | Nishihara et al. |
| 8,765,687 B2 | 7/2014 | Scheinberg et al. |
| 9,181,302 B2 | 11/2015 | Li et al. |
| 9,233,149 B2 | 1/2016 | Scheinberg et al. |
| 9,248,173 B2 | 2/2016 | Li et al. |
| 9,266,932 B2 | 2/2016 | Sugiyama |
| 9,273,148 B2 | 3/2016 | Nishihara et al. |
| 9,403,886 B2 | 8/2016 | Sugiyama et al. |
| 9,765,114 B2 | 9/2017 | Nishihara et al. |
| 10,124,046 B2 | 11/2018 | Sugiyama |
| 10,221,224 B2 | 3/2019 | Scheinberg et al. |
| 10,426,822 B2 | 10/2019 | Sugiyama |
| 10,588,952 B2 | 3/2020 | Ban |
| 2004/0097703 A1 | 5/2004 | Sugiyama |
| 2005/0050580 A1 | 3/2005 | Gotoh |
| 2005/0266014 A1 | 12/2005 | Sugiyama et al. |
| 2006/0093615 A1 | 5/2006 | Sugiyama et al. |
| 2006/0107339 A1 | 5/2006 | Gotoh |
| 2006/0217297 A1 | 9/2006 | Sugiyama |
| 2007/0082860 A1 | 4/2007 | Sugiyama |
| 2008/0014636 A1 | 1/2008 | Sato et al. |
| 2008/0050340 A1 | 2/2008 | Kedl et al. |
| 2008/0070835 A1 | 3/2008 | Sugiyama |
| 2008/0159993 A1 | 7/2008 | Stauss et al. |
| 2009/0143291 A1 | 6/2009 | Sugiyama et al. |
| 2009/0281043 A1 | 11/2009 | Sugiyama et al. |
| 2009/0325886 A1 | 12/2009 | Sugiyama |
| 2010/0062010 A1 | 3/2010 | Nishihara et al. |
| 2010/0111986 A1* | 5/2010 | Scheinberg .... A61K 39/001153 424/185.1 |

(Continued)

FOREIGN PATENT DOCUMENTS

| | | |
|---|---|---|
| CA | 2757764 | 10/2010 |
| CA | 2 846 479 A1 | 3/2013 |

(Continued)

OTHER PUBLICATIONS

International Preliminary Report on Patentability and Written Opinion issued on Jun. 13, 2019 in PCT/JP2017/042760, 10 pages.
International Search Report issued on Jan. 16, 2018 in PCT/JP2017/042760, 2 pages.
Zeng, G., "Mhc Class II-Restricted Tumor Antigens Recognized by CD4+Cells: New Strategies for Cancer Vaccine Design", Journal of Immunotherapy, vol. 24, No. 3, 2001, pp. 195-204.
Extended European Search Report issued Jul. 8, 2020 in corresponding European Patent Application No. 17875568.2 9 pages.
U.S Office Action issued in U.S. Appl. No. 15/575,162 on Jan. 21, 2022.
Gaiger et al., Blood 96(4), 1480-1489, 2000.
Mailander et al., Leukemia 18, 165-166, 2004.

(Continued)

*Primary Examiner* — Julie Ha
*Assistant Examiner* — Tara L Martinez
(74) *Attorney, Agent, or Firm* — Oblon, McClelland, Maier & Neustadt, L.L.P.

(57) ABSTRACT

The present application relates to WT1 helper peptides consisting of an amino acid sequence of 9 to 30 amino acid residues including a sequence: KLSHL as part thereof, and combinations of a WT1 helper peptide and a conjugate of cancer antigen peptides.

27 Claims, 10 Drawing Sheets

Specification includes a Sequence Listing.

(56) References Cited

U.S. PATENT DOCUMENTS

| | | |
|---|---|---|
| 2010/0255579 A1 | 10/2010 | Sato et al. |
| 2010/0292164 A1 | 11/2010 | Sugiyama et al. |
| 2010/0317111 A1 | 12/2010 | Kedl et al. |
| 2011/0033449 A1 | 2/2011 | Glennie et al. |
| 2011/0070251 A1 | 3/2011 | Sugiyama |
| 2011/0098233 A1 | 4/2011 | Sugiyama |
| 2011/0229506 A1 | 9/2011 | Nishihara et al. |
| 2011/0274685 A1 | 11/2011 | Keler et al. |
| 2011/0286968 A1 | 11/2011 | Kedl et al. |
| 2012/0045465 A1 | 2/2012 | Sugiyama |
| 2012/0095045 A1 | 4/2012 | Yeo |
| 2012/0213771 A1 | 8/2012 | Keler et al. |
| 2012/0237569 A1 | 9/2012 | Saito et al. |
| 2012/0251494 A1 | 10/2012 | Kedl et al. |
| 2012/0301492 A1 | 11/2012 | Gaiger et al. |
| 2013/0243800 A1 | 9/2013 | Sugiyama |
| 2013/0266958 A1 | 10/2013 | Sugiyama et al. |
| 2013/0336976 A1 | 12/2013 | Glennie et al. |
| 2014/0046036 A1 | 2/2014 | Nishihara et al. |
| 2014/0134200 A1 | 5/2014 | Sugiyama et al. |
| 2014/0220054 A1 | 8/2014 | Scheinberg et al. |
| 2014/0220059 A1 | 8/2014 | Asari et al. |
| 2015/0080321 A1 | 3/2015 | Li et al. |
| 2015/0150975 A1 | 6/2015 | Tanaka |
| 2015/0238587 A1 | 8/2015 | Li et al. |
| 2015/0337047 A1 | 11/2015 | Keler et al. |
| 2015/0376253 A1 | 12/2015 | Kedl et al. |
| 2016/0045551 A1 | 2/2016 | Brentjens et al. |
| 2016/0114019 A1 | 4/2016 | Li et al. |
| 2016/0168197 A1 | 6/2016 | Nishihara et al. |
| 2016/0176939 A1 | 6/2016 | Sugiyama |
| 2016/0199472 A1 | 7/2016 | Sugiyama |
| 2016/0243209 A1 | 8/2016 | Sugiyama et al. |
| 2016/0264638 A1 | 9/2016 | Scheinberg et al. |
| 2018/0140691 A1 | 5/2018 | Takasu et al. |
| 2018/0170986 A1 | 6/2018 | Sugiyama |
| 2018/0207254 A1 | 7/2018 | Sugiyama |
| 2019/0030149 A1 | 1/2019 | Li et al. |

FOREIGN PATENT DOCUMENTS

| | | |
|---|---|---|
| CN | 103157108 A | 6/2013 |
| CN | 103830211 A | 6/2014 |
| EP | 1103564 A1 | 5/2001 |
| EP | 1 584 627 A1 | 10/2005 |
| EP | 1 961 761 A1 | 8/2008 |
| EP | 2 341 142 A2 | 7/2011 |
| EP | 2 626 418 A1 | 8/2013 |
| EP | 243310 B1 | 12/2014 |
| EP | 2423310 B1 | 12/2014 |
| EP | 3 604 325 A1 | 2/2020 |
| JP | 11-504635 A | 4/1999 |
| JP | 2002-525099 | 8/2002 |
| JP | 2006-521378 A | 9/2006 |
| JP | 2006-280324 A | 10/2006 |
| JP | 2006-525995 A | 11/2006 |
| JP | 2007-507543 A | 3/2007 |
| JP | WO2005-045027 * | 5/2007 |
| JP | 2006-512391 A | 4/2008 |
| JP | 2009-23993 A | 2/2009 |
| JP | 2009-513532 A | 4/2009 |
| JP | 2012-522513 A | 9/2012 |
| JP | 2012-530697 | 12/2012 |
| JP | 2013-531970 A | 8/2013 |
| JP | 2014-27935 A | 2/2014 |
| JP | 2014-169282 A | 9/2014 |
| JP | 2014-221795 A | 11/2014 |
| JP | 2015-501839 A | 1/2015 |
| WO | WO 96/34888 A1 | 11/1996 |
| WO | WO 97/26784 | 7/1997 |
| WO | WO 00/06602 | 2/2000 |
| WO | WO 00/06602 A1 | 2/2000 |
| WO | WO 00/18795 | 4/2000 |
| WO | WO 02/47474 A1 | 6/2002 |
| WO | WO 02/079253 A1 | 10/2002 |
| WO | WO 2004/029248 A1 | 4/2004 |
| WO | WO 2004/060319 A2 | 7/2004 |
| WO | WO 2004/63217 A1 | 7/2004 |
| WO | WO 2004/093831 A2 | 11/2004 |
| WO | WO 2004/093871 A1 | 11/2004 |
| WO | WO 2004/113530 A | 12/2004 |
| WO | WO 2005/004907 A1 | 1/2005 |
| WO | WO 2005/037995 A2 | 4/2005 |
| WO | WO 2005/045027 | 5/2005 |
| WO | WO 2005/045027 A1 | 5/2005 |
| WO | WO 2007/047764 | 4/2007 |
| WO | WO 2007/047764 A2 | 4/2007 |
| WO | WO 2007/063903 | 6/2007 |
| WO | WO 2007/063903 A1 | 6/2007 |
| WO | WO 2007/120673 | 10/2007 |
| WO | WO 2007/130493 A2 | 11/2007 |
| WO | WO 2008/051424 A2 | 5/2008 |
| WO | WO 2008/081701 A1 | 7/2008 |
| WO | WO 2009/036246 | 3/2009 |
| WO | WO 2009/072610 A1 | 6/2009 |
| WO | WO 2010/063011 A2 | 3/2010 |
| WO | WO 2010/037395 A2 | 4/2010 |
| WO | WO 2010/123065 A1 | 10/2010 |
| WO | WO 2011/110953 A2 | 9/2011 |
| WO | WO 2011/130434 A2 | 10/2011 |
| WO | WO 2012/026309 A1 | 3/2012 |
| WO | WO 2013/090293 A1 | 6/2013 |
| WO | WO 2013/132044 A1 | 9/2013 |
| WO | WO 2014/134165 A1 | 9/2014 |
| WO | WO 2014/157692 A1 | 10/2014 |
| WO | WO 2015/019284 A2 | 2/2015 |
| WO | WO 2016/186177 A1 | 11/2016 |

OTHER PUBLICATIONS

Janeway et al., Immunobiology 1997 4$^{th}$ Edition Garland Press 1999, pp. 121, 551 and 569 and Figures 4.3, 4.5 and 4.7
Srivastava, Nature Immun. 1(5), 363-366, 2000.
Gaiger et al., Clin. Cancer Clin. Cancer Res. 7, 761s-765s, 2001.
Guidance for Industry—Preclinical Assessment of Investigational Cellular and Gene Therapy Products, U.S. Department of Health and Human Services Food and Drug Administration Cancer for Biologics Evaluation and research, Nov. 2013, 35 pages.
Keilholz, Leukemia (2004) 18, 165-166.
Oka et al., National Acad. Sci (2004), 101,13885-13890.
Kakugawa et al., Efficient Induction of Peptide-specific Cytotoxic T Lymphocytes by LPS-Activated Spleen Cells, Microbiol. Immunol., vol. 44(2), pp. 123-133, 2000.
Title page and pp. 551-554 of Janeway et al., Immunobiology, 1997 4th Edition Garland Press, 1999.
Interference No. 105987—Sugiyama Motion 1 (Mar. 26, 2014).
Interference No. 105987—Stauss Motion 1 (May 15, 2014).
Interference No. 105987—Stauss Motion 2 (May 15, 2014).
Interference No. 105987—Stauss Motion 3 (May 15, 2014).
Interference No. 105987—Sugiyama Substantive Motion 1 (May 15, 2014).
Interference No. 105987—Sugiyama Responsive Motion 2 (Jun. 5, 2014).
Interference No. 105987—Stauss Opposition 1 (Jul. 17, 2014).
Interference No. 105987—Stauss Opposition 2 (Jul. 17, 2014).
Interference No. 105987—Sugiyama Opposition to Stauss Motion 1 (Jul. 17, 2014).
Interference No. 105987—Sugiyama Opposition to Stauss Motion 2 (Jul. 17, 2014).
Interference No. 105987—Sugiyama Opposition to Stauss Motion 3 (Jul. 17, 2014).
Interference No. 105987—Sugiyama Reply 1 (Aug. 28, 2014).
Interference No. 105987—Sugiyama Reply 2 (Aug. 28, 2014).
Interference No. 105987—Stauss Reply 1 (Aug. 28, 2014).
Interference No. 105987—Stauss Reply 2 (Aug. 28, 2014).
Interference No. 105987—Stauss Reply 3 (Aug. 28, 2014).
Interference No. 105987—Sugiyama Miscellaneous Motion (Oct. 9, 2014).
Interference No. 105987—Stauss Opposition 3 (Oct. 30, 2014).

(56) References Cited

OTHER PUBLICATIONS

Interference No. 105987—Sugiyama Reply 3 (to Stauss Oppsition to Sugiyama Misc. Motion 1) (Nov. 20, 2014).
Yoshihiro Oka, et al., "Cancer Immunotherapy Targeting Wilms' Tumor Gene WT1 Product", The Journal of Immunology, 164(4), 2000, 1873-1880.
Ann Van Driessche, et al., "Active Specific Immunotherapy Targeting the Wilms' Tumor Protein 1 (WT1) for Patients with Hematological Malignancies and Solid Tumors: Lessons from Early Clinical Trials", The Oncologist, 17(2), 2012, pp. 250-259.
Peter G. Maslak, et al., "Vaccination with synthetic analog peptides derived from WT1 oncoprotein induces T-cell responses in patients with complete remission from acute myeloid leukemia", Clinical Trials and Observations, Blood, 116(2), 2010, pp. 171-179.
Paul H. Naylor, et al., "Peptide Based Vaccine Approaches for Cancer—A Novel Approach Using a WT-1 Synthetic Long Peptide and the IRX-2 Immunomodulatory Regimen", Cancers, 3, 2011, pp. 3991-4009.
Norihiko Takahashi, et al., "First clinical trial of cancer vaccine therapy with artificially synthesized helper/killer-hybrid epitope long peptide of MAGE-A4 cancer antigen", Cancer Science, 103, 2012, pp. 150-153.
Anthony W. Purcell, et al., "More than one reason to rethink the use of peptides in vaccine design", Nature Reviews Drug Discovery, 6(5), 2007, pp. 404-414.
Katherine M. Call, "Isolation and Characterization of a Zinc Finger Polypeptide Gene at the Human Chromosone 11 Wilms' Tumor Locus", Cell, 60(3), 1990, pp. 509-520.
Akihiro Tsuboi, et al., "Cytotoxic T-Lymphocyte Responses Elicited to Wilms' Tumor Gene WT1 Product by DNA Vaccination", Journal of Clinical Immunology, 20(3), 2000, pp. 195-202.
Kenneth L. Rock, et al., "Post-proteasomal antigen processing for major histocompatibility complex class I presentation", Nature Immunology, 5(7), 2004, pp. 670-677.
Sonia A. Perez, et al., "A New Era in Anticancer Peptide Vaccines", Cancer, 116(9), 2010, pp. 2071-2080.
Lee M. Krug, et al., "WT1 peptide vaccinations induce CD4 and CD8 T cell immune responses in patients with mesothelioma and non-small cell lung cancer", Cancer Immunol Immunother, 59, 2010, pp. 1467-1479.
Grazyna Kochan, et al., "Crystal structures of the endoplasmic reticulum aminopeptidase-1 (ERAP1) reveal the molecular basis for N-terminal peptide trimming", Proceedings of the National Academy of Science of United States of America, 108(19), 2011, pp. 7745-7750.
Tomo Saric, et al., "An IFN-Y-induced aminopeptidase in the ER, ERAP I, trims precursors to MHC class I-presented peptides", Nature Immunology, 3(12), 2002, pp. 1169-1176.
Ian A. York, et al., "The ER aminopeptidase ERAP I enhances or limits antigen presentation by trimming epitopes to 8-9 residues", Nature Immunology, 3(12), 2002, pp. 1177-1184.
Efthalia Zervoudi, et al., "Probing the S1 specificity pocket of the aminopeptidases that generate antigenic peptides", Biochemical Journal, 435, 2011, pp. 411-420.
Interference No. 105987—Decision on Motions BD.R. 125(a) (Feb. 20, 2015).
Interference No. 105987—Exhibit 1001—Amendment for entry in Sugiyama U.S. Appl. No. 12/181,938.
Interference No. 105987—Exhibit 1002—U.S. Pat. No. 7,030,212 B1, issued Apr. 18, 2006.
Interference No. 105987—Exhibit 1003—Terminal Disclaimer filed and approved in Sugiyama U.S. Appl. No. 12/181,938 on Dec. 4, 2013.
Interference No. 105987—Exhibit 1004—Original specification of Sugiyama U.S. Appl. No. 12/181,938, filed Jul. 29. 2008.
Interference No. 105987—Exhibit 1005—Original specification of U.S. Appl. No. 11/196,452, filed Aug. 4, 2005, issued as U.S. Pat. No. 7,608.685.
Interference No. 105987—Exhibit 1006—Copy of the original specification of U.S. Appl. No. 09/744,815, filed Jan. 30, 2001, issued as U.S. Pat. No. 7,030,212.
Interference No. 105987—Exhibit 1007—WO 00/06602 which is a publication of International Application PCT/JP99/04130, filed Jul. 30, 1999.
Interference No. 105987—Exhibit 1008—Original and the certified translation of Japanese Application JP 10-218093, filed Jul. 31, 1998.
Interference No. 105987—Exhibit 1009—USPTO Communication mailed Jan. 9, 2014, in Sugiyama application U.S. Appl. No. 12/181,938.
Interference No. 105987—Exhibit 1010—U.S. Pat. No. 7,326,767 B1, issued Feb. 5, 2008.
Interference No. 105987—Exhibit 1011—U.S. Pat. No. 8,529,904 B2, issued Sep. 10, 2013.
Interference No. 105987—Exhibit 1012—Certified UK 9823897.5, filed Nov. 2, 1998, which was filed in the USPTO Apr. 12, 2002.
Interference No. 105987—Exhibit 1013—Sugiyama U.S. Appl. No. 12/181,938, published as U.S. 2009/0143291 A1.
Interference No. 105987—Exhibit 1014—PCT/GB99/03572, filed on Nov. 2, 1999, published as WO 00/26249 on May 11, 2000.
Interference No. 105987—Exhibit 1015—Non-Final Office Action mailed May 5, 2003, in Stauss U.S. Appl. No. 09/625,963.
Interference No. 105987—Exhibit 1016—Non-Final Office Action mailed Jan. 30, 2004, in Stauss U.S. Appl. No. 09/625,963.
Interference No. 105987—Exhibit 1017—Stauss Response filed Apr. 26, 2013, in Stauss U.S. Appl. No. 11/825,578.
Interference No. 105987—Exhibit 1018—Stauss Response filed Nov. 5, 2003, in Stauss U.S. Appl. No. 09/625,963.
Interference No. 105987—Exhibit 1019—Oka et al., J. Immunol. 164(4): 1873-1880, 2000.
Interference No. 105987—Exhibit 1020—Stauss Response filed Jul. 30, 2004, in Stauss U.S. Appl. No. 09/625,963.
Interference No. 105987—Exhibit 1021—Gaiger et al., Blood 96(4): 1480-1489, 2000.
Interference No. 105987—Exhibit 1022—Mailander et al., Leukemia 18: 165-166, 2004.
Interference No. 105987—Exhibit 1023—Non-Final Office Action mailed Apr. 29, 2010, in Stauss U.S. Appl. No. 11/825,578.
Interference No. 105987—Exhibit 1024—Final Office Action mailed Oct. 26, 2010, in Stauss U.S. Appl. No. 11/825,578.
Interference No. 105987—Exhibit 1025—Janeway et al., Immunobiology, 1997 4th Edition Garland Press 1999 pp. 121, 551 and 569 and Figures 4.3, 4.5 and 4.7.
Interference No. 105987—Exhibit 1026—Srivastava, P., Nature Immunology 1(5): 363-366, 2000.
Interference No. 105987—Exhibit 1027—Gaiger et al., Clin. Cancer Res. 7: 761s-765s, 2001.
Interference No. 105987—Exhibit 1028—Guidance for Industry—Preclinical Assessment of Investigational Cellular and Gene Therapy Products, U.S. Department of Health and Human Services Food and Drug Administration Center for Biologics Evaluation and Research, Nov. 2013.
Interference No. 105987—Exhibit 1029—U.S. Pat. No. 7,063,854.
Interference No. 105987—Exhibit 1031—Amendment for entry in Sugiyama U.S. Appl. No. 12/181,938.
Interference No. 105987—Exhibit 1032—Terminal Disclaimer over U.S. Pat. No. 7,030,212 filed on Feb. 4, 2010 in U.S. Appl. No. 12/366,200.
Interference No. 105987—Exhibit 1033—USPTO notice of Mar. 10, 2010, showing the approval of the Terminal Disclaimer filed on Feb. 4, 2010.
Interference No. 105987—Exhibit 1034—Amendment filed Sep. 17, 2004, in U.S. Appl. No. 09/744,815.
Interference No. 105987—Exhibit 1036—U.S. Patent Application Publication US 2008/0159993, published Jul. 3, 2008.
Interference No. 105987—Exhibit 1038—Response to Formalities Letter and Preliminary Amendment filed Mar. 31, 2014 in Stauss U.S. Appl. No. 13/966,454.
Interference No. 105987—Exhibit 1039—Chart comparing Sugiyama current claims with pre-critical date claims in Sugiyama U.S. Appl. No. 09/744,815 and U.S. Appl. No. 09/744,815.

(56) References Cited

OTHER PUBLICATIONS

Interference No. 105987—Exhibit 1040—Preliminary Amendment filed on Jul. 29, 2008, in Sugiyama U.S. Appl. No. 12/181,938.
Interference No. 105987—Exhibit 1041—Preliminary Amendment filed on Feb. 2, 2009, in Sugiyama U.S. Appl. No. 12/181,938.
Interference No. 105987—Exhibit 1042—Preliminary Amendment filed on Aug. 4, 2005, in U.S. Appl. No. 11/196,452.
Interference No. 105987—Exhibit 1043—Amendment filed on Mar. 20, 2008, in U.S. Appl. No. 11/196,452.
Interference No. 105987—Exhibit 1044—Preliminary Amendment filed on Jan. 30, 2001, in U.S. Appl. No. 09/744,815.
Interference No. 105987—Exhibit 1045—Amendment filed on Aug. 1, 2005, in U.S. Appl. No. 09/744,815.
Interference No. 105987—Exhibit 1046—Amendment filed on Jun. 29, 2011, in Sugiyama U.S. Appl. No. 12/181,938.
Interference No. 105987—Exhibit 1047—Office Action mailed Dec. 29, 2010, in Sugiyama U.S. Appl. No. 12/181,938.
Interference No. 105987—Exhibit 1048—Amendment filed on Dec. 4, 2013, in Sugiyama U.S. Appl. No. 12/181,938.
Interference No. 105987—Exhibit 1049—Amendment filed on Nov. 9, 2012, in Sugiyama U.S. Appl. No. 12/181,938.
Interference No. 105987—Exhibit 1050—Deposition Transcript of Dr. Özlem Türeci taken Jun. 30, 2014.
Interference No. 105987—Exhibit 1051—Keilholz, Leukemia, (2004) 18, 165-166.
Interference No. 105987—Exhibit 1052—Oka et al, Proc. Natl. Acad. Sci., (2004) 101, 13885-13890.
Interference No. 105987—Exhibit 1053—Amendment filed Mar. 14, 2006, in Stauss U.S. Appl. No. 09/625,963.
Interference No. 105987—Exhibit 1054—Appeal Brief filed Nov. 22, 2006, in Stauss U.S. Appl. No. 09/625,963.
Interference No. 105987—Exhibit 1055—Amendment filed Aug. 27, 2010, in Stauss U.S. Appl. No. 11/825,578.
Interference No. 105987—Exhibit 1056—Claim Chart Showing Support for the Claimed Invention in the '938 Application.
Interference No. 105987—Exhibit 1057—Declaration for Utility or Design Patent Application filed on Jul. 6, 2007 during examination of the '904 patent.
Interference No. 105987—Exhibit 1058—Sugiyama's Objections to Stauss's Exhibits.
Interference No. 105987—Exhibit 2001—U.S. Pat. No. 7,326,767 (Stauss '767).
Interference No. 105987—Exhibit 2002—Sugiyama Preliminary Amendment dated Jul. 29, 2008 to U.S. Appl. No. 12/181,938, cancelling claims 1-7, adding new claims 8-19.
Interference No. 105987—Exhibit 2003—Sugiyama Preliminary Amendment dated Feb. 2, 2009 to U.S. Appl. No. 12/181,938, cancelling claims 1-19, adding new claims 20-23.
Interference No. 105987—Exhibit 2004—Sugiyama Preliminary Amendment dated Jul. 2, 2009 to U.S. Appl. No. 12/181,938, amending claims 21, 22, adding new claims 24-67.
Interference No. 105987—Exhibit 2005—Office Action dated Dec. 29, 2010 rejecting Sugiyama claims 20-24, and 27-28 as unpatentable under 35 USC § 112 and for nonstatutory double patenting over claims 1-5 of U.S. Pat. No. 7,030,212 and claims 1-5 of U.S. Pat. No. 7,608,685.
Interference No. 105987—Exhibit 2006—U.S. Pat. No. 7,608,685 (Sugiyama '685).
Interference No. 105987—Exhibit 2007—Sugiyama Amendment dated Jun. 29, 2011 amending the numeric range and size limitations of the amino acids in claims 20, and 21.
Interference No. 105987—Exhibit 2008—Final Office Action dated Oct. 7, 2011 rejecting Sugiyama claim 28 as unpatentable under 35 USC §112 and claims 20-24, and 27-28 as unpatentable for nonstatutory double patenting over claims 1-5 of U.S. Pat. No. 7,030,212 and claims 1-5 of U.S. Pat. No. 7,608,685.
Interference No. 105987—Exhibit 2009—Sugiyama Amendment dated Nov. 9, 2012 adding involved new claims 68-75.
Interference No. 105987—Exhibit 2010—Office Action dated Jul. 24, 2013 rejecting Sugiyama claims 20-24, 27-28, 72-73 as being unpatentable for nonstatutory obviousness-type double patenting over claims 1-5 of U.S. Pat. No. 7,030,212 and claims 1-5 of U.S. Pat. No. 7,608,685.
Interference No. 105987—Exhibit 2011—Sugiyama Amendment dated Dec. 4, 2013 amending limitations of claims 27- 28.
Interference No. 105987—Exhibit 2012—Application Data Sheet from file history of the '938 application filed on Jul. 29, 2008.
Interference No. 105987—Exhibit 2013—Declaration of Dr. Özlem Türeci.
Interference No. 105987—Exhibit 2014—Chart of Sugiyama's Pre-and Post-critical Date Claims.
Interference No. 105987—Exhibit 2015—Kakugawa et al "Efficient Induction of Peptide-specific Cytotoxic T Lymphocytes by LPS-Activated Spleen Cells", Microbiol. Immunnol., vol. 44(2), pp. 123-133, (2000).
Interference No. 105987—Exhibit 2016—Decision dated Jan. 17, 2014 of the Board of Patent Appeals of the European Patent Office rendered in Case No. T1457/09-3.3.04, entitled "Immunotherapeutic methods using epitopes of WT-1 and GATA-1", Patent Proprietor: Ganymed Pharmaceuticals AG and Opponent Dainippon Sumitomo Pharma Co., Ltd., issued Mar. 6, 2014.
Interference No. 105987—Exhibit 2017—Transcript of Deposition of Dr. Türeci taken on Jun. 30, 2014.
Interference No. 105987—Exhibit 2018—Supplemental Application Data Sheet filed Mar. 31, 2014 in Response to Formalities Letter and Preliminary Amendment to U.S. Appl. No. 13/966,454 (the '454 application).
Interference No. 105987—Exhibit 2019—Office Action dated Sep. 14, 2012 from the file history of involved Stauss U.S. Pat. No. 8,529,904.
Interference No. 105987—Exhibit 2020—Notice of Allowability dated May 6, 2013 from the file history of involved Stauss U.S. Pat. No. 8,529,904.
Interference No. 105987—Exhibit 2021—Office Action Response dated Apr. 26, 2013 from the file history of involved Stauss U.S. Pat. No. 8,529,904.
Interference No. 105987—Exhibit 2022—title page and pp. 551 to 554 of Janeway et al., Immunobiology, 1997 4th Edition Garland Press 1999.
International Search Report issued Jul. 8, 2014 in PCT/JP2014/059352 filed Mar. 28, 2014.
International Preliminary Report on Patentability issued Oct. 8, 2015 in PCT/JP2014/059352 filed Mar. 28, 2014 (English translation only).
Francesca Di Modugno, et al., MHC-Peptide Binding: Dimers of Cysteine-Containing Nonapeptides Bind with High Affinity to HLA-A2.1 Class 1 Molecules, Journal of Immunotherapy, 1997, vol. 20, No. 6, pp. 431-436.
Nature Reviews Drug Discovery. Sep. 2009, vol. 8, pp. 685-686.
Craig L. Slingluff Jr., M.D., "The Present and Future of Peptide Vaccines for Cancer: Single or Multiple, Long or Short, Alone or in Combination?", Cancer Journal, 2011, 17(5), pp. 343-350.
Shih-Chung CHANG, "The ER aminopeptidase, ERAP1, trims precursors to lengths of MHC class I peptides by a "molecular ruler" mechanism", Proceedings of the National Academy of Sciences of United States of America, 2005, vol. 102, No. 47, pp. 17107-17112.
Irini Evnouchidou, "The Internal Sequence of the Peptide-Substrate Determines Its N-Terminus Trimming by ERAP1", PLoS One, 2008; vol. 3, Issue 11, e3658; pp. 1-12.
Arron Hearn, et al., "The Specificity of Trimming of MHC Class I-Presented Peptides in the Endoplasmic Reticulum", The Journal of Immunology, 2009, 183, pp. 5526-5536.
Arron Hearn, et al., "Characterizing the Specificity and Cooperation of Aminopeptidases in the Cytosol and Endoplasmic Reticulum during MHC Class 1 Antigen Presentation", Journal of Immunology, 2010, 184; pp. 4725-4732.
Supplementary Partial European Search Report issued Oct. 13, 2016 in Patent Application 14773223.4.
Extended European Search Report issued Sep. 19, 2016 in Patent Application No. 14775899.9.
Valerie Dutoit, et al., "Dissecting TCR-MHC/peptide Complex Interactions with A2/peptide Multimers Incorporating Tumor Antigen Peptide Variants: Crucial Role of Interaction Kinetics on

(56) References Cited

OTHER PUBLICATIONS

Functional Outcomes" European Journal of Immunology, vol. 32, No. 11, XP055305530, Nov. 1, 2002, pp. 3285-3293.
Peter Van Endert, "Post-proteasomal and Proteasome-independent Generation of MHC Class 1 Ligands" Cellular and Molecular Life Sciences, vol. 68, No. 9, XP019894461, Mar. 10, 2011, pp. 1553-1567.
Extended European Search Report issued Feb. 8, 2017 in Patent Application No. 14773223.4.
Katayoun Rezvani,et al., "Leukemia-associated antigen-specific T-cell responses following combined PR1and WT1 peptide vaccination in patients with myeloid malignancies" Immunobiokogy, Blood, vol. 111, No. 1, XP055339775, Jan. 1, 2008, From www.bloodjournal.org by guest on Jan. 27, 2017, pp. 236-242.
Jeffrey J. Molldrem. et al., "Cytotoxic T Lymphocytes Specific for a Nonpolymorphic Proteinase 3 Peptide Preferentially Inhibit Chronic Myeloid Leukemia Colony-Forming Units" Rapid Communication, Blood, vol. 90, No. 7, XP002300135, Oct. 1, 1997, pp. 2529-2534.
Office Action issued Oct. 3, 2017 in JP 2015-508814, filed Sep. 25, 2015 (with English transtation).
Gomez-Nunez et al., "Non-Natural and Photo-Reactive Amino Acids as Biochemical Probes of Immune Function", PLoS ONE, vol. 3, Issue 12, e3938, Dec. 2008, 9 pages.
Gentle et al., "Direct Production of Proteins with N-Terminal Cysteine for Site-Specific Conjugation", Bioconjugate Chem., 2004, 15, pp. 658-663.
Fisk et al., "Identification of an Immunodominant Peptide of HER-2/neu Protooncogene Recognized by Ovarian Tumor-specific Cytotoxic T Lymphocyte Lines", J. Exp. Med., vol. 181, Jun. 1995, pp. 2109-2117.
Chianese-Bullock et al., "Multi-Peptide Vaccines Vialed as Peptide Mixtures Can Be Stable Reagents for Use in Peptide-Based Immune Therapies", Vaccine, 27(11), 2009, pp. 1764-1770.
International Preliminary Report on Patentability and Written Opinion issued on Jun. 13, 2019 in PCT/JP2017/042760, citing documents therein, 10 pages.
International Search Report issued on Jan. 16, 2018 in PCT/JP2017/042760, citing documents therein, 2 pages.
Ueda, N. et al., "BCR-ABL-specific CD4+ T-helper cells promote the priming of antigen-specific cytotoxic T cells via dendritic cell", Cellular and Molecular Immunology, vol. 13, May 2016, pp. 1-12.
Cheever, M. A. et al., "The Prioritization of Cancer Antigens: A National Cancer Institute Pilot Project for the Acceleration of Translational Research", Clin Cancer Res, vol. 15, No. 17, Sep. 1, 2009, pp. 5323-5337.
Gao, F. G. et al., "Antigen-specific CD4+ T-Cell Help Is Required to Activate a Memory CD8+ T Cell to a Fully Functional Tumor Killer Cell", Cancer Research, vol. 62, No. 22, Nov. 15, 2002, pp. 6438-6441.
Zeng, G., "MHC Class II-Restricted Tumor Antigens Recognized by CD4+ T Cells: New Strategies for Cancer Vaccine Design", Journal of Immunotherapy, vol. 24, No. 3, 2001, pp. 195-204.
Holland, C. J. et al., "Re-Directing CD4+ T cell responses with the flanking residues of MHC class II-bound peptides: the core is not enough", Frontiers in Immunology, vol. 4, No. 172, Jul. 2013, pp. 1-9.
Godkin, A. J. et al., "Naturally Processed HLA Class II Peptides Reveal Highly Conserved Immunogenic Flanking Region Sequence Preferences That Reflect Antigen Processing Rather Than Peptide-MHC Interactions", Journal of Immunology, vol. 166, No. 11, 2001, pp. 6720-6727.
Arnold, P. Y. et al., "The Majority of Immunogenic Epitopes Generate CD4+ T Cells That Are Dependent on MHC Class II-Bound Peptide-Flanking Residues", Journal of Immunology, vol. 169, No. 2, 2002, pp. 739-749 (with correction page).
Carson, R. T. et al., "T Cell Receptor Recognition of MHC Class II-Bound Peptide Flanking Residues Enhances Immunogenicity and Results in Altered TCR V Region Usage", Immunity, vol. 7, No. 3, Sep. 1997, pp. 387-399.
Lovitch, S. B. et al., "Amino-Terminal Flanking Residues Determine the Conformation of a Peptide-Class II MHC Complex", Journal of Immunology, vol. 176, No. 5, 2006, pp. 2958-2968.
Nelson, C. A. et al., "Identification of two distinct properties of class II major histocompatibility complex-associated peptides", Proc. Natl. Acad. Sci. USA, vol. 90, No. 4, Feb. 1993, pp. 1227-1231.
Extended European Search Report issued Jul. 8, 2020 in corresponding European Patent Application No. 17875568.2 citing documents therein, 9 pages.
Van Driessche et al. (Oncologist. Feb. 2012 : 17 (2): 250-259).
Koido et al. (Clin. Cancer Res. Aug. 15, 2014; 20 (16): 4228-39).
Haber et al. (Proc. Natl. Acad. Sci USA. Nov. 1, 1991; 88 (21): 9618-22).
U.S. Pat. No. 10,588,952, Mar. 17, 2020, US2016/0045582 A1 Ban, et al.
U.S. Pat. No. 9,248,173, Feb. 2, 2016, US2015/0038587 A1, Li, et al.
U.S. Pat. No. 9,181,302, Nov. 10, 2015, US2015/0080321 A1, Li, et al.
U.S. Appl. No. 14/984,763, filed Dec. 30, 2015, US2016/0114019 A1, Li, et al.
U.S. Appl. No. 16/163,067, filed Oct. 17, 2018, US2019/0030149 A1, Li, et al.
U.S. Appl. No. 16/785,958, filed Feb. 10, 2020, US 2020-0171136 A1, Ban, et al.
U.S. Appl. No. 15/575,162, filed Nov. 17, 2017, 2018-0140691-A1, Takasu, et al.
Interference No. 105987—Exhibit 1035—Preliminary Amendment filed Jul. 2, 2009, in Sugiyama U.S. Appl. No. 12/181,938.
Abcam (downloaded from URL:< https://docs.abcam.com/pdf/antibody-guide/tips-for-designing-a-good-peptide-immunogen.pdf>, Jul. 2, 2011) (Year: 2011).
Office Action issued on Dec. 1, 2020 in U.S. Appl. No. 16/785,958.
Office Action issued in U.S. Appl. No. 16/163,067 on Sep. 28, 2021.
Kazushi Inoue, et al., "Aberrant Overexpression of the Wilms Tumor Gene (WT1) in Human Leukemia", Blood, 1997, vol. 89. No. 4, pp. 1405-1412.
Yoshihiro Oka, et al., "Human cytotoxic T-lymphocyte responses specific for peptides of the wild-type Wilms' tumor gene (WT1) product", Immunogenetics, 2000, 51, pp. 99-107.
Katayoun Rezvani, et al., "T-Cell Responses Directed against Multiple HLA-A*0201-Restricted Epitopes Derived from Wilms' Tumor 1Protein in Patients with Leukemia and Healthy Donors: Identification, Quantification, and Characterization", Clinical Cancer Research, 2005, 11, pp. 8799-8807 (cover page).
Coralie Chaise, "DNA vaccination induces WT1-specific T-cell responses with potential clinical relevance", Blood, 2008, vol. 112, No. 7, pp. 2956-2964.
Fumihiro Fujiki et al., "Identification and Characterization of a WT1 (Wilms Tumor Gene) Protein-derived HLA-DRB1*0405-restricted 16-mer Helper Peptide That Promotes the Induction and Activation of WT1-specific Cytotoxic T Lymphocytes", J Immunother., 2007, vol. 30, No. 3, pp. 282-293.
Drew M. Pardoll. "The blockade of immune checkpoints in cancer immunotherapy", Nat Rey Cancer, 2012, vol. 12, pp. 252-264.
Kathleen M. Mahoney, et al., "Combination cancer immunotherapy and now immunomodulatory targets", Nature Reviews Drug Discovery, 2015, vol. 14, (8), pp. 561-584.
Sheng Yao, "Advances in targeting cell surface signalling molecules for immune modulation", Nature Reviews Drug Discovery, 2013, vol. 12, (2), pp. 130-146.
Chunmel Fu et al., "β-catenin-mediated inhibition of cross-priming: A new mechanism for tumors to evade immunosurveillance", Oncoimmunology, 2013, vol. 2, No. 12, 3 pages.
David Stather, et al., "High PD-1 Levels at Baseline are Associated With unfavourable Clinical Outcome in a Wilms Tumour Gene 1 (Wt1) Peptide Vaccination Setting in Leukemia Patients", J. Immunother., 2011, vol. 34, No. 9, p. 704.
C. Riother, et al., Blocking programmed cell death 1 in combination with adoptive cytotoxic T-cell transfor eradicates chronic myologonous leukemia stom cells, Leukemia, 2015, vol. 29, N. 8, pp. 1781-1785.

(56) References Cited

OTHER PUBLICATIONS

English translation of the International Preliminary Report on Patentability issued Nov. 30, 2017, in PCT/JP2016/064923, 10 pages.
International Search Report issued Aug. 16, 2016 in PCT/JP2016/064923, 3 pages.
Mary Saleh, et al., "A Novel Zinc Finger Gens on Human Chromosome I qter That Is Alternatively Spliced in Human Tissues and Cell Lines", Am J Hum Genot., 1993, 52, pp. 192-203.
Japanese Office Action issued on Nov. 5, 2019, In Patent Application No. 2019-076826, 7 pages.
Tamada, K. et al., "Modulation of T-Cell medlated immunity in tumor and graft-versus-host disease models through the LIGHT co-stimulatory pathway", Nature Medicine, vol. 6, No. 3, Mar. 2000, pp. 283-289.
Sucher, R. et al., "IDO-Mediated Tryptophan Degradation in the Pathogenesis of Malignant Tumor Disease", International Journal of Tryptophan Research, vol. 3, 2010, pp. 113-120.
Bertolini, F. et al., "CXCR4 Neutralization, a Novel Therapeutic Approach for Non-Hodgkin's Lymphoma", Cancer Research, vol. 62, 2002, pp. 3106-3112.
Kong, L. Y. et al., "A novel phosphorylated STAT3 inhibitor enhances T cell cytotoxicity against melanoma through inhibition of regulatory T cells", Cancer Immunol Immunother, vol. 58, 2009, pp. 1023-1032.
Joyce, J.A., et al.. "T Cell Exclusion, Immune Privilege, and the Tumor Microenvironment", Science, vol. 348 No. 6230, Apr. 2015, pp. 74-80 with cover page.
Sebastian Kobold, et al.—"Modes of Action of TLR7 agonists in cancer therapy", Immunotherapy (2014) vol. 6. No. 10) pp. 1085-1095.
Office Action issued in corresponding Chinese Patent Application No. 201680042322.X on Sep. 30, 2020, (with English Translation), citing document listed therein.
Office Action Issued on Jul. 5, 2021 in corresponding Chinese Application No. 201680042322.X with English Translation.
Bodey et al. (Anticancer Res. Jul.-Aug. 2000; 20 (4): 2665-76).
Lollini et al. (Curr. Cancer Drug Targets, May 2005; 5 (3): 221-228).
Lollini et al. (Trends Immunol, Feb. 2003: 24 (2): 62-66).
Slinghluff et al. (Cancer Immunol. Immunother. Mar. 2000: 48 (12): 661-672).
Singh et al. (Cancer Res. Mar. 1, 2007: 67 (5): 1887-92).
Bordin et al. (Haematologica, Feb. 2018; 103 (2): 266-277).
Stancovski et al. (Proc. Natl. Acad. Scl. USA, Oct. 1, 1991: 88 (19): 8691-5).
Chin et al. (Chang Gung Med J. Jan.-Feb. 2008; 31 (1): 1-15).
Jiang et al. (J. Biol, Chem. Feb. 11, 2005; 280 (6): 4656-4662).
Riemer et al. (Mol. Immunol. 2005; 42: 1121-1124).
Ingram et al. (Proc. Natl. Acad. Sci. USA. Apr. 1, 2018 O; 115 (15): 3912-3917).
Oh et al. (Mol. Cells. Dec. 2012; 34 (6): 523-9).
Chen et al. (J. Immunol, Nov. 15, 2013; 191 (10): 5097-106).
Kuball et al. (Cancer Immunol. Immunother, 2011; 60: 161-71).
Atanackovic et al. (Leukemia, May 2014; 28 (5): 993-1000).
Curran et al. (Proc. Natl. Acad. Sci. USA. Mar. 2, 2010; 107 (9): 4275-80).
Koldo et al. (Clin. Cancer Res. Aug. 15, 2014; 20 (16): 4228-39).
Evnouchidou et al. (PLoS ONE 3(11): e3658, 2008) (Year: 2008).
Hearn et al. (J Immunol 2009; 183:5526-5536) (Year: 2009).
Rock et al. (Immunol 201 O; 184:4725-4732) (Year: 2010).
Chang et al. (Proc Natl Acad Sci USA. Nov. 22, 2005; 102(47):17107-12) (Year: 2005).
Office Action Issued in U.S. Appl. No. 16/785,958 on Jul. 22, 2021.
Extended European Search Report issued Jan. 24, 2019, in European Patent Application No. 16796570.6, 10 pages.
Robert et al. (Lancet. Sep. 20, 2014; 384 (9948): 1109-17).
U.S. Office Action issued on Oct. 24, 2022 in U.S. Appl. No. 15/575,162.
Qi, Xiao-Wei, "Association between WT1 polymorphisms and susceptibility to breast cancer: results from a case-control study in a southwestern Chinese population", Am J Cancer Res 2015;5(3) 1234-1250.
Hou, Hsln-An "WT1 mutation in 470 adult patients with acute myeloid leukemia: stability during disease evolution and implication of its incorporation into a survival scoring system"; Blood, Jun. 24, 2010 • vol. 115, No. 25, 10 pages.
Tuttle et al., "A Phase 2 Trial of Peresolimab for Adults with Rheunlatoid Arthritis" The New England Journal of Medicine, May 18, 2023, 388(20), pp. 1853-1862.
Soo M. Ngoi, et al., "Targeting Poly I:C to the TLR3-independent pathway boosts effector CD8 T cell differentiation through IFNα/β," J. Immunol., Dec. 1, 2008, vol. 181, No. 11, 22 pages.
Rose S. Chu, et al., "CpG Oligodeoxynucleotides Act as Adjuvants that Switch on T Helper 1 (Th1) Immunity," J. Exp. Med., vol. 186, No. 10, Nov. 17, 1997, pp. 1623-1631.
Japanese Office Action issued Aug. 2, 2022 in Japanese Patent Application No. 2021-154508, 6 pages (with English machine translation).
Chinese Office Action dated Apr. 26, 2022 issued in corresponding Chinese patent application 201680042322.X (with English translation).
Yang Pingling et al., Research Progress on the relationship between β-catenin and colorectal cancer, The Journal of Practical Medicine vol. 24, No. 8, 2008, pp. 1286-1288 (with English machine translation).

* cited by examiner

SEQUENCE LISTING

<160> NUMBER OF SEQ ID NOS: 75

<210> SEQ ID NO 1
<211> LENGTH: 449
<212> TYPE: PRT
<213> ORGANISM: Homo sapiens

<400> SEQUENCE: 1

```
Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285
```

His Thr His Gly Val Phe Arg Gly Ile Gln Asp Val Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
            435                 440                 445

Leu

<210> SEQ ID NO 2
<211> LENGTH: 15
<212> TYPE: PRT
<213> ORGANISM: Artificial Sequence
<220> FEATURE:
<223> OTHER INFORMATION: Peptide

<400> SEQUENCE: 2

Ala Tyr Pro Gly Cys Asn Lys Arg Tyr Phe Lys Leu Ser His Leu
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Peptide

<400> SEQUENCE: 3

Tyr Pro Gly Cys Asn Lys Arg Tyr Phe Lys Leu Ser His Leu Gln
1               5                   10                  15

<210> SEQ ID NO 4
<211> LENGTH: 22
<212> TYPE: PRT
<213> ORGANISM: Artificial Sequence
<220> FEATURE:
<223> OTHER INFORMATION: Peptide

<400> SEQUENCE: 4

Pro Gly Cys Asn Lys Arg Tyr Phe Lys Leu Ser His Leu Gln Met His
1               5                   10                  15

Ser Arg Lys His Thr Gly
            20

<210> SEQ ID NO 5
<211> LENGTH: 19
<212> TYPE: PRT

```
<213> ORGANISM: Artificial Sequence
<220> FEATURE:
<223> OTHER INFORMATION: Peptide

<400> SEQUENCE: 5

Pro Gly Cys Asn Lys Arg Tyr Phe Lys Leu Ser His Leu Gln Met His
1               5                   10                  15

Ser Arg Lys

<210> SEQ ID NO 6
<211> LENGTH: 18
<212> TYPE: PRT
<213> ORGANISM: Artificial Sequence
<220> FEATURE:
<223> OTHER INFORMATION: Peptide

<400> SEQUENCE: 6

Gly Cys Asn Lys Arg Tyr Phe Lys Leu Ser His Leu Gln Met His Ser
1               5                   10                  15

Arg Lys

<210> SEQ ID NO 7
<211> LENGTH: 17
<212> TYPE: PRT
<213> ORGANISM: Artificial Sequence
<220> FEATURE:
<223> OTHER INFORMATION: Peptide

<400> SEQUENCE: 7

Cys Asn Lys Arg Tyr Phe Lys Leu Ser His Leu Gln Met His Ser Arg
1               5                   10                  15

Lys

<210> SEQ ID NO 8
<211> LENGTH: 16
<212> TYPE: PRT
<213> ORGANISM: Artificial Sequence
<220> FEATURE:
<223> OTHER INFORMATION: Peptide

<400> SEQUENCE: 8

Asn Lys Arg Tyr Phe Lys Leu Ser His Leu Gln Met His Ser Arg Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Peptide

<400> SEQUENCE: 9

Lys Arg Tyr Phe Lys Leu Ser His Leu Gln Met His Ser Arg Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Peptide

<400> SEQUENCE: 10

Lys Arg Tyr Phe Lys Leu Ser His Leu Gln Met His Ser Arg Lys His
1               5                   10                  15
```

<210> SEQ ID NO 11
<211> LENGTH: 15
<212> TYPE: PRT
<213> ORGANISM: Artificial Sequence
<220> FEATURE:
<223> OTHER INFORMATION: Peptide

<400> SEQUENCE: 11

Arg Tyr Phe Lys Leu Ser His Leu Gln Met His Ser Arg Lys His
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Peptide

<400> SEQUENCE: 12

Tyr Phe Lys Leu Ser His Leu Gln Met His Ser Arg Lys His Thr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Peptide

<400> SEQUENCE: 13

Phe Lys Leu Ser His Leu Gln Met His Ser Arg Lys His Thr Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Peptide

<400> SEQUENCE: 14

Lys Leu Ser His Leu Gln Met His Ser Arg Lys His Thr Gly Glu
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Peptide

<400> SEQUENCE: 15

Arg Met Phe Pro Asn Ala Pro Tyr Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Peptide

<400> SEQUENCE: 16

Cys Met Thr Trp Asn Gln Met Asn Leu
1               5

```
<210> SEQ ID NO 17
<211> LENGTH: 9
<212> TYPE: PRT
<213> ORGANISM: Artificial Sequence
<220> FEATURE:
<223> OTHER INFORMATION: Peptide

<400> SEQUENCE: 17

Cys Tyr Thr Trp Asn Gln Met Asn Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Peptide

<400> SEQUENCE: 18

Ala Leu Leu Pro Ala Val Pro Ser Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Peptide

<400> SEQUENCE: 19

Ser Leu Gly Glu Gln Gln Tyr Ser Val
1               5

<210> SEQ ID NO 20
<211> LENGTH: 9
<212> TYPE: PRT
<213> ORGANISM: Artificial Sequence
<220> FEATURE:
<223> OTHER INFORMATION: Peptide

<400> SEQUENCE: 20

Arg Val Pro Gly Val Ala Pro Thr Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Peptide

<400> SEQUENCE: 21

Val Leu Asp Phe Ala Pro Pro Gly Ala
1               5

<210> SEQ ID NO 22
<211> LENGTH: 9
<212> TYPE: PRT
<213> ORGANISM: Artificial Sequence
<220> FEATURE:
<223> OTHER INFORMATION: Peptide

<400> SEQUENCE: 22

Arg Tyr Phe Pro Asn Ala Pro Tyr Leu
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Peptide

<400> SEQUENCE: 23

Phe Met Phe Pro Asn Ala Pro Tyr Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Peptide

<400> SEQUENCE: 24

Arg Leu Phe Pro Asn Ala Pro Tyr Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Peptide

<400> SEQUENCE: 25

Arg Met Met Pro Asn Ala Pro Tyr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Peptide

<400> SEQUENCE: 26

Arg Met Phe Pro Asn Ala Pro Tyr Val
1               5

<210> SEQ ID NO 27
<211> LENGTH: 9
<212> TYPE: PRT
<213> ORGANISM: Artificial Sequence
<220> FEATURE:
<223> OTHER INFORMATION: Peptide

<400> SEQUENCE: 27

Tyr Met Phe Pro Asn Ala Pro Tyr Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (1)..(1)
<223> OTHER INFORMATION: Xaa is Ser or Ala

<400> SEQUENCE: 28

Xaa Met Thr Trp Asn Gln Met Asn Leu
```

```
1               5

<210> SEQ ID NO 29
<211> LENGTH: 9
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (1)..(1)
<223> OTHER INFORMATION: Xaa is Ser, Ala, Abu, Arg, Lys, Orn, Cit, Leu,
      Phe, or Asn

<400> SEQUENCE: 29

Xaa Tyr Thr Trp Asn Gln Met Asn Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Peptide

<400> SEQUENCE: 30

Ala Tyr Leu Pro Ala Val Pro Ser Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Peptide

<400> SEQUENCE: 31

Phe Leu Gly Glu Gln Gln Tyr Ser Val
1               5

<210> SEQ ID NO 32
<211> LENGTH: 9
<212> TYPE: PRT
<213> ORGANISM: Artificial Sequence
<220> FEATURE:
<223> OTHER INFORMATION: Peptide

<400> SEQUENCE: 32

Ser Met Gly Glu Gln Gln Tyr Ser Val
1               5

<210> SEQ ID NO 33
<211> LENGTH: 9
<212> TYPE: PRT
<213> ORGANISM: Artificial Sequence
<220> FEATURE:
<223> OTHER INFORMATION: Peptide

<400> SEQUENCE: 33

Ser Leu Met Glu Gln Gln Tyr Ser Val
1               5

<210> SEQ ID NO 34
<211> LENGTH: 9
<212> TYPE: PRT
<213> ORGANISM: Artificial Sequence
<220> FEATURE:
<223> OTHER INFORMATION: Peptide
```

```
<400> SEQUENCE: 34

Arg Tyr Pro Gly Val Ala Pro Thr Leu
1               5

<210> SEQ ID NO 35
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Protected with Npys group

<400> SEQUENCE: 35

Cys Arg Met Phe Pro Asn Ala Pro Tyr Leu
1               5                   10

<210> SEQ ID NO 36
<211> LENGTH: 20
<212> TYPE: PRT
<213> ORGANISM: Artificial Sequence
<220> FEATURE:
<223> OTHER INFORMATION: Peptide

<400> SEQUENCE: 36

Pro Gly Cys Asn Lys Arg Tyr Phe Lys Leu Ser His Leu Gln Met His
1               5                   10                  15

Ser Arg Lys His
            20

<210> SEQ ID NO 37
<211> LENGTH: 18
<212> TYPE: PRT
<213> ORGANISM: Artificial Sequence
<220> FEATURE:
<223> OTHER INFORMATION: Peptide

<400> SEQUENCE: 37

Cys Asn Lys Arg Tyr Phe Lys Leu Ser His Leu Gln Met His Ser Arg
1               5                   10                  15

Lys His

<210> SEQ ID NO 38
<211> LENGTH: 20
<212> TYPE: PRT
<213> ORGANISM: Artificial Sequence
<220> FEATURE:
<223> OTHER INFORMATION: Peptide

<400> SEQUENCE: 38

Cys Asn Lys Arg Tyr Phe Lys Leu Ser His Leu Gln Met His Ser Arg
1               5                   10                  15

Lys His Thr Gly
            20

<210> SEQ ID NO 39
<211> LENGTH: 14
<212> TYPE: PRT
<213> ORGANISM: Artificial Sequence
<220> FEATURE:
<223> OTHER INFORMATION: Peptide

<400> SEQUENCE: 39
```

```
Arg Tyr Phe Lys Leu Ser His Leu Gln Met His Ser Arg Lys
1               5                   10
```

```
<210> SEQ ID NO 40
<211> LENGTH: 13
<212> TYPE: PRT
<213> ORGANISM: Artificial Sequence
<220> FEATURE:
<223> OTHER INFORMATION: Peptide

<400> SEQUENCE: 40

Tyr Phe Lys Leu Ser His Leu Gln Met His Ser Arg Lys
1               5                   10
```

```
<210> SEQ ID NO 41
<211> LENGTH: 12
<212> TYPE: PRT
<213> ORGANISM: Artificial Sequence
<220> FEATURE:
<223> OTHER INFORMATION: Peptide

<400> SEQUENCE: 41

Phe Lys Leu Ser His Leu Gln Met His Ser Arg Lys
1               5                   10
```

```
<210> SEQ ID NO 42
<211> LENGTH: 11
<212> TYPE: PRT
<213> ORGANISM: Artificial Sequence
<220> FEATURE:
<223> OTHER INFORMATION: Peptide

<400> SEQUENCE: 42

Lys Leu Ser His Leu Gln Met His Ser Arg Lys
1               5                   10
```

```
<210> SEQ ID NO 43
<211> LENGTH: 18
<212> TYPE: PRT
<213> ORGANISM: Artificial Sequence
<220> FEATURE:
<223> OTHER INFORMATION: Peptide

<400> SEQUENCE: 43

Ala Tyr Pro Gly Cys Asn Lys Arg Tyr Phe Lys Leu Ser His Leu Gln
1               5                   10                  15

Met His
```

```
<210> SEQ ID NO 44
<211> LENGTH: 21
<212> TYPE: PRT
<213> ORGANISM: Artificial Sequence
<220> FEATURE:
<223> OTHER INFORMATION: Peptide

<400> SEQUENCE: 44

Ala Tyr Pro Gly Cys Asn Lys Arg Tyr Phe Lys Leu Ser His Leu Gln
1               5                   10                  15

Met His Ser Arg Lys
            20
```

```
<210> SEQ ID NO 45
<211> LENGTH: 11
<212> TYPE: PRT
<213> ORGANISM: Artificial Sequence
```

```
<220> FEATURE:
<223> OTHER INFORMATION: Peptide

<400> SEQUENCE: 45

Arg Tyr Phe Lys Leu Ser His Leu Gln Met His
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Peptide

<400> SEQUENCE: 46

Gly Cys Asn Lys Arg Tyr Phe Lys Leu Ser His Leu
1               5                   10

<210> SEQ ID NO 47
<211> LENGTH: 16
<212> TYPE: PRT
<213> ORGANISM: Artificial Sequence
<220> FEATURE:
<223> OTHER INFORMATION: Peptide

<400> SEQUENCE: 47

Phe Lys Leu Ser His Leu Gln Met His Ser Arg Lys His Thr Gly Glu
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Peptide

<400> SEQUENCE: 48

Arg Tyr Phe Lys Leu Ser His Leu Gln Met His Ser Arg Lys His Thr
1               5                   10                  15

<210> SEQ ID NO 49
<211> LENGTH: 18
<212> TYPE: PRT
<213> ORGANISM: Artificial Sequence
<220> FEATURE:
<223> OTHER INFORMATION: Peptide

<400> SEQUENCE: 49

Arg Tyr Phe Lys Leu Ser His Leu Gln Met His Ser Arg Lys His Thr
1               5                   10                  15

Gly Glu

<210> SEQ ID NO 50
<211> LENGTH: 12
<212> TYPE: PRT
<213> ORGANISM: Artificial Sequence
<220> FEATURE:
<223> OTHER INFORMATION: Peptide

<400> SEQUENCE: 50

Lys Leu Ser His Leu Gln Met His Ser Arg Lys His
1               5                   10

<210> SEQ ID NO 51
<211> LENGTH: 20
<212> TYPE: PRT
```

```
<213> ORGANISM: Artificial Sequence
<220> FEATURE:
<223> OTHER INFORMATION: Peptide

<400> SEQUENCE: 51

Tyr Pro Gly Cys Asn Lys Arg Tyr Phe Lys Leu Ser His Leu Gln Met
1               5                   10                  15

His Ser Arg Lys
            20

<210> SEQ ID NO 52
<211> LENGTH: 20
<212> TYPE: PRT
<213> ORGANISM: Artificial Sequence
<220> FEATURE:
<223> OTHER INFORMATION: Peptide

<400> SEQUENCE: 52

Ala Tyr Pro Gly Cys Asn Lys Arg Tyr Phe Lys Leu Ser His Leu Gln
1               5                   10                  15

Met His Ser Arg
            20

<210> SEQ ID NO 53
<211> LENGTH: 19
<212> TYPE: PRT
<213> ORGANISM: Artificial Sequence
<220> FEATURE:
<223> OTHER INFORMATION: Peptide

<400> SEQUENCE: 53

Ala Tyr Pro Gly Cys Asn Lys Arg Tyr Phe Lys Leu Ser His Leu Gln
1               5                   10                  15

Met His Ser

<210> SEQ ID NO 54
<211> LENGTH: 17
<212> TYPE: PRT
<213> ORGANISM: Artificial Sequence
<220> FEATURE:
<223> OTHER INFORMATION: Peptide

<400> SEQUENCE: 54

Ala Tyr Pro Gly Cys Asn Lys Arg Tyr Phe Lys Leu Ser His Leu Gln
1               5                   10                  15

Met

<210> SEQ ID NO 55
<211> LENGTH: 16
<212> TYPE: PRT
<213> ORGANISM: Artificial Sequence
<220> FEATURE:
<223> OTHER INFORMATION: Peptide

<400> SEQUENCE: 55

Ala Tyr Pro Gly Cys Asn Lys Arg Tyr Phe Lys Leu Ser His Leu Gln
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Peptide
```

```
<400> SEQUENCE: 56

Tyr Phe Lys Leu Ser His Leu Gln Met His Ser Arg Lys His Thr Gly
1               5                   10                  15

Glu

<210> SEQ ID NO 57
<211> LENGTH: 17
<212> TYPE: PRT
<213> ORGANISM: Artificial Sequence
<220> FEATURE:
<223> OTHER INFORMATION: Peptide

<400> SEQUENCE: 57

Arg Tyr Phe Lys Leu Ser His Leu Gln Met His Ser Arg Lys His Thr
1               5                   10                  15

Gly

<210> SEQ ID NO 58
<211> LENGTH: 13
<212> TYPE: PRT
<213> ORGANISM: Artificial Sequence
<220> FEATURE:
<223> OTHER INFORMATION: Peptide

<400> SEQUENCE: 58

Arg Tyr Phe Lys Leu Ser His Leu Gln Met His Ser Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Peptide

<400> SEQUENCE: 59

Arg Tyr Phe Lys Leu Ser His Leu Gln Met His Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Peptide

<400> SEQUENCE: 60

Arg Tyr Phe Lys Leu Ser His Leu Gln Met
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Peptide

<400> SEQUENCE: 61

Tyr Pro Gly Cys Asn Lys Arg Tyr Phe Lys Leu Ser His Leu
1               5                   10

<210> SEQ ID NO 62
<211> LENGTH: 13
<212> TYPE: PRT
<213> ORGANISM: Artificial Sequence
```

```
<220> FEATURE:
<223> OTHER INFORMATION: Peptide

<400> SEQUENCE: 62

Pro Gly Cys Asn Lys Arg Tyr Phe Lys Leu Ser His Leu
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Peptide

<400> SEQUENCE: 63

Cys Asn Lys Arg Tyr Phe Lys Leu Ser His Leu
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Peptide

<400> SEQUENCE: 64

Asn Lys Arg Tyr Phe Lys Leu Ser His Leu
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Peptide

<400> SEQUENCE: 65

Lys Leu Ser His Leu Gln Met His Ser Arg Lys His Thr Gly
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Peptide

<400> SEQUENCE: 66

Lys Leu Ser His Leu Gln Met His Ser Arg Lys His Thr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Peptide

<400> SEQUENCE: 67

Lys Leu Ser His Leu Gln Met His Ser Arg Lys
1               5                   10

<210> SEQ ID NO 68
<211> LENGTH: 10
<212> TYPE: PRT
<213> ORGANISM: Artificial Sequence
<220> FEATURE:
```

```
<223> OTHER INFORMATION: Peptide

<400> SEQUENCE: 68

Lys Leu Ser His Leu Gln Met His Ser Arg
1               5                   10

<210> SEQ ID NO 69
<211> LENGTH: 55
<212> TYPE: PRT
<213> ORGANISM: Artificial Sequence
<220> FEATURE:
<223> OTHER INFORMATION: Amino acid sequence at positions 311-365 of SEQ
      ID NO: 1

<400> SEQUENCE: 69

Val Arg Ser Ala Ser Glu Thr Ser Glu Lys Arg Pro Phe Met Cys Ala
1               5                   10                  15

Tyr Pro Gly Cys Asn Lys Arg Tyr Phe Lys Leu Ser His Leu Gln Met
                20                  25                  30

His Ser Arg Lys His Thr Gly Glu Lys Pro Tyr Gln Cys Asp Phe Lys
            35                  40                  45

Asp Cys Glu Arg Arg Phe Ser
        50                  55

<210> SEQ ID NO 70
<211> LENGTH: 10
<212> TYPE: PRT
<213> ORGANISM: Artificial Sequence
<220> FEATURE:
<223> OTHER INFORMATION: Synthetic peptide

<400> SEQUENCE: 70

Cys Cys Tyr Thr Trp Asn Gln Met Asn Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide

<400> SEQUENCE: 71

Cys Cys Met Thr Trp Asn Gln Met Asn Leu
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide

<400> SEQUENCE: 72

Cys Ala Leu Leu Pro Ala Val Pro Ser Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73
```

```
Cys Ser Leu Gly Glu Gln Gln Tyr Ser Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide

<400> SEQUENCE: 74

Cys Arg Val Pro Gly Val Ala Pro Thr Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic peptide

<400> SEQUENCE: 75

Cys Val Leu Asp Phe Ala Pro Pro Gly Ala
1               5                   10
```

WT1 HELPER PEPTIDES AND COMBINATIONS OF WT1 HELPER PEPTIDE AND CONJUGATE OF CANCER ANTIGEN PEPTIDES

TECHNICAL FIELD

The present application claims the benefit of Japanese Patent Application No. 2016-233042, which is incorporated herein by reference in its entirety.

The present invention relates to cancer immunotherapy and, in particular, a WT1 helper peptide and a combination thereof with a conjugate of cancer antigen peptides, for example.

BACKGROUND

WT1 Gene was isolated as a responsible gene of Wilms tumor, which is a kidney cancer in children. Leukemia and some solid cancers are known to be associated with high expression of WT1. WT1 Protein is one of cancer antigen proteins of strong interest for use in cancer vaccines.
(Non-Patent Literature 1)

Cellular immunity, especially cytotoxic T cells (cytotoxic T lymphocytes) (referred to as CTLs hereinafter) play an important role in cancer cell clearance by living body. CTLs which attack cancer cells are derived from precursor T cells through their differentiation and proliferation, upon recognition by precursor T cells of a peptide having 8 to 13 amino acid residues from a cancer antigen protein complexed with an MHC class I molecule. The following MHC class I-restricted peptides (also referred to as killer peptides) are known from WT1 protein:

```
                                    (SEQ ID NO: 15)
WT1_{126-134} peptide: RMFPNAPYL (Arg-Met-Phe-Pro- Asn-Ala-Pro-Tyr-Leu),
and
                                    (SEQ ID NO: 17)
WT1_{235-243 (2M->Y)} peptide: CYTWNQMNL (Cys- Tyr-Thr-Trp-Asn-Gln-Met-Asn-Leu)
```

(Non-Patent Literatures 1 and 2).

Function of CTLs in cancer immunotherapy is known to be enhanced by activation of helper T cells (non-patent literatures 2 and 3). Helper T cells are derived from precursor T cells through their differentiation and proliferation, upon recognition by precursor T cells of a peptide having 9 to 30 amino acid residues from a cancer antigen protein complexed with an MHC class II molecule. It is known that only nine amino acid residues in such a peptide are directly involved in the binding with an MHC class II molecule. The remaining sequence of amino acid residues not directly involved in the binding with an MHC class II molecule is called a peptide franking region (hereinafter referred to as PFR) (non-patent literatures 4-9).

As MHC class IF-restricted peptides (also referred to as helper peptides), that is, antigen peptides which can form a complex with an MHC class II molecule and induce differentiation and proliferation of helper T cells, the following peptides are known from WT1 protein:

```
WT1_{330-346} peptide:
                                    (SEQ ID NO: 7)
CNKRYFKLSHLQMHSRK (Cys-Asn-Lys-Arg-Tyr- Phe-Lys-Leu-Ser-His-Leu-Gln-Met-His-Ser-Arg-Lys), WT1_{332-347} peptide:
                                    (SEQ ID NO: 10)
KRYFKLSHLQMHSRKH (Lys-Arg-Tyr-Phe-Lys-Leu- Ser-His-Leu-Gln-Met-His-Ser-Arg-Lys-His),
and WT1_{328-349} peptide:
                                    (SEQ ID NO: 4)
PGCNKRYFKLSHLQMHSRKHTG (Pro-Gly-Cys-Asn- Lys-Arg-Tyr-Phe-Lys-Leu-Ser-His-Leu-Gln-Met-His- Ser-Arg-Lys-His-Thr-Gly)
```

(patent literatures 3-5). It has not been known if a region of a WT1 helper peptide corresponding to a PFR has any role in differentiation and proliferation of helper T cells or enhancement of function of CTLs.

CITATION LIST

Patent Documents

Patent Literature 1: WO 00/06602
Patent Literature 2: WO 02/079253
Patent Literature 3: WO 2014/357692
Patent Literature 4: WO 2005/045027
Patent Literature 5: WO 2007/047764

Non Patent Documents

Non Patent Literature 1: Clin Cancer Res, 2009; 15 (17); 5323-37
Non Patent Literature 2: Cancer Res, 2002; 62 (22); 6438-6441
Non Patent Literature 3: J Immunother, 2001: 24 (3); 195-204
Non Patent Literature 4: Front Immunol, 2013; 4 (172); 1-9
Non Patent Literature 5: J Immunol, 2001; 166 (11); 6720-6727
Non Patent Literature 6: J Immunol, 2002; 169(2); 739-749
Non Patent Literature 7: Immunity, 1997; 7 (3); 387-399
Non Patent Literature 8: J Immunol, 2006; 176 (5); 2958-2968
Non Patent Literature 9: Proc. Natl. Acad. Sci. USA, 1993; 90 (4); 1227-1231

SUMMARY

Problem to be Solved

An object of the present invention is to provide a cancer vaccine which efficiently induces CTLs.

Solution to Problem

The inventors of the present invention already developed conjugates of cancer antigen peptides from WT1 protein, which conjugates are able to be decomposed to give cancer antigen peptides efficiently. The conjugates are easily be prepared from a variety of cancer antigen peptides, and are highly useful in inducing CTLs. The conjugates were then studied for use in combination with several different WT1 helper peptides. In an extensive study on effects of a wide variety of WT1 peptides in induction of antigen specific immune response, the inventors have newly identified some specific amino acid sequences in WT1 peptides which serve as MHC class II epitopes, and identified some peptides as WT1 helper peptides inducing helper T cells, as disclosed herein. The inventors have also identified combinations of the conjugates and WT1 helper peptides useful as cancer vaccines and finally made the invention.

Accordingly, the present invention includes embodiments described below.

(1) The First Embodiment

1. A partial peptide of WT1 protein consisting of an amino acid sequence of 9 to 30 amino acid residues including a sequence: KLSHL as part thereof or a peptide consisting of an amino acid sequence that differs from the amino acid sequence of the partial peptide by alteration of one or several amino acid residues and having an ability to induce helper T cells, or a pharmaceutically acceptable salt thereof, provided that the peptide is not a peptide consisting of an amino acid sequence selected from:

```
                                      (SEQ ID NO: 10)
KRYFKLSHLQMHSRKH, (SEQ ID NO: 5)
PGCNKRYFKLSHLQMHSRK, (SEQ ID NO: 36)
PGCNKRYFKLSHLQMHSRKH, (SEQ ID NO: 4)
PGCNKRYFKLSHLQMHSRKHTG, (SEQ ID NO: 7)
CNKRYFKLSHLQMHSRK, (SEQ ID NO: 37)
CNKRYFKLSHLQMHSRKH,
and (SEQ ID NO: 38)
CNKRYFKLSHLQMHSRKHTG.
```

2. The peptide or a pharmaceutically acceptable salt thereof of item 1, wherein the peptide consists of an amino acid sequence of 10 to 25 amino acid residues.

3. The peptide or a pharmaceutically acceptable salt thereof of item 2, wherein the peptide consists of an amino acid sequence of 12 to 24 amino acid residues.

4. The peptide or a pharmaceutically acceptable salt thereof of item 3, wherein the peptide consists of an amino acid sequence selected from:

```
                                      (SEQ ID NO: 2)
AYPGCNKRYFKLSHL, (SEQ ID NO: 3)
YPGCNKRYFKLSHLQ, (SEQ ID NO: 6)
GCNKRYFKLSHLQMHSRK, (SEQ ID NO: 8)
NKRYFKLSHLQMHSRK, (SEQ ID NO: 9)
KRYFKLSHLQMHSRK, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG,
and (SEQ ID NO: 14)
KLSHLQMHSRKHTGE,
``` or the peptide consists of an amino acid sequence that differs from the amino acid sequence of the peptide by alteration of one or several amino acid residues.

5. The composition of item 4, wherein the peptide consists of an amino acid sequence of 15 to 22 amino acid residues.

6. The peptide or a pharmaceutically acceptable salt thereof of item 5, wherein the peptide consists of an amino acid sequence selected from:

```
                                      (SEQ ID NO: 2)
AYPGCNKRYFKLSHL, (SEQ ID NO: 3)
YPGCNKRYFKLSHLQ, (SEQ ID NO: 6)
GCNKRYFKLSHLQMHSRK, (SEQ ID NO: 8)
NKRYFKLSHLQMHSRK, (SEQ ID NO: 9)
KRYFKLSHLQMHSRK, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG,
and (SEQ ID NO: 14)
KLSHLQMHSRKHTGE.
```

7. The peptide or a pharmaceutically acceptable salt thereof of item 2, wherein the peptide consists of an amino acid sequence selected from:

```
                                      (SEQ ID NO: 39)
RYFKLSHLQMHSRK, (SEQ ID NO: 40)
YFKLSHLQMHSRK, (SEQ ID NO: 41)
FKLSHLQMHSRK, (SEQ ID NO: 42)
KLSHLQMHSRK, (SEQ ID NO: 43)
AYPGCNKRYFKLSHLQMH, (SEQ ID NO: 44)
AYPGCNKRYFKLSHLQMHSRK, (SEQ ID NO: 45)
RYFKLSHLQMH,
```

-continued

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

KLSHLQMHSRKH, (SEQ ID NO: 50)

YPGCNKRYFKLSHLQMHSRK, (SEQ ID NO: 51)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

NKRYFKLSHL, (SEQ ID NO: 64)

KLSHLQMHSRKHTG, (SEQ ID NO: 65)

KLSHLQMHSRKHT, (SEQ ID NO: 66)

KLSHLQMHSRK, (SEQ ID NO: 67)
and

KLSHLQMHSR, (SEQ ID NO: 68)

or the peptide consists of an amino acid sequence that differs from the amino acid sequence of the peptide by alteration of one or several amino acid residues.

8. The peptide or a pharmaceutically acceptable salt thereof of item 7, wherein the peptide consists of an amino acid sequence selected from:

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

AYPGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

KLSHLQMHSRKH, (SEQ ID NO: 50)

YPGCNKRYFKLSHLQMHSRK, (SEQ ID NO: 51)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

```
                          (SEQ ID NO: 64)
NKRYFKLSHL, (SEQ ID NO: 65)
KLSHLQMHSRKHTG, (SEQ ID NO: 66)
KLSHLQMHSRKHT, (SEQ ID NO: 67)
KLSHLQMHSRK,
and (SEQ ID NO: 68)
KLSHLQMHSR.
```

9. The peptide or a pharmaceutically acceptable salt thereof of item 2, wherein the peptide comprises an amino acid sequence selected from:

```
                          (SEQ ID NO: 2)
AYPGCNKRYFKLSHL, (SEQ ID NO: 3)
YPGCNKRYFKLSHLQ, (SEQ ID NO: 6)
GCNKRYFKLSHLQMHSRK, (SEQ ID NO: 8)
NKRYFKLSHLQMHSRK, (SEQ ID NO: 9)
KRYFKLSHLQMHSRK, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG, (SEQ ID NO: 14)
KLSHLQMHSRKHTGE, (SEQ ID NO: 39)
RYFKLSHLQMHSRK, (SEQ ID NO: 40)
YFKLSHLQMHSRK, (SEQ ID NO: 41)
FKLSHLQMHSRK, (SEQ ID NO: 42)
KLSHLQMHSRK, (SEQ ID NO: 43)
AYPGCNKRYFKLSHLQMH, (SEQ ID NO: 44)
AYPGCNKRYFKLSHLQMHSRK, (SEQ ID NO: 45)
RYFKLSHLQMH, (SEQ ID NO: 46)
GCNKRYFKLSHL, (SEQ ID NO: 47)
FKLSHLQMHSRKHTGE, (SEQ ID NO: 48)
RYFKLSHLQMHSRKHT, (SEQ ID NO: 49)
RYFKLSHLQMHSRKHTGE, (SEQ ID NO: 50)
KLSHLQMHSRKH, (SEQ ID NO: 51)
YPGCNKRYFKLSHLQMHSRK, (SEQ ID NO: 52)
AYPGCNKRYFKLSHLQMHSR, (SEQ ID NO: 53)
AYPGCNKRYFKLSHLQMHS, (SEQ ID NO: 54)
AYPGCNKRYFKLSHLQM, (SEQ ID NO: 55)
AYPGCNKRYFKLSHLQ, (SEQ ID NO: 56)
YFKLSHLQMHSRKHTGE, (SEQ ID NO: 57)
RYFKLSHLQMHSRKHTG, (SEQ ID NO: 58)
RYFKLSHLQMHSR, (SEQ ID NO: 59)
RYFKLSHLQMHS, (SEQ ID NO: 60)
RYFKLSHLQM, (SEQ ID NO: 61)
YPGCNKRYFKLSHL, (SEQ ID NO: 62)
PGCNKRYFKLSHL, (SEQ ID NO: 63)
CNKRYFKLSHL, (SEQ ID NO: 64)
NKRYFKLSHL, (SEQ ID NO: 65)
KLSHLQMHSRKHTG, (SEQ ID NO: 66)
KLSHLQMHSRKHT, (SEQ ID NO: 67)
KLSHLQMHSRK,
and (SEQ ID NO: 68)
KLSHLQMHSR.
```

10. The peptide or a pharmaceutically acceptable salt thereof of item 6, wherein the peptide consists of the amino acid sequence:

```
                          (SEQ ID NO: 2)
     AYPGCNKRYFKLSHL.
```

11. The peptide or a pharmaceutically acceptable salt thereof of item 6, wherein the peptide consists of the amino acid sequence:

```
                          (SEQ ID NO: 3)
     YPGCNKRYFKLSHLQ.
```

12. The peptide or a pharmaceutically acceptable salt thereof of item 6, wherein the peptide consists of the amino acid sequence:

GCNKRYFKLSHLQMHSRK. (SEQ ID NO: 6)

13. The peptide or a pharmaceutically acceptable salt thereof of item 6, wherein the peptide consists of the amino acid sequence:

NKRYFKLSHLQMHSRK. (SEQ ID NO: 8)

14. The peptide or a pharmaceutically acceptable salt thereof of item 6, wherein the peptide consists of the amino acid sequence:

KRYFKLSHLQMHSRK. (SEQ ID NO: 9)

15. The peptide or a pharmaceutically acceptable salt thereof of item 6, wherein the peptide consists of the amino acid sequence:

RYFKLSHLQMHSRKH. (SEQ ID NO: 11)

16. The peptide or a pharmaceutically acceptable salt thereof of item 6, wherein the peptide consists of the amino acid sequence:

YFKLSHLQMHSRKHT. (SEQ ID NO: 12)

17. The peptide or a pharmaceutically acceptable salt thereof of item 6, wherein the peptide consists of the amino acid sequence:

FKLSHLQMHSRKHTG. (SEQ ID NO: 13)

18. The peptide or a pharmaceutically acceptable salt thereof of item 6, wherein the peptide consists of the amino acid sequence:

KLSHLQMHSRKHTGE. (SEQ ID NO: 14)

19. The peptide or a pharmaceutically acceptable salt thereof of item 8, wherein the peptide consists of the amino acid sequence:

RYFKLSHLQMHSRK. (SEQ ID NO: 39)

20. The peptide or a pharmaceutically acceptable salt thereof of item 8, wherein the peptide consists of the amino acid sequence:

AYPGCNKRYFKLSHLQMH. (SEQ ID NO: 43)

21. The peptide or a pharmaceutically acceptable salt thereof of item 8, wherein the peptide consists of the amino acid sequence:

AYPGCNKRYFKLSHLQMHSRK. (SEQ ID NO: 44)

22. The peptide or a pharmaceutically acceptable salt thereof of item 8, wherein the peptide consists of the amino acid sequence:

RYFKLSHLQMH. (SEQ ID NO: 45)

23. The peptide or a pharmaceutically acceptable salt thereof of item 8, wherein the peptide consists of the amino acid sequence:

GCNKRYFKLSHL. (SEQ ID NO: 46)

24. The peptide or a pharmaceutically acceptable salt thereof of item 8, wherein the peptide consists of the amino acid sequence:

RYFKLSHLQMHSRKHT. (SEQ ID NO: 48)

25. The peptide or a pharmaceutically acceptable salt thereof of item 8, wherein the peptide consists of the amino acid sequence:

RYFKLSHLQMHSRKHTGE. (SEQ ID NO: 49)

26. The peptide or a pharmaceutically acceptable salt thereof of any one of items 1-25, wherein the peptide induces helper T cells by binding to an MHC class II molecule selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQBL*0401, DQB1*0501, DQB1*0601, DQB1*0602 and DRB5*0102.

27. The peptide or a pharmaceutically acceptable salt thereof of item 26, wherein the peptide induces of helper T cells by binding to an MHC class II molecule selected from the group consisting of DRB1*0101, DRB1*0405, DRB11502, DPB1*0201, DPB1*0202 and DQB1*0601.

28. A polynucleotide encoding the peptide of any one of items 1-27.

29. An expression vector comprising the polynucleotide of item 28.

30. An antibody against the peptide or a pharmaceutically acceptable salt thereof of any one of items 1-27 or the polynucleotide of item 28.

31. A pharmaceutical composition for treatment or prevention of a cancer, wherein the composition comprises the peptide or a pharmaceutically acceptable salt thereof of any one of items 1-27, the polynucleotide of item 28, or the vector of item 29.

32. The pharmaceutical composition of item 31, wherein the composition comprises the peptide or a pharmaceutically acceptable salt thereof of any one of items 1-27.

33. The pharmaceutical composition of item 31 or 32, wherein the composition is used in combination with an immunomodulator.

34. The pharmaceutical composition of item 33, wherein the immunomodulator is an immune checkpoint inhibitor.

35. A method of treating or preventing a cancer, comprising administering to a subject a therapeutically or prophylactically effective amount of the peptide or a pharmaceutically acceptable salt thereof of any one of items 1-27, the polynucleotide of item 28, or the vector of item 29.

36. The method of item 35, wherein the subject has an MHC class II molecule as described in item 26 or 27.

37. Use of the peptide or a pharmaceutically acceptable salt thereof of any one of items 1-27, the polynucleotide of item 28, or the vector of item 29 for the manufacture of a medicament for treatment of prevention of a cancer.

38. An antigen presenting cell, wherein the cell presents the peptide of any one of items 1-27 on the cell via an MHC class II molecule.

39. A method of inducing antigen presenting cells, comprising culturing immature antigen presenting cells in the presence of the peptide of any one of items 1-27, and inducing antigen presenting cells that present the peptide on the cells via an MHC class II molecule from the immature antigen presenting cells.

40. A WT1-specific helper T cell induced by the peptide of any one of items 1-27.

41. A method of inducing WT1-specific helper T cells, comprising culturing peripheral blood mononuclear cells in the presence of the peptide of any one of items 1-27, and inducing WT1-specific helper T cells from the peripheral blood mononuclear cells.

42. A kit for inducing antigen presenting cells or WT1-specific helper T cells, wherein the kit comprises as a component the peptide or a pharmaceutically acceptable salt thereof of any one of items 1-27.

43. A kit for preventing or treating a cancer, wherein the kit comprises as a component the peptide or a pharmaceutically acceptable salt thereof of any one of items 1-27, the polynucleotide of item 28, or the vector of item 29.

44. A method of determining presence or amount of WT1-specific helper T cells in a subject, comprising the steps of:
(a) contacting a sample from the subject with the peptide of any one of items 1-27; and
(b) determining presence or amount of a cytokine in the sample.

45. The method of item 44, wherein the subject has an MHC class II molecule as described in item 26 or 27.

46. A composition comprising the peptide or a pharmaceutically acceptable salt thereof of any one of items 1-27, wherein the peptide or a pharmaceutically acceptable salt thereof is used in combination with a compound of formula (I):

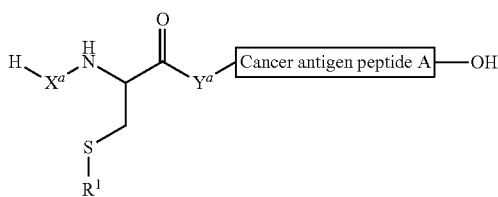

wherein,
$X^a$ and $Y^a$ independently represent a single bond or a divalent peptide group consisting of 1 to 4 amino acid residues, provided that the sum of the number of amino acid residues in $X^a$ and $Y^a$ is an integer of 0 to 4;

cancer antigen peptide A is a peptide consisting of 7 to 30 amino acid residues, wherein the cancer antigen peptide A binds to $Y^a$ and OH shown in formula (I) via its N-terminal amino group and C-terminal carbonyl group, respectively; and $R^1$ is hydrogen, a group of formula (2):

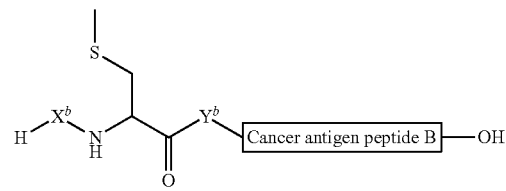

(wherein
$X^b$ and $Y^b$ independently represent a single bond or a divalent peptide group consisting of 1 to 4 amino acid residues, provided that the sum of the number of amino acid residues in $X^b$ and $Y^b$ is an integer of 0 to 4;

cancer antigen peptide B is a peptide consisting of 7 to 30 amino acid residues, wherein the cancer antigen peptide B binds to $Y^b$ and OH shown in formula (2) via its N-terminal amino group and C-terminal carbonyl group, respectively, provided that cancer antigen peptide B has a different amino acid sequence from antigen peptide A; and the thioether group in formula (2) binds to the thioether group in formula (1)), or cancer antigen peptide C, wherein the cancer antigen peptide C is a peptide consisting of 7 to 30 amino acid residues including one cysteine residue, provided that the cancer antigen peptide C has a different amino acid sequence from the cancer antigen peptide A, and wherein a thioether group of a cysteine residue of the cancer antigen peptide C binds to the thioether group in formula (1), provided that, when $R^1$ is hydrogen, the compound of formula (1) is not a partial peptide of WT1 protein;
or a pharmaceutically acceptable salt thereof.

47. The composition of item 46, wherein the peptide or a pharmaceutically acceptable salt thereof and the compound of formula (1) or a pharmaceutically acceptable salt thereof are formulated in separate compositions.

48. The composition of item 46, wherein the peptide or a pharmaceutically acceptable salt thereof and the compound of formula (1) or a pharmaceutically acceptable salt thereof are incorporated in a single composition.

49. The composition of any one of items 46-48, wherein the compound of formula (1) has a divalent peptide group consisting of two amino acid residues as $X^a$ and a single bond as $Y^a$; a divalent peptide group consisting of one amino acid residue as each of $X^a$ and $Y^a$ independently; a single bond as $X^a$ and a divalent peptide group consisting of two amino acid residues as $Y^a$; a divalent peptide group consisting of one amino acid residue as $X^a$ and a single bond as $Y^a$; a single bond as $X^a$ and a divalent peptide group consisting of one amino acid residue as $Y^a$; or a single bond as $X^a$ or $Y^a$.

50. The composition of item 49, wherein the compound of formula (1) has a divalent peptide group consisting of one amino acid residue as $X^a$ and a single bond as $Y^a$; a single bond as $X^a$ and a divalent peptide group consisting of one amino acid residue as $Y^a$; or a single bond as $X^a$ or $Y^a$.

51. The composition of item 50, wherein $X^a$ is a single bond or a residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, and $Y^a$ is a single bond.

52. The composition of item 51, wherein $X^a$ is a single bond or a residue of alanine, leucine, or methionine, and $Y^a$ is a single bond.

53. The composition of item 52, wherein $X^a$ and $Y^a$ are both single bonds.

54. The composition of any one of items 46-53, wherein the cancer antigen peptide A is a peptide consisting of 7 to 15 amino acid residues.

55. The composition of item 54, wherein the cancer antigen peptide A is a peptide comprising an amino acid sequence selected from:

RMFPNAPYL, (SEQ ID NO: 15)

CMTWNQMNL, (SEQ ID NO: 16)

ALLPAVPSL, (SEQ ID NO: 18)

SLGEQQYSV, (SEQ ID NO: 19)

RVPGVAPTL, (SEQ ID NO: 20)
and

VLDFAPPGA, (SEQ ID NO: 21)

or a peptide comprising an amino acid sequence that differs from the amino acid sequence selected from SEQ ID NOS: 15, 16, 18, 19, 20 and 21 by alteration of one or several amino acid residues.

56. The composition of item 55, wherein the cancer antigen peptide A is a peptide consisting of an amino acid sequence selected from:

RMFPNAPYL, (SEQ ID NO: 15)

CMTWNQMNL, (SEQ ID NO: 16)

CYTWNQMNL, (SEQ ID NO: 17)

ALLPAVPSL, (SEQ ID NO: 18)

SLGEQQYSV, (SEQ ID NO: 19)

RVPGVAPTL, (SEQ ID NO: 20)
and

VLDFAPPGA. (SEQ ID NO: 21)

57. The composition of item 56, wherein the cancer antigen peptide A consists of the amino acid sequence:

RMFPNAPYL. (SEQ ID NO: 15)

58. The composition of any one of items 46-57, wherein the compound of formula (1) has a divalent peptide group consisting of two amino acid residues as $X^b$ and a single bond as $Y^b$; a divalent peptide group consisting of one amino acid residue as each of $X^b$ and $Y^b$ independently; a single bond as $X^b$ and a divalent peptide group consisting of two amino acid residues as $Y^b$; a divalent peptide group consisting of one amino acid residue as $X^b$ and a single bond as $Y^b$; a single bond as $X^b$ and a divalent peptide group consisting of one amino acid residue as $Y^b$; or a single bond as $X^b$ or $Y^b$, 59. The composition of item 58, wherein the compound of formula (1) has a divalent peptide group consisting of one amino acid residue as $X^b$ and a single bond as $Y^b$; a single bond as $X^b$ and a divalent peptide group consisting of one amino acid residue as $Y^b$; or a single bond as $X^b$ or $Y^b$.

60. The composition of item 59, wherein $X^b$ is a single bond or a residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, and $Y^b$ is a single bond.

61. The composition of item 60, wherein $X^b$ is a single bond or a residue of alanine, leucine, or methionine, and $Y^b$ is a single bond.

62. The composition of item 61, wherein $X^b$ and $Y^b$ are both single bonds.

63. The composition of any one of items 46-62, wherein the cancer antigen peptide B is a peptide consisting of 7 to 15 amino acid residues.

64. The composition of item 63, wherein the cancer antigen peptide B is a peptide comprising an amino acid sequence selected from:

RMFPNAPYL, (SEQ ID NO: 15)

CMTWNQMNL, (SEQ ID NO: 16)

ALLPAVPSL, (SEQ ID NO: 18)

SLGEQQYSV, (SEQ ID NO: 19)

RVPGVAPTL, (SEQ ID NO: 20)
and

VLDFAPPGA, (SEQ ID NO: 21)

or a peptide comprising an amino acid sequence that differs from the amino acid sequence selected from SEQ ID NOS: 15, 16, 18, 19, 20 and 21 by alteration of one or several amino acid residues.

65. The composition of item 64, wherein the cancer antigen peptide B is a peptide consisting of an amino acid sequence selected from:

RMFPNAPYL, (SEQ ID NO: 15)

CMTWNQMNL, (SEQ ID NO: 16)

CYTWNQMNL, (SEQ ID NO: 17)

```
                                   (SEQ ID NO: 18)
ALLPAVPSL,
                                   (SEQ ID NO: 19)
SLGEQQYSV,
                                   (SEQ ID NO: 20)
RVPGVAPTL,
and
                                   (SEQ ID NO: 21)
VLDFAPPGA.
```

66. The composition of any one of items 46-65, wherein the cancer antigen peptide C is a peptide consisting of 7 to 15 amino acid residues.

67. The composition of item 66, wherein the cancer antigen peptide C is a peptide consisting of an amino acid sequence selected from:

```
                                   (SEQ ID NO: 16)
CMTWNQMNL,
and
                                   (SEQ ID NO: 17)
CYTWNQMNL.
```

68. The composition of item 67, wherein the cancer antigen peptide C consists of the amino acid sequence:

```
                                   (SEQ ID NO: 16)
CMTWNQMNL.
```

69. The composition of item 67, wherein the cancer antigen peptide C consists of the amino acid sequence:

```
                                   (SEQ ID NO: 17)
CYTWNQMNL.
```

70. The composition of any one of items 46-68, wherein the compound of formula (1) or a pharmaceutically acceptable salt thereof is the compound of formula (3):

```
CRMFPNAPYL    (SEQ ID NO: 35),        (3)
|
CMTWNQMNL     (SEQ ID NO: 16)
``` wherein C—C shown in the formula means that the C residues are linked together by a disulfide bond, or a pharmaceutically acceptable salt thereof.

71. The composition of any one of items 46-67 and 69, wherein the compound of formula (1) or a pharmaceutically acceptable salt thereof is the compound of formula (4):

```
CRMFPNAPYL    (SEQ ID NO: 35),        (4)
|
CYTWNQMNL     (SEQ ID NO: 17)
``` wherein C—C shown in the formula means that the C residues are linked together by a disulfide bond, or a pharmaceutically acceptable salt thereof.

72. A pharmaceutical composition comprising the composition of any one of items 46-71 and a pharmaceutically acceptable carrier.

73. The pharmaceutical composition of item 72, wherein the pharmaceutical composition is for use as a cancer vaccine.

74. The composition of any one of items 46-71, wherein the composition is for use in treatment or prevention of a cancer.

75. Use of the composition of any one of items 46-71 for the manufacture of a cancer vaccine.

76. A method of treating or preventing a cancer, comprising administering to a patient in need thereof a therapeutically or prophylactically effective amount of the composition of any one of items 46-71.

77. The method of item 76, wherein the patient is WT1-positive.

78. The pharmaceutical composition, the composition, the use, or the method of any one of item 71-77, wherein the cancer is selected from the group consisting of leukemia, myelodysplastic syndrome, multiple myeloma, malignant lymphoma, gastric cancer, colorectal cancer, lung cancer, breast cancer, germ cell cancer, liver cancer, skin cancer, urinary bladder cancer, prostate cancer, uterine cancer, cervical cancer, ovarian cancer, brain tumor, bone cancer, pancreatic cancer, cancer of the head or neck, cutaneous or intraocular malignant melanoma, rectal cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia such as acute myeloid leukemia, chronic myeloid leukemia, acute lymphoblastic leukemia, or chronic lymphocytic leukemia, childhood solid tumor, lymphocytic lymphoma, cancer of the kidney or ureter, carcinoma of the renal pelvis, central nervous system (CNS) tumor, primary CNS lymphoma, tumor angiogenesis, spinal tumor, brainstem glioma, pituitary adenoma, Kaposi's sarcoma, epidermoid cancer, squamous cell cancer, T-cell lymphoma, glioblastoma multiforme, malignant melanoma, non-small cell lung cancer, renal cell carcinoma, and asbestos-induced cancer.

79. The pharmaceutical composition, the composition, the use, or the method of any one of item 46-78, wherein the peptide or a pharmaceutically acceptable salt thereof is used in combination further with an immunomodulator.

80. The pharmaceutical composition, the composition, the use, or the method of item 79, wherein the immunomodulator is an immune checkpoint inhibitor.

(2) The Second Embodiment

1. A composition comprising a compound of formula (1):

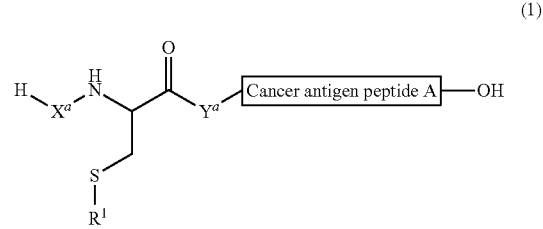

wherein $X^a$ and $Y^a$ independently represent a single bond or a divalent peptide group consisting of 1 to 4 amino acid residues, provided that the sum of the number of amino acid residues in $X^a$ and $Y^a$ is an integer of 0 to 4;

cancer antigen peptide A is a peptide consisting of 7 to 30 amino acid residues, wherein the cancer antigen peptide A binds to $Y^a$ and OH shown in formula (1) via its N-terminal amino group and C-terminal carbonyl group, respectively; and $R^1$ is hydrogen, or a group of formula (2):

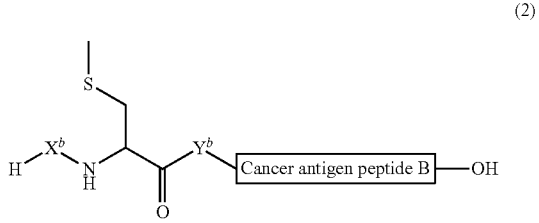

(2)

(wherein
$X^b$ and $Y^b$ independently represent a single bond or a divalent peptide group consisting of 1 to 4 amino acid residues, provided that the sum of the number of amino acid residues in $X^b$ and $Y^b$ is an integer of 0 to 4;

cancer antigen peptide B is a peptide consisting of 7 to 30 amino acid residues, provided that the cancer antigen peptide B has a different amino acid sequence from the cancer antigen peptide A, wherein the cancer antigen peptide B binds to $Y^b$ and OH shown in formula (2) via its N-terminal amino group and C-terminal carbonyl group, respectively; and the thioether group in formula (2) binds to the thioether group in formula (1)), provided that, when $R^1$ is hydrogen, the compound of formula (1) is not a partial peptide of WT1 protein;

or a pharmaceutically acceptable salt thereof, wherein the compound of formula (I) or a pharmaceutically acceptable salt thereof is used in combination with cancer antigen peptide D or a pharmaceutically acceptable salt thereof, wherein the cancer antigen peptide D is a partial peptide of WT1 protein consisting of an amino acid sequence of 9 to 30 amino acid residues including a sequence: KLSHL as part thereof or a peptide consisting of an amino acid sequence that differs from the amino acid sequence of the partial peptide by alteration of one or several amino acid residues, or a pharmaceutically acceptable salt thereof, provided that, when the compound of formula (1) is the compound of formula (4), the cancer antigen peptide D is neither SEQ ID NO: 7 nor SEQ ID NO: 38.

2. The composition of item 1, wherein the compound of formula (1) or a pharmaceutically acceptable salt thereof and the peptide or a pharmaceutically acceptable salt thereof are formulated in separate compositions.

3. The composition of item 1, wherein the compound of formula (1) or a pharmaceutically acceptable salt thereof and the peptide or a pharmaceutically acceptable salt thereof are incorporated in a single composition.

4. The composition of any one of items 1-3, wherein the compound of formula (1) has a divalent peptide group consisting of two amino acid residues as $X^a$ and a single bond as $Y^a$; a divalent peptide group consisting of one amino acid residue as each of $X^a$ and $Y^a$ independently; a single bond as $X^a$ and a divalent peptide group consisting of two amino acid residues as $Y^a$; a divalent peptide group consisting of one amino acid residue as $X^a$ and a single bond as $Y^a$; a single bond as $X^a$ and a divalent peptide group consisting of one amino acid residue as $Y^a$; or a single bond as $X^a$ or $Y^a$.

5. The composition of item 4, wherein the compound of formula (1) has a divalent peptide group consisting of one amino acid residue as $X^a$ and a single bond as $Y^a$; a single bond as $X^a$ and a divalent peptide group consisting of one amino acid residue as $Y^a$; or a single bond as $X^a$ or $Y^a$.

6. The composition of item 5, wherein $X^a$ is a single bond or a residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, and $Y^a$ is a single bond.

7. The composition of item 6, wherein $X^a$ is a single bond or a residue of alanine, leucine, or methionine, and $Y^a$ is a single bond.

8. The composition of item 7, wherein $X^a$ and $Y^a$ are both single bonds.

9. The composition of any one of items 1-8, wherein the cancer antigen peptide A is a peptide consisting of 7 to 15 amino acid residues.

10. The composition of any one of items 1-9, wherein the cancer antigen peptide A is a peptide comprising an amino acid sequence selected from:

RMFPNAPYL, (SEQ ID NO: 15)

CMTWNQMNL, (SEQ ID NO: 16)

ALLPAVPSL, (SEQ ID NO: 18)

SLGEQQYSV, (SEQ ID NO: 19)

RVPGVAPTL, (SEQ ID NO: 20)
and

VLDFAPPGA, (SEQ ID NO: 21)

or a peptide comprising an amino acid sequence that differs from the amino acid sequence selected from SEQ ID NOS: 15, 16, 18, 19, 20 and 21 by alteration of one or several amino acid residues.

11. The composition of item 10, wherein the cancer antigen peptide A is a peptide consisting of an amino acid sequence selected from:

RMFPNAPYL, (SEQ ID NO: 15)

CMTWNQMNL, (SEQ ID NO: 16)

CYTWNQMNL, (SEQ ID NO: 17)

ALLPAVPSL, (SEQ ID NO: 18)

SLGEQQYSV, (SEQ ID NO: 19)

RVPGVAPTL, (SEQ ID NO: 20)
and

VLDFAPPGA. (SEQ ID NO: 21)

12. The composition of item 11, wherein the cancer antigen peptide A consists of the amino acid sequence:

RMFPNAPYL. (SEQ ID NO: 15)

13. The composition of any one of items 1-12, wherein the compound of formula (1) has a divalent peptide group consisting of two amino acid residues as $X^b$ and a single bond as $Y^b$; a divalent peptide group consisting of one amino acid residue as each of $X^b$ and $Y^b$ independently; a single bond as $X^b$ and a divalent peptide group consisting of two amino acid residues as $Y^b$; a divalent peptide group consisting of one amino acid residue as $X^b$ and a single bond as $Y^b$; a single bond as $X^b$ and a divalent peptide group consisting of one amino acid residue as $Y^b$; or a single bond as $X^b$ or $Y^b$.

14. The composition of item 13, wherein the compound of formula (1) has a divalent peptide group consisting of one amino acid residue as $X^b$ and a single bond as $Y^b$; a single bond as $X^b$ and a divalent peptide group consisting of one amino acid residue as $Y^b$; or a single bond as $X^b$ or $Y^b$.

15. The composition of item 14, wherein $X^b$ is a single bond or a residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, and $Y^b$ is a single bond.

16. The composition of item 15, wherein $X^b$ is a single bond or a residue of alanine, leucine, or methionine, and $Y^b$ is a single bond.

17. The composition of item 16, wherein $X^b$ is a residue of alanine, and $Y^b$ is a single bond.

18. The composition of item 16, wherein $X^b$ is a residue of leucine, and $Y^b$ is a single bond.

19. The composition of item 16, wherein $X^b$ is a residue of methionine, and $Y^b$ is a single bond.

20. The composition of any one of items 1-19, wherein the cancer antigen peptide B is a peptide consisting of 7 to 15 amino acid residues.

21. The composition of item 20, wherein the cancer antigen peptide B is a peptide comprising an amino acid sequence selected from:

RMFPNAPYL, (SEQ ID NO: 15)

CMTWNQMNL, (SEQ ID NO: 16)

ALLPAVPSL, (SEQ ID NO: 18)

SLGEQQYSV, (SEQ ID NO: 19)

RVPGVAPTL, (SEQ ID NO: 20)
and

VLDFAPPGA, (SEQ ID NO: 21)

or a peptide comprising an amino acid sequence that differs from the amino acid sequence selected from SEQ ID NOS: 15, 16, 18, 19, 20 and 21 by alteration of one or several amino acid residues.

22. The composition of item 21, wherein the cancer antigen peptide B is a peptide consisting of an amino acid sequence selected from:

RMFPNAPYL, (SEQ ID NO: 15)

CMTWNQMNL, (SEQ ID NO: 16)

CYTWNQMNL, (SEQ ID NO: 17)

ALLPAVPSL, (SEQ ID NO: 18)

SLGEQQYSV, (SEQ ID NO: 19)

RVPGVAPTL, (SEQ ID NO: 20)
and

VLDFAPPGA. (SEQ ID NO: 21)

23. The composition of any one of items 1-22, wherein the cancer antigen peptide D is a peptide consisting of an amino acid sequence of 10 to 25 amino acid residues.

24. The composition of item 23, wherein the cancer antigen peptide D is a peptide consisting of an amino acid sequence of 12 to 24 amino acid residues.

25. The composition of item 24, wherein the cancer antigen peptide D is a peptide consisting of an amino acid sequence selected from:

AYPGCNKRYFKLSHL, (SEQ ID NO: 2)

YPGCNKRYFKLSHLQ, (SEQ ID NO: 3)

PGCNKRYFKLSHLQMHSRKHTG, (SEQ ID NO: 4)

PGCNKRYFKLSHLQMHSRK, (SEQ ID NO: 5)

GCNKRYFKLSHLQMHSRK, (SEQ ID NO: 6)

CNKRYFKLSHLQMHSRK, (SEQ ID NO: 7)

NKRYFKLSHLQMHSRK, (SEQ ID NO: 8)

KRYFKLSHLQMHSRK, (SEQ ID NO: 9)

KRYFKLSHLQMHSRKH, (SEQ ID NO: 10)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)
and

KLSHLQMHSRKHTGE, (SEQ ID NO: 14)

or a peptide consisting of an amino acid sequence that differs from the amino acid sequence of the peptide by alteration of one or several amino acid residues.

26. The composition of item 25, wherein the cancer antigen peptide D is a peptide consisting of an amino acid sequence selected from:

AYPGCNKRYFKLSHL, (SEQ ID NO: 2)

YPGCNKRYFKLSHLQ, (SEQ ID NO: 3)

PGCNKRYFKLSHLQMHSRKHTG, (SEQ ID NO: 4)

PGCNKRYFKLSHLQMHSRK, (SEQ ID NO: 5)

GCNKRYFKLSHLQMHSRK, (SEQ ID NO: 6)

NKRYFKLSHLQMHSRK, (SEQ ID NO: 8)

KRYFKLSHLQMHSRK, (SEQ ID NO: 9)

KRYFKLSHLQMHSRKH, (SEQ ID NO: 10)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)
and

KLSHLQMHSRKHTGE, (SEQ ID NO: 14)

or a peptide consisting of an amino acid sequence that differs from the amino acid sequence of the peptide by alteration of one or several amino acid residues.

27. The composition of item 26, wherein the cancer antigen peptide D is a peptide consisting of an amino acid sequence selected from:

AYPGCNKRYFKLSHL, (SEQ ID NO: 2)

YPGCNKRYFKLSHLQ, (SEQ ID NO: 3)

GCNKRYFKLSHLQMHSRK, (SEQ ID NO: 6)

NKRYFKLSHLQMHSRK, (SEQ ID NO: 8)

KRYFKLSHLQMHSRK, (SEQ ID NO: 9)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)
and

KLSHLQMHSRKHTGE, (SEQ ID NO: 14)

or a peptide consisting of an amino acid sequence that differs from the amino acid sequence of the peptide by alteration of one or several amino acid residues.

28. The composition of item 25, wherein the cancer antigen peptide D is a peptide consisting of an amino acid sequence of 15 to 22 amino acid residues.

29. The composition of item 28, wherein the cancer antigen peptide D is a peptide consisting of an amino acid sequence selected from:

AYPGCNKRYFKLSHL, (SEQ ID NO: 2)

YPGCNKRYFKLSHLQ, (SEQ ID NO: 3)

PGCNKRYFKLSHLQMHSRKHTG, (SEQ ID NO: 4)

PGCNKRYFKLSHLQMHSRK, (SEQ ID NO: 5)

GCNKRYFKLSHLQMHSRK, (SEQ ID NO: 6)

CNKRYFKLSHLQMHSRK, (SEQ ID NO: 7)

NKRYFKLSHLQMHSRK, (SEQ ID NO: 8)

KRYFKLSHLQMHSRK, (SEQ ID NO: 9)

KRYFKLSHLQMHSRKH, (SEQ ID NO: 10)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)
and

KLSHLQMHSRKHTGE. (SEQ ID NO: 14)

30. The composition of item 29, wherein the cancer antigen peptide D is a peptide consisting of an amino acid sequence selected from:

AYPGCNKRYFKLSHL, (SEQ ID NO: 2)

YPGCNKRYFKLSHLQ, (SEQ ID NO: 3)

PGCNKRYFKLSHLQMHSRKHTG, (SEQ ID NO: 4)

PGCNKRYFKLSHLQMHSRK, (SEQ ID NO: 5)

GCNKRYFKLSHLQMHSRK, (SEQ ID NO: 6)

NKRYFKLSHLQMHSRK, (SEQ ID NO: 8)

KRYFKLSHLQMHSRK, (SEQ ID NO: 9)

KRYFKLSHLQMHSRKH, (SEQ ID NO: 10)

RYFKLSHLQMHSRKH, (SEQ ID NO: 11)

YFKLSHLQMHSRKHT, (SEQ ID NO: 12)

-continued

FKLSHLMHSRKHTG, (SEQ ID NO: 13)
and

KLSHLQMHSRKHTGE. (SEQ ID NO: 14)

31. The composition of item 30, wherein the cancer antigen peptide D is a peptide consisting of an amino acid sequence selected from:

AYPGCNKRYFKLSHL, (SEQ ID NO: 2)

YPGCNKRYFKLSHLQ, (SEQ ID NO: 3)

GCNKRYFKLSHLQMHSRK, (SEQ ID NO: 6)

NKRYFKLSHLQMHSRK, (SEQ ID NO: 8)

KRYFKLSHLQMHSRK, (SEQ ID NO: 9)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)
and

KLSHLQMHSRKHTGE. (SEQ ID NO: 14)

32. The composition of item 23, wherein the cancer antigen peptide D is a peptide consisting of an amino acid

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

AYPGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

KLSHLQMHSRKH, (SEQ ID NO: 50)

YPGCNKRYFKLSHLQMHSRK, (SEQ ID NO: 51)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

NKRYFKLSHL, (SEQ ID NO: 64)

KLSHLQMHSRKHTG, (SEQ ID NO: 65)

KLSHLQMHSRKHT, (SEQ ID NO: 66)

KLSHLQMHSRK, (SEQ ID NO: 67)
and

KLSHLQMHSR, (SEQ ID NO: 68)

or a peptide consisting of an amino acid sequence that differs from the amino acid sequence of the peptide by alteration of one or several amino acid residues.

33. The composition of item 32, wherein the cancer antigen peptide D is a peptide consisting of an amino acid sequence selected from:

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

-continued

AYPGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

KLSHLQMHSRKH, (SEQ ID NO: 50)

YPGCNKRYFKLSHLQMHSRK, (SEQ ID NO: 51)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

NKRYFKLSHL, (SEQ ID NO: 64)

KLSHLQMHSRKHTG, (SEQ ID NO: 65)

KLSHLQMHSRKHT, (SEQ ID NO: 66)

KLSHLQMHSRK,
and (SEQ ID NO: 67)

KLSHLQMHSR. (SEQ ID NO: 68)

34. The composition of item 23, wherein the cancer antigen peptide D is a peptide comprising an amino acid sequence selected from:

AYPGCNKRYFKLSHL, (SEQ ID NO: 2)

YPGCNKRYFKLSHLQ, (SEQ ID NO: 3)

GCNKRYFKLSHLQMHSRK, (SEQ ID NO: 6)

NKRYFKLSHLQMHSRK, (SEQ ID NO: 8)

KRYFKLSHLQMHSRK, (SEQ ID NO: 9)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)

KLSHLQMHSRKHTGE, (SEQ ID NO: 14)

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

AYPGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

KLSHLQMHSRKH, (SEQ ID NO: 50)

YPGCNKRYFKLSHLQMHSHK, (SEQ ID NO: 51)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

-continued

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

NKRYFKLSHL, (SEQ ID NO: 64)

KLSHLQMHSRKHTG, (SEQ ID NO: 65)

KLSHLQMHSRKHT, (SEQ ID NO: 66)

KLSHLQMHSRK, (SEQ ID NO: 67)
and

KLSHLQMHSR. (SEQ ID NO: 68)

35. The composition of item 29, wherein the cancer antigen peptide D consists of the amino acid sequence:

AYPGCNKRYFKLSHL. (SEQ ID NO: 2)

36. The composition of item 29, wherein the cancer antigen peptide D consists of the amino acid sequence:

YPGCNKRYFKLSHLQ. (SEQ ID NO: 3)

37. The composition of item 29, wherein the cancer antigen peptide D consists of the amino acid sequence:

PGCNKRYFKLSHLQMHSRKHTG. (SEQ ID NO: 4)

38. The composition of item 29, wherein the cancer antigen peptide D consists of the amino acid sequence:

PGCNKRYFKLSHLQMHSRK. (SEQ ID NO: 5)

39. The composition of item 29, wherein the cancer antigen peptide D consists of the amino acid sequence:

GCNKRYFKLSHLQMHSRK. (SEQ ID NO: 6)

40. The composition of item 29, wherein the cancer antigen peptide D consists of the amino acid sequence:

CNKRYFKLSHLQMHSRK. (SEQ ID NO: 7)

41. The composition of item 29, wherein the cancer antigen peptide D consists of the amino acid sequence:

NKRYFKLSHLQMHSRK. (SEQ ID NO: 8)

42. The composition of item 29, wherein the cancer antigen peptide D consists of the amino acid sequence:

KRYFKLSHLQMHSRK. (SEQ ID NO: 9)

43. The composition of item 29, wherein the cancer antigen peptide D consists of the amino acid sequence:

KRYFKLSHLQMHSRKH. (SEQ ID NO: 10)

44. The composition of item 29, wherein the cancer antigen peptide D consists of the amino acid sequence:

RYFKLSHLQMHSRKH. (SEQ ID NO: 11)

45. The composition of item 29, wherein the cancer antigen peptide D consists of the amino acid sequence:

YFKLSHLQMHSRKHT. (SEQ ID NO: 12)

46. The composition of item 29, wherein the cancer antigen peptide D consists of the amino acid sequence:

FKLSHLQMHSRKHTG. (SEQ ID NO: 13)

47. The composition of item 29, wherein the cancer antigen peptide D consists of the amino acid sequence:

KLSHLQMHSRKHTGE. (SEQ ID NO: 14)

48. The composition of item 33, wherein the cancer antigen peptide D consists of the amino acid sequence:

RYFKLSHLQMHSRK. (SEQ ID NO: 39)

49. The composition of item 33, wherein the cancer antigen peptide D consists of the amino acid sequence:

AYPGCNKRYFKLSHLQMH. (SEQ ID NO: 43)

50. The composition of item 33, wherein the cancer antigen peptide D consists of the amino acid sequence:

AYPGCNKRYFKLSHLQMHSRK. (SEQ ID NO: 44)

51. The composition of item 33, wherein the cancer antigen peptide D consists of the amino acid sequence:

RYFKLSHLQMH.                                         (SEQ ID NO: 45)

52. The composition of item 33, wherein the cancer antigen peptide D consists of the amino acid sequence:

GCNKRYFKLSHL.                                        (SEQ ID NO: 46)

53. The composition of item 33, wherein the cancer antigen peptide D consists of the amino acid sequence:

RYFKLSHLQMHSRKHT.                                    (SEQ ID NO: 48)

54. The composition of item 33, wherein the cancer antigen peptide D consists of the amino acid sequence:

RYFKLSHLQMHSRKHTGE.                                  (SEQ ID NO: 49)

55. The composition of any one of items 1-54, wherein the cancer antigen peptide D induces helper T cells by binding to an MHC class II molecule selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB10202, DPB1*0402, DPB1*0501, DPB1*0901, DQB1*0301, DQB1*0302, DQB1*0401, DQB1*0501, DQB1*0601, DQB1*0602 and DRB5*0102.

56. The composition of item 55, wherein the cancer antigen peptide D induces helper T cells by binding to an MHC class II molecule selected from the group consisting of DRB1*0101, DRB1*0405, DRB1*1502, DPB1*0201, DPB1*0202 and DQB1*0601.

57. A pharmaceutical composition comprising the composition of any one of items 1-56 and a pharmaceutically acceptable carrier.

58. The pharmaceutical composition of item 57, wherein the pharmaceutical composition is for use as a cancer vaccine.

59. The composition of any one of items 1-56, wherein the composition is for use in treatment or prevention of a cancer.

60. Use of the composition of any one of items 1-56 for the manufacture of a cancer vaccine.

61. A method of treating or preventing a cancer, comprising administering to a patient in need thereof a therapeutically or prophylactically effective amount of the composition of any one of items 1-56.

62. The method of item 61, wherein the patient is WT1-positive.

63. The pharmaceutical composition, the composition, the use, or the method of any one of item 58-62, wherein the cancer is selected from the group consisting of leukemia, myelodysplastic syndrome, multiple myeloma, malignant lymphoma, gastric cancer, colorectal cancer, lung cancer, breast cancer, germ cell cancer, liver cancer, skin cancer, urinary bladder cancer, prostate cancer, uterine cancer, cervical cancer, ovarian cancer, brain tumor, bone cancer, pancreatic cancer, cancer of the head or neck, cutaneous or intraocular malignant melanoma, rectal cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia such as acute myeloid leukemia, chronic myeloid leukemia, acute lymphoblastic leukemia, or chronic lymphocytic leukemia, childhood solid tumor, lymphocytic lymphoma, cancer of the kidney or ureter, carcinoma of the renal pelvis, central nervous system (CNS) tumor, primary CNS lymphoma, tumor angiogenesis, spinal tumor, brain-stem glioma, pituitary adenoma, Kaposi's sarcoma, epidermoid cancer, squamous cell cancer, T-cell lymphoma, glioblastoma multiforme, malignant melanoma, non-small cell lung cancer, renal cell carcinoma, and asbestos-induced cancer.

64. The pharmaceutical composition, the composition, the use, or the method of any one of item 1-63, wherein the peptide or a pharmaceutically acceptable salt thereof is used in combination further with an immunomodulator.

65. The pharmaceutical composition, the composition, the use or the method of item 64, wherein the immunomodulator is an immune checkpoint inhibitor.

(3) The Third Embodiment

1. A composition comprising a compound of formula (1):

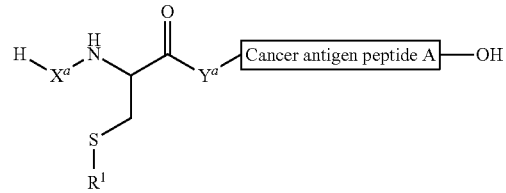

wherein
$X^a$ and $Y^a$ independently represent a single bond or a divalent peptide group consisting of 1 to 4 amino acid residues, provided that the sum of the number of amino acid residues in $X^a$ and $Y^a$ is an integer of 0 to 4;
cancer antigen peptide A is a peptide consisting of 7 to 30 amino acid residues, wherein the cancer antigen peptide A binds to $Y^a$ and OH shown in formula (1) via its N-terminal amino group and C-terminal carbonyl group, respectively; and
$R^1$ is cancer antigen peptide C, wherein the cancer antigen peptide C is a peptide consisting of 7 to 30 amino acid residues, provided that the cancer antigen peptide C has a different amino acid sequence from the cancer antigen peptide A, and wherein a thioether group of a cysteine residue of the cancer antigen peptide C binds to the thioether group in formula (1),
or a pharmaceutically acceptable salt thereof,
wherein the compound of formula (1) or a pharmaceutically acceptable salt thereof is used in combination with cancer antigen peptide D or a pharmaceutically acceptable salt thereof, wherein the cancer antigen peptide D is a partial peptide of WT1 protein consisting of an amino acid sequence of 9 to 30 amino acid residues including a sequence: KLSHL as part thereof or a peptide consisting of an amino acid sequence that differs from the amino acid sequence of the partial peptide by alteration of one or several amino acid residues, or a pharmaceutically acceptable salt thereof, provided that, when the compound of formula (1) is the compound of formula (4), the cancer antigen peptide D is neither SEQ ID NO: 7 nor SEQ ID NO: 38.

2. The composition of item 1, wherein the compound of formula (1) or a pharmaceutically acceptable salt thereof and the peptide or a pharmaceutically acceptable salt thereof are formulated in separate compositions.

3. The composition of item 1, wherein the compound of formula (1) or a pharmaceutically acceptable salt thereof and the peptide or a pharmaceutically acceptable salt thereof are incorporated in a single composition.

4. The composition of any one of items 1-3, wherein $X^a$ is a single bond or a residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, and $Y^a$ is a single bond.

5. The composition of item 4, wherein $X^a$ is a single bond or a residue of alanine, leucine, or methionine, and $Y^a$ is a single bond.

6. The composition of item 5, wherein $X^a$ and $Y^a$ are both single bonds.

7. The composition of any one of items 1-6, wherein the cancer antigen peptide A is a peptide consisting of 7 to 15 amino acid residues.

8. The composition of item 7, wherein the cancer antigen peptide A is a peptide comprising an amino acid sequence selected from:

RMFPNAPYL, (SEQ ID NO: 15)

CMTWNQMNL, (SEQ ID NO: 16)

ALLPAVPSL, (SEQ ID NO: 18)

SLGEQQYSV, (SEQ ID NO: 19)

RVPGVAPTL, (SEQ ID NO: 20)
and

VLDFAPPGA, (SEQ ID NO: 21)

or a peptide comprising an amino acid sequence that differs from the amino acid sequence selected from SEQ ID NOS: 15, 16, 18, 19, 20 and 21 by alteration of one or several amino acid residues.

9. The composition of item 8, wherein the cancer antigen peptide A is a peptide consisting of an amino acid sequence selected from:

RMFPNAPYL, (SEQ ID NO: 15)

CMTWNQMNL, (SEQ ID NO: 16)

CYTWNQMNL, (SEQ ID NO: 17)

ALLPAVPSL, (SEQ ID NO: 18)

SLGEQQYSV, (SEQ ID NO: 19)

RVPGVAPTL, (SEQ ID NO: 20)
and

VLDFAPPGA. (SEQ ID NO: 21)

10. The composition of item 9, wherein the cancer antigen peptide A consists of the amino acid sequence:

RMFPNAPYL. (SEQ ID NO: 15)

11. The composition of any one of items 1-10, wherein the cancer antigen peptide C is a peptide consisting of 7 to 15 amino acid residues.

12. The composition of item 11, wherein the cancer antigen peptide C is a peptide comprising an amino acid sequence selected from:

CMTWNQMNL, (SEQ ID NO: 16)
and

CYTWNQMNL, (SEQ ID NO: 17)

or a peptide comprising an amino acid sequence that differs from the amino acid sequence selected from SEQ ID NOS: 16 and 17 by alteration of one or several amino acid residues.

13. The composition of item 12, wherein the cancer antigen peptide C is a peptide consisting of an amino acid sequence selected from:

CMTWNQMNL, (SEQ ID NO: 16)
and

CYTWNQMNL. (SEQ ID NO: 17)

14. The composition of item 13, wherein the cancer antigen peptide C is a peptide consisting of the amino acid sequence:

CMTWNQMNL. (SEQ ID NO: 16)

15. The composition of item 13, wherein the cancer antigen peptide C is a peptide consisting of the amino acid sequence:

CYTWNQMNL. (SEQ ID NO: 17)

16. The composition of item 14, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof.

17. The composition of item 15, wherein the compound of formula (1) or a pharmaceutically acceptable salt thereof is the compound of formula (4):

$$(4)$$
```
CRMFPNAPYL   (SEQ ID NO: 35),
|
CYTWNQMNL    (SEQ ID NO: 17)
``` wherein C—C shown in the formula means that the residues are linked together by a disulfide bond, or a pharmaceutically acceptable salt thereof.

18. The composition of any one of items 1-17, wherein the cancer antigen peptide D is a peptide consisting of 10 to 25 amino acid residues.

19. The composition of item 18, wherein the cancer antigen peptide D is a peptide consisting of 12 to 24 amino acid residues.

20. The composition of item 19, wherein the cancer antigen peptide D is a peptide consisting of an amino acid sequence selected from:

```
AYPGCNKRYFKLSHL,         (SEQ ID NO: 2)

YPGCNKRYFKLSHLQ,         (SEQ ID NO: 3)

PGCNKRYFKLSHLQMHSRKHTG,  (SEQ ID NO: 4)

PGCNKRYFKLSHLQMHSRK,     (SEQ ID NO: 5)

GCNKRYFKLSHLQMHSRK,      (SEQ ID NO: 6)

CNKRYFKLSHLQMHSRK,       (SEQ ID NO: 7)

NKRYFKLSHLQMHSRK,        (SEQ ID NO: 8)

KRYFKLSHLQMHSRK,         (SEQ ID NO: 9)

KRYFKLSHLQMHSRKH,        (SEQ ID NO: 10)

RYFKLSHLQMHSRKH,         (SEQ ID NO: 11)

YFKLSHLQMHSRKHT,         (SEQ ID NO: 12)

FKLSHLQMHSRKHTG,         (SEQ ID NO: 13)
and

KLSHLQMHSRKHTGE,         (SEQ ID NO: 14)
``` or a peptide consisting of an amino acid sequence that differs from the amino acid sequence of the peptide by alteration of one or several amino acid residues.

21. The composition of item 20, wherein the cancer antigen peptide D is a peptide consisting of an amino acid sequence selected from:

```
AYPGCNKRYFKLSHL,         (SEQ ID NO: 2)

YPGCNKRYFKLSHLQ,         (SEQ ID NO: 3)

PGCNKRYFKLSHLQMHSRKHTG,  (SEQ ID NO: 4)

PGCNKRYFKLSHLQMHSRK,     (SEQ ID NO: 5)

GCNKRYFKLSHLQMHSRK,      (SEQ ID NO: 6)

NKRYFKLSHLQMHSRK,        (SEQ ID NO: 8)

KRYFKLSHLQMHSRK,         (SEQ ID NO: 9)

KRYFKLSHLQMHSRKH,        (SEQ ID NO: 10)

RYFKLSHLQMHSRKH,         (SEQ ID NO: 11)

YFKLSHLQMHSRKHT,         (SEQ ID NO: 12)

FKLSHLQMHSRKHTG,         (SEQ ID NO: 13)
and

KLSHLQMHSRKHTGE,         (SEQ ID NO: 14)
``` or a peptide consisting of an amino acid sequence that differs from the amino acid sequence of the peptide by alteration of one or several amino acid residues.

22. The composition of item 21, wherein the cancer antigen peptide D is a peptide consisting of an amino acid sequence selected from:

```
AYPGCNKRYFKLSHL,         (SEQ ID NO: 2)

YPGCNKRYFKLSHLQ,         (SEQ ID NO: 3)

GCNKRYFKLSHLQMHSRK,      (SEQ ID NO: 6)

NKRYFKLSHLQMHSRK,        (SEQ ID NO: 8)

KRYFKLSHLQMHSRK,         (SEQ ID NO: 9)

RYFKLSHLQMHSRKH,         (SEQ ID NO: 11)

YFKLSHLQMHSRKHT,         (SEQ ID NO: 12)

FKLSHLQMHSRKHTG,         (SEQ ID NO: 13)
and

KLSHLQMHSRKHTGE,         (SEQ ID NO: 14)
``` or a peptide consisting of an amino acid sequence that differs from the amino acid sequence of the peptide by alteration of one or several amino acid residues.

23. The composition of item 20, wherein the cancer antigen peptide D is a peptide consisting of an amino acid sequence of 15 to 22 amino acid residues.

24. The composition of item 23, wherein the cancer antigen peptide D is a peptide consisting of an amino acid sequence selected from:

```
                            (SEQ ID NO: 2)
AYPGCNKRYFKLSHL, (SEQ ID NO: 3)
YPGCNKRYFKLSHLQ, (SEQ ID NO: 4)
PGCNKRYFKLSHLQMHSRKHTG, (SEQ ID NO: 5)
PGCNKRYFKLSHLQMHSRK, (SEQ ID NO: 6)
GCNKRYFKLSHLQMHSRK, (SEQ ID NO: 7)
CNKRYFKLSHLQMHSRK, (SEQ ID NO: 8)
NKRYFKLSHLQMHSRK, (SEQ ID NO: 9)
KRYFKLSHLQMHSRK, (SEQ ID NO: 10)
KRYFKLSHLQMHSRKH, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG,
and (SEQ ID NO: 14)
KLSHLQMHSRKHTGE.
```

25. The composition of item 24, wherein the cancer antigen peptide D is a peptide consisting of an amino acid sequence selected from:

```
                            (SEQ ID NO: 2)
AYPGCNKRYFKLSHL, (SEQ ID NO: 3)
YPGCNKRYFKLSHLQ, (SEQ ID NO: 4)
PGCNKRYFKLSHLQMHSRKHTG, (SEQ ID NO: 5)
PGCNKRYFKLSHLQMHSRK, (SEQ ID NO: 6)
GCNKRYFKLSHLQMHSRK, (SEQ ID NO: 8)
NKRYFKLSHLQMHSRK, (SEQ ID NO: 9)
KRYFKLSHLQMHSRK, (SEQ ID NO: 10)
KRYFKLSHLQMHSRKH, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG,
and (SEQ ID NO: 14)
KLSHLQMHSRKHTGE.
```

26. The composition of item 25, wherein the cancer antigen peptide D is a peptide consisting of an amino acid sequence selected from:

```
                            (SEQ ID NO: 2)
AYPGCNKRYFKLSHL, (SEQ ID NO: 3)
YPGCNKRYFKLSHLQ, (SEQ ID NO: 6)
GCNKRYFKLSHLQMHSRK, (SEQ ID NO: 8)
NKRYFKLSHLQMHSRK, (SEQ ID NO: 9)
KRYFKLSHLQMHSRK, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG,
and (SEQ ID NO: 14)
KLSHLQMHSRKHTGE.
```

27. The composition of item 18, wherein the cancer antigen peptide D is a peptide consisting of an amino acid sequence selected from:

```
                            (SEQ ID NO: 39)
RYFKLSHLQMHSRK, (SEQ ID NO: 40)
YFKLSHLQMHSRK, (SEQ ID NO: 41)
FKLSHLQMHSRK, (SEQ ID NO: 42)
KLSHLQMHSRK, (SEQ ID NO: 43)
AYPGCNKRYFKLSHLQMH, (SEQ ID NO: 44)
AYPGCNKRYFKLSHLQMHSRK, (SEQ ID NO: 45)
RYFKLSHLQMH, (SEQ ID NO: 46)
GCNKRYFKLSHL, (SEQ ID NO: 47)
FKLSHLQMHSRKHTGE, (SEQ ID NO: 48)
RYFKLSHLQMHSRKHT, (SEQ ID NO: 49)
RYFKLSHLQMHSRKHTGE, (SEQ ID NO: 50)
KLSHLQMHSRKH,
```

```
                                          (SEQ ID NO: 51)
YPGCNKRYFKLSHLQMHSRK, (SEQ ID NO: 52)
AYPGCNKRYFKLSHLQMHSR, (SEQ ID NO: 53)
AYPGCNKRYFKLSHLQMHS, (SEQ ID NO: 54)
AYPGCNKRYFKLSHLQM, (SEQ ID NO: 55)
AYPGCNKRYFKLSHLQ, (SEQ ID NO: 56)
YFKLSHLQMHSRKHTGE, (SEQ ID NO: 57)
RYFKLSHLQMHSRKHTG, (SEQ ID NO: 58)
RYFKLSHLQMHSR, (SEQ ID NO: 59)
RYFKLSHLQMHS, (SEQ ID NO: 60)
RYFKLSHLQM, (SEQ ID NO: 61)
YPGCNKRYFKLSHL, (SEQ ID NO: 62)
PGCNKRYFKLSHL, (SEQ ID NO: 63)
CNKRYFKLSHL, (SEQ ID NO: 64)
NKRYFKLSHL, (SEQ ID NO: 65)
KLSHLQMHSRKHTG, (SEQ ID NO: 66)
KLSHLQMHSRKHT, (SEQ ID NO: 67)
KLSHLQMHSRK,
and (SEQ ID NO: 68)
KLSHLQMHSR,
``` or a peptide consisting of an amino acid sequence that differs from the amino acid sequence of the peptide by alteration of one or several amino acid residues.

28. The composition of item 27, wherein the cancer antigen peptide D is a peptide consisting of an amino acid sequence selected from:

```
                                          (SEQ ID NO: 39)
RYFKLSHLQMHSRK, (SEQ ID NO: 40)
YFKLSHLQMHSRK, (SEQ ID NO: 41)
FKLSHLQMHSRK, (SEQ ID NO: 42)
KLSHLQMHSRK, (SEQ ID NO: 43)
AYPGCNKRYFKLSHLQMH, (SEQ ID NO: 44)
AYPGCNKRYFKLSHLQMHSRK, (SEQ ID NO: 45)
RYFKLSHLQMH, (SEQ ID NO: 46)
GCNKRYFKLSHL, (SEQ ID NO: 47)
FKLSHLQMHSRKHTGE, (SEQ ID NO: 48)
RYFKLSHLQMHSRKHT, (SEQ ID NO: 49)
RYFKLSHLQMHSRKHTGE, (SEQ ID NO: 50)
KLSHLQMHSRKH, (SEQ ID NO: 51)
YPGCNKRYFKLSHLQMHSRK, (SEQ ID NO: 52)
AYPGCNKRYFKLSHLQMHSR, (SEQ ID NO: 53)
AYPGCNKRYFKLSHLQMHS, (SEQ ID NO: 54)
AYPGCNKRYFKLSHLQM, (SEQ ID NO: 55)
AYPGCNKRYFKLSHLQ, (SEQ ID NO: 56)
YFKLSHLQMHSRKHTGE, (SEQ ID NO: 57)
RYFKLSHLQMHSRKHTG, (SEQ ID NO: 58)
RYFKLSHLQMHSR, (SEQ ID NO: 59)
RYFKLSHLQMHS, (SEQ ID NO: 60)
RYFKLSHLQM, (SEQ ID NO: 61)
YPGCNKRYFKLSHL, (SEQ ID NO: 62)
PGCNKRYFKLSHL, (SEQ ID NO: 63)
CNKRYFKLSHL, (SEQ ID NO: 64)
NKRYFKLSHL, (SEQ ID NO: 65)
KLSHLQMHSRKHTG, (SEQ ID NO: 66)
KLSHLQMHSRKHT, (SEQ ID NO: 67)
KLSHLQMHSRK,
and (SEQ ID NO: 68)
KLSHLQMHSR.
```

29. The composition of item 18, wherein the cancer antigen peptide D is a peptide comprising an amino acid sequence selected from:

```
                              (SEQ ID NO: 2)
AYPGCNKRYFKLSHL, (SEQ ID NO: 3)
YPGCNKRYFKLSHLQ, (SEQ ID NO: 6)
GCNKRYFKLSHLQMHSRK, (SEQ ID NO: 8)
NKRYFKLSHLQMHSRK, (SEQ ID NO: 9)
KRYFKLSHLQMHSRK, (SEQ ID NO: 11)
RYFKLSHLQMHSRKH, (SEQ ID NO: 12)
YFKLSHLQMHSRKHT, (SEQ ID NO: 13)
FKLSHLQMHSRKHTG, (SEQ ID NO: 14)
KLSHLQMHSRKHTGE, (SEQ ID NO: 39)
RYFKLSHLQMHSRK, (SEQ ID NO: 40)
YFKLSHLQMHSRK, (SEQ ID NO: 41)
FKLSHLQMHSRK, (SEQ ID NO: 42)
KLSHLQMHSRK, (SEQ ID NO: 43)
AYPGCNKRYFKLSHLQMH, (SEQ ID NO: 44)
AYPGCNKRYFKLSHLQMHSRK, (SEQ ID NO: 45)
RYFKLSHLQMH, (SEQ ID NO: 46)
GCNKRYFKLSHL, (SEQ ID NO: 47)
FKLSHLQMHSRKHTGE, (SEQ ID NO: 48)
RYFKLSHLQMHSRKHT, (SEQ ID NO: 49)
RYFKLSHLQMHSRKHTGE, (SEQ ID NO: 50)
KLSHLQMHSRKH, (SEQ ID NO: 51)
YPGCNKRYFKLSHLQMHSRK, (SEQ ID NO: 52)
AYPGCNKRYFKLSHLQMHSR, (SEQ ID NO: 53)
AYPGCNKRYFKLSHLQMHS, (SEQ ID NO: 54)
AYPGCNKRYFKLSHLQM, (SEQ ID NO: 55)
AYPGCNKRYFKLSHLQ, (SEQ ID NO: 56)
YFKLSHLQMHSRKHTGE, (SEQ ID NO: 57)
RYFKLSHLQMHSRKHTG, (SEQ ID NO: 58)
RYFKLSHLQMHSR, (SEQ ID NO: 59)
RYFKLSHLQMHS, (SEQ ID NO: 60)
RYFKLSHLQM, (SEQ ID NO: 61)
YPGCNKRYFKLSHL, (SEQ ID NO: 62)
PGCNKRYFKLSHL, (SEQ ID NO: 63)
CNKRYFKLSHL, (SEQ ID NO: 64)
NKRYFKLSHL, (SEQ ID NO: 65)
KLSHLQMHSRKHTG, (SEQ ID NO: 66)
KLSHLQMHSRKHT, (SEQ ID NO: 67)
KLSHLQMHSRK,
and
                              (SEQ ID NO: 68)
KLSHLQMHSR.
```

30. The composition of item 24, wherein the cancer antigen peptide D consists of the amino acid sequence:

```
                              (SEQ ID NO: 2)
AYPGCNKRYFKLSHL.
```

31. The composition of item 24, wherein the cancer antigen peptide D consists of the amino acid sequence:

```
                              (SEQ ID NO: 3)
YPGCNKRYFKLSHLQ.
```

32. The composition of item 24, wherein the cancer antigen peptide D consists of the amino acid sequence:

```
                              (SEQ ID NO: 4)
PGCNKRYFKLSHLQMHSRKHTG.
```

33. The composition of item 24, wherein the cancer antigen peptide D consists of the amino acid sequence:

```
                              (SEQ ID NO: 5)
PGCNKRYFKLSHLQMHSRK.
```

34. The composition of item 24, wherein the cancer antigen peptide D consists of the amino acid sequence:

```
                              (SEQ ID NO: 6)
GCNKRYFKLSHLQMHSRK.
```

35. The composition of item 24, wherein the cancer antigen peptide D consists of the amino acid sequence:

```
                              (SEQ ID NO: 7)
CNKRYFKLSHLQMHSRK.
```

36. The composition of item 24, wherein the cancer antigen peptide D consists of the amino acid sequence:

```
                              (SEQ ID NO: 8)
NKRYFKLSHLQMHSRK.
```

37. The composition of item 24, wherein the cancer antigen peptide D consists of the amino acid sequence:

```
                              (SEQ ID NO: 9)
KRYFKLSHLQMHSRK.
```

38. The composition of item 24, wherein the cancer antigen peptide D consists of the amino acid sequence:

```
                              (SEQ ID NO: 10)
KRYFKLSHLQMHSRKH.
```

39. The composition of item 24, wherein the cancer antigen peptide D consists of the amino acid sequence:

```
                              (SEQ ID NO: 11)
RYFKLSHLQMHSRKH.
```

40. The composition of item 24, wherein the cancer antigen peptide D consists of the amino acid sequence:

```
                              (SEQ ID NO: 12)
YFKLSHLQMHSRKHT.
```

41. The composition of item 24, wherein the cancer antigen peptide D consists of the amino acid sequence:

```
                              (SEQ ID NO: 13)
FKLSHLQMHSRKHTG.
```

42. The composition of item 24, wherein the cancer antigen peptide D consists of the amino acid sequence:

```
                              (SEQ ID NO: 14)
KLSHLQMHSRKHTGE.
```

43. The composition of item 28, wherein the cancer antigen peptide D consists of the amino acid sequence:

```
                              (SEQ ID NO: 39)
RYFKLSHLQMHSRK.
```

44. The composition of item 28, wherein the cancer antigen peptide D consists of the amino acid sequence:

```
                              (SEQ ID NO: 43)
AYPGCNKRYFKLSHLQMHSRK.
```

45. The composition of item 28, wherein the cancer antigen peptide D consists of the amino acid sequence:

```
                              (SEQ ID NO: 44)
AYPGCNKRYFKLSHLQMHSRK.
```

46. The composition of item 28, wherein the cancer antigen peptide D consists of the amino acid sequence:

```
                              (SEQ ID NO: 45)
RYFKLSHLQMH.
```

47. The composition of item 28, wherein the cancer antigen peptide D consists of the amino acid sequence:

```
                              (SEQ ID NO: 46)
GCNKRYFKLSHL.
```

48. The composition of item 28, wherein the cancer antigen peptide D consists of the amino acid sequence:

```
                              (SEQ ID NO: 48)
RYFKLSHLQMHSRKHT.
```

49. The composition of item 28, wherein the cancer antigen peptide D consists of the amino acid sequence:

```
                              (SEQ ID NO: 49)
RYFKLSHLQMHSRKHTGE.
```

50. The composition of any one of items 1-49, wherein the cancer antigen peptide D induces helper T cells by binding to an MHC class II molecule selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602 and DRB5*0102.

51. The composition of item 50, wherein the cancer antigen peptide D induces helper T cells by binding to an MHC class II molecule selected from the group consisting of DRB1*0101, DRB1*0405, DRB1*1502, DPB1*0201, DPB1*0202 and DQB1*0601.

52. The composition of any one of items 1-14, 16 and 18-51, wherein the compound of formula (1) or a pharmaceutically acceptable salt thereof is the compound of formula (3):

$$
\begin{array}{l}
\text{CRMFPNAPYL} \quad \text{(SEQ ID NO: 35),} \\
| \\
\text{CMTWNQMNL} \quad \text{(SEQ ID NO: 16)}
\end{array}
\tag{3}
$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHL (SEQ ID NO: 2) or a pharmaceutically acceptable salt thereof.

53. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: YPGCNKRYFKLSHLQ (SEQ ID NO: 3) or a pharmaceutically acceptable salt thereof.

54. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: PGCNKRYFKLSHLQMHSRKHTG (SEQ ID NO: 4) or a pharmaceutically acceptable salt thereof.

55. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: PGCNKRYFKLSHLQMHSRK (SEQ ID NO: 5) or a pharmaceutically acceptable salt thereof.

56. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: GCNKRYFKLSHLQMHSRK (SEQ ID NO: 6) or a pharmaceutically acceptable salt thereof.

57. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: CNKRYFKLSHLQMHSRK (SEQ ID NO: 7) or a pharmaceutically acceptable salt thereof.

58. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: NKRYFKLSHLQMHSRK (SEQ ID NO: 8) or a pharmaceutically acceptable salt thereof.

59. The composition of any one of items 1-14, 16 and 18-51, wherein the compound of formula (1) or a pharmaceutically acceptable salt thereof is the compound of formula (3):

$$\begin{array}{ll} \text{CRMFPNAPYL} & \text{(SEQ ID NO: 35),} \\ | & \\ \text{CMTWNQMNL} & \text{(SEQ ID NO: 16)} \end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KRYFKLSHLQMHSRK (SEQ ID NO: 9) or a pharmaceutically acceptable salt thereof.

60. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KRYFKLSHLQMHSRKH (SEQ ID NO: 10) or a pharmaceutically acceptable salt thereof.

61. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKH (SEQ ID NO: 11) or a pharmaceutically acceptable salt thereof.

62. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: YFKLSHLQMHSRKHT (SEQ ID NO: 12) or a pharmaceutically acceptable salt thereof.

63. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: FKLSHLQMHSRKHTG (SEQ ID NO: 13) or a pharmaceutically acceptable salt thereof.

64. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KLSHLQMHSRKHTGE (SEQ ID NO: 14) or a pharmaceutically acceptable salt thereof.

65. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRK (SEQ ID NO: 39) or a pharmaceutically acceptable salt thereof.

66. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHLQMH (SEQ ID NO: 43) or a pharmaceutically acceptable salt thereof.

67. The composition of any one of items 1-14, 16 and 18-51, wherein the compound of formula (1) or a pharmaceutically acceptable salt thereof is the compound of formula (3):

$$\begin{array}{l}\text{CRMFPNAPYL} \quad \text{(SEQ ID NO: 35),} \\ | \\ \text{CMTWNQMNL} \quad \text{(SEQ ID NO: 16)}\end{array} \quad (3)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHLQMHSRK (SEQ ID NO: 44) or a pharmaceutically acceptable salt thereof.

68. The composition of any one of items 1-14, 16 and 18-51, wherein the compound of formula (1) or a pharmaceutically acceptable salt thereof is the compound of formula (3):

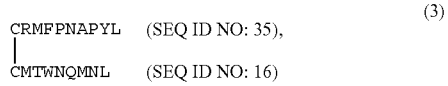

(3)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMH (SEQ ID NO: 45) or a pharmaceutically acceptable salt thereof.

69. The composition of any one of items 1-14, 16 and 18-51, wherein the compound of formula (1) or a pharmaceutically acceptable salt thereof is the compound of formula (3):

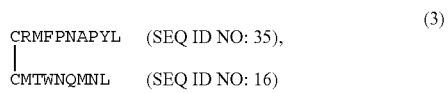

(3)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: GCNKRYFKLSHL (SEQ ID NO: 46) or a pharmaceutically acceptable salt thereof.

70. The composition of any one of items 1-14, 16 and 18-51, wherein the compound of formula (1) or a pharmaceutically acceptable salt thereof is the compound of formula (3):

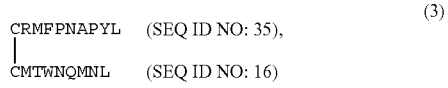

(3)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKHT (SEQ ID NO: 48) or a pharmaceutically acceptable salt thereof.

71. The composition of any one of items 1-14, 16 and 18-51, wherein the compound of formula (1) or a pharmaceutically acceptable salt thereof is the compound of formula (3):

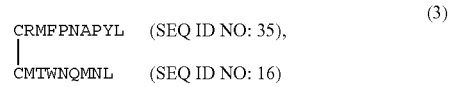

(3)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKHTGE (SEQ ID NO: 49) or a pharmaceutically acceptable salt thereof.

72. The composition of any one of items 1-13, 15 and 17-51, wherein the compound of formula (1) or a pharmaceutically acceptable salt thereof is the compound of formula (4):

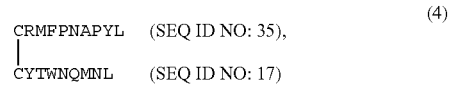

(4)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHL (SEQ ID NO: 2) or a pharmaceutically acceptable salt thereof.

73. The composition of any one of items 1-13, 15 and 17-51, wherein the compound of formula (1) or a pharmaceutically acceptable salt thereof is the compound of formula (4):

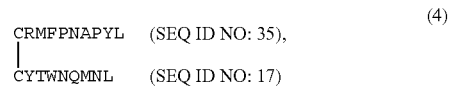

(4)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: YPGCNKRYFKLSHLQ (SEQ ID NO: 3) or a pharmaceutically acceptable salt thereof.

74. The composition of any one of items 1-13, 15 and 17-51, wherein the compound of formula (1) or a pharmaceutically acceptable salt thereof is the compound of formula (4):

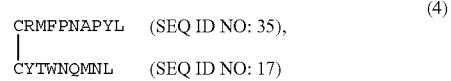

(4)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: PGCNKRYFKLSHLQMHSRKHTG (SEQ ID NO: 4) or a pharmaceutically acceptable salt thereof.

75. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: PGCNKRYFKLSHLQMHSRK (SEQ ID NO: 5) or a pharmaceutically acceptable salt thereof.

76. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: GCNKRYFKLSHLQMHSRK (SEQ ID NO: 6) or a pharmaceutically acceptable salt thereof.

77. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: NKRYFKLSHLQMHSRK (SEQ ID NO: 8) or a pharmaceutically acceptable salt thereof.

78. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KRYFKLSHLQMHSRK (SEQ ID NO: 9) or a pharmaceutically acceptable salt thereof.

79. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KRYFKLSHLQMHSRKH (SEQ ID NO: 10) or a pharmaceutically acceptable salt thereof.

80. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKH (SEQ ID NO: 11) or a pharmaceutically acceptable salt thereof.

81. The composition of any one of items 1-13, 15 and 17-51, wherein the compound of formula (1) or a pharmaceutically acceptable salt thereof is the compound of formula (4):

$$\begin{array}{ll} \text{CRMFPNAPYL} & \text{(SEQ ID NO: 35),} \\ | & \\ \text{CYTWNQMNL} & \text{(SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: YFKLSHLQMHSRKHT (SEQ ID NO: 12) or a pharmaceutically acceptable salt thereof.

82. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: FKLSHLQMHSRKHTG (SEQ ID NO: 13) or a pharmaceutically acceptable salt thereof.

83. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KLSHLQMHSRKHTGE (SEQ ID NO: 14) or a pharmaceutically acceptable salt thereof.

84. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRK (SEQ ID NO: 39) or a pharmaceutically acceptable salt thereof.

85. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHLQMH (SEQ ID NO: 43) or a pharmaceutically acceptable salt thereof.

86. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHLQMHSRK (SEQ ID NO: 44) or a pharmaceutically acceptable salt thereof.

87. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond or a pharmaceutically acceptable salt thereof, and the cancer antigen peptide D or a pharmaceutically acceptable salt thereof is a peptide consisting of the amino acid sequence: RYFKLSHLQMH (SEQ ID NO: 45) or a pharmaceutically acceptable salt thereof.

88. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: GCNKRYFKLSHL (SEQ ID NO: 46) or a pharmaceutically acceptable salt thereof.

89. The composition of any one of items 1-13, 15 and 17-51, wherein the compound of formula (1) or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKHT (SEQ ID NO: 48) or a pharmaceutically acceptable salt thereof.

90. The composition of any one of items 1-13, 15 and 17-51, wherein the compound of formula (1) or a pharmaceutically acceptable salt thereof is the compound of formula (4):

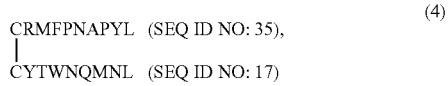

(4)

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKHTGE (SEQ ID NO: 49) or a pharmaceutically acceptable salt thereof.

91. A pharmaceutical composition comprising the composition of any one of items 1-90 and a pharmaceutically acceptable carrier.

92. The pharmaceutical composition of item 91, wherein the composition is for use as a composition for treating a cancer associated with WT1 gene expression or an elevated level of WT1 gene expression.

93. The pharmaceutical composition of item 91, wherein the composition is for use as a composition for inducing CTLs in cellular immunotherapy for a cancer.

94. The pharmaceutical composition of item 91, wherein the pharmaceutical composition is for use as a cancer vaccine.

95. The composition of any one of items 1-90, wherein the composition is for use in treatment or prevention of a cancer.

96. Use of the composition of any one of items 1-90 for the manufacture of a cancer vaccine.

97. A method of treating or preventing a cancer, comprising administering to a patient in need thereof a therapeutically or prophylactically effective amount of the composition of any one of items 1-90.

98. The method of item 97, wherein the patient is WT1-positive.

99. The pharmaceutical composition, the composition, the use, or the method of any one of item 92-98, wherein the cancer is selected from the group consisting of leukemia, myelodysplastic syndrome, multiple myeloma, malignant lymphoma, gastric cancer, colorectal cancer, lung cancer, breast cancer, germ cell cancer, liver cancer, skin cancer, urinary bladder cancer, prostate cancer, uterine cancer, cervical cancer, ovarian cancer, brain tumor, bone cancer, pancreatic cancer, cancer of the head or neck, cutaneous or intraocular malignant melanoma, rectal cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia such as acute myeloid leukemia, chronic myeloid leukemia, acute lymphoblastic leukemia, or chronic lymphocytic leukemia, childhood solid tumor, lymphocytic lymphoma, cancer of the kidney or ureter, carcinoma of the renal pelvis, central nervous system (CNS) tumor, primary CNS lymphoma, tumor angiogenesis, spinal tumor, brainstem glioma, pituitary adenoma, Kaposi's sarcoma, epidermoid cancer, squamous cell cancer, T-cell lymphoma, glioblastoma multiforme, malignant melanoma, non-small cell lung cancer, renal cell carcinoma, and asbestos-induced cancer.

100. The pharmaceutical composition, the composition, the use, or the method of any one of item 1-99, wherein the peptide or a pharmaceutically acceptable salt thereof is used in combination further with an immunomodulator.

101. The pharmaceutical composition, the composition, the use, or the method of item 100, wherein the immunomodulator is an immune checkpoint inhibitor.

Effect of Invention

The present invention provides new WT1 helper peptides, and also new combinations of WT1 peptide conjugates with WT1 helper peptides. Thus, the present invention provides a cancer vaccine or a composition for cancer immunotherapy, which induces CTLs efficiently. Therefore, the present invention can find applications in the medical field, for example in development or production of compositions for treatment or prevention of a cancer.

DESCRIPTION OF EMBODIMENTS

Figure 1:
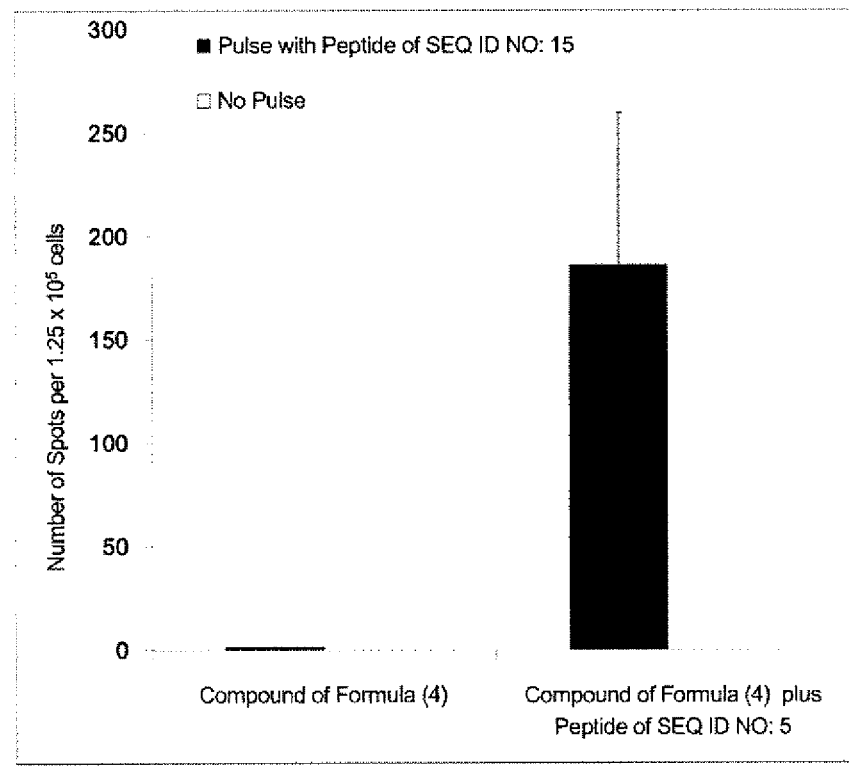
FIG. 1 shows in vivo CTL induction in an HLA-A*02:01 transgenic mouse by a cocktail vaccine comprising the compound of formula (4) synthesized in Reference Example 7 and the peptide of SEQ ID NO: 5 in an IFNγ ELISOPOT assay of Experimental Example 1.

Embodiments of the present invention are described in detail below.

An "amino acid residue" as used herein refers to a single amino acid unit among amino acids constituting a peptide or protein molecule. An "amino acid residue" may be a natural or non-natural α-amino acid residue, β-amino acid residue, γ-amino acid residue or δ-amino acid residue, more specifically, a natural α-amino acid residue, ornithine residue, homoserine residue, homocysteine residue, n-alanine, γ-aminobutanoic acid or δ-aminopentanoic acid. When an "amino acid residue" is optically active, it includes L-form and D-form, and is preferably L-form.

For describing an "amino acid residue", an abbreviation for it may be used. The following is a list of the abbreviations:

Ala or A: alanine residue
Arg or R: arginine residue
Asn or N: asparagine residue
Asp or D: aspartic acid residue
Cys or C: cysteine residue
Gln or Q: glutamine residue
Glu or E: glutamic acid residue
Gly or G: glycine residue
His or H: histidine residue
Ile or I: isoleucine residue
Leu or L: leucine residue
Lys or K: lysine residue
Met or M: methionine residue
Phe or F: phenylalanine residue
Pro or P: proline residue
Ser or S: serine residue
Thr or T: threonine residue
Trp or W: tryptophan residue
Tyr or Y: tyrosine residue
Val or V: valine residue
Abu: 2-aminobutyric acid residue (also referred to as α-aminobutyric acid residue)
Orn: ornithine residue
Cit: citrulline residue The term "N-terminus" as used herein in relation to a peptide refers to the terminal of a peptide chain where the peptide chain has a free amino group (—NH$_2$). The free amino group may optionally be modified. The term "C-terminus" as used herein in relation to a peptide refers to the terminal of a peptide chain where the peptide chain has a free carboxyl group (—COOH). The free carboxyl group may optionally be modified.

An amino acid sequence of a "peptide" is described herein so that an N-terminal amino acid residue is positioned on the left side, and a C-terminal amino acid residue is positioned on the right side in accordance with a usual description method. Unless otherwise indicated, a "peptide" has a free amino group in its N-terminal amino acid residue, and a hydroxyl group attaching to a carbonyl group in its C-terminal amino acid residue. A divalent peptide group means a peptide group which is able to bind to other chemical moieties via the N-terminal amino group and via the C-terminal carbonyl group.

Unless otherwise indicated, a peptide corresponding to partial structure of a compound of formula (1) (herein also referred to as "compound of the present invention"), for example, the compound of formula (3) or formula (4), has a free amino group in its N-terminal amino acid residue, and a hydroxyl group attaching to a carbonyl group in its C-terminal amino acid residue.

In formula (1), "$X^a$" and "$Y^a$" independently represents a single bond or a divalent peptide group consisting of 1 to 4 amino acid residues, provided that the sum of the number of amino acid residues in $X^a$ and $Y^a$ is an integer of 0 to 4. For example, when the sum of the number of amino acid residues in $X^a$ and $Y^a$ is an integer of 0, both $X^a$ and $Y^a$ must be single bonds; and when the sum of the number of amino acid residues in $X^a$ and $Y^a$ is an integer of 4, each of $X^a$ and $Y^a$ may be a divalent peptide group consisting of two amino acid residues, or $X^a$ may be a divalent peptide group consisting of three amino acid residues, and $Y^a$ may be a divalent peptide group consisting of one amino acid residue, or $X^a$ may be a divalent peptide group consisting of four amino acid residues, and $Y^a$ may be a single bond.

The sum of the number of amino acid residues in $X^a$ and $Y^a$ is preferably an integer of 0 to 2, more preferably an integer of 0 to 1, or most preferably zero. That is, most preferably, $X^a$ and $Y^a$ are both single bonds.

When the sum of the number of amino acid residues in $X^a$ and $Y^a$ is an integer of 1, $X^a$ may be a divalent peptide group consisting of one amino acid residue, and Y may be a single bond; or $X^a$ may be a single bond, and $Y^a$ may be a divalent peptide group consisting of one amino acid residue. In a preferred embodiment, $X^a$ is a single bond, and $Y^a$ is a residue of alanine, leucine or methionine; or $X^a$ is a residue of alanine, leucine or methionine, and $Y^a$ is a single bond.

"Cancer antigen peptide A" is an MHC class I-restricted peptide consisting of 7 to 30 amino acid residues, or an altered form thereof which is capable of inducing CTLs. In formula (1), cancer antigen peptide A binds to $Y^a$ and OH shown in formula (1) via its N-terminal amino group and C-terminal carbonyl group, respectively.

In formula (1), "$R^1$" is hydrogen, a group of formula (2), or cancer antigen peptide C. Preferably, $R^1$ is a group of formula (2), or cancer antigen peptide C.

When $R^1$ is hydrogen, the compound of formula (1) is a compound (peptide) of formula (1-1):

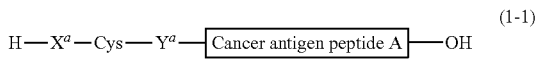
(1-1)

wherein $X^a$, $Y^a$ and cancer antigen peptide A have the same meanings as defined above in relation to formula (1), and Cys represents a cysteine residue.

When $R^1$ is hydrogen, that is, when the compound of formula (1) is a peptide of formula (1-1), the peptide is not a partial peptide of WT1 protein. When a peptide of formula (1) is described to be "not a partial peptide of WT1 protein", it is meant that the peptide of formula (1-1) is not a peptide consisting of contiguous amino acid residues in the amino acid sequence of human WT1 protein of SEQ ID NO: 1.

When $R^1$ is a group of formula (2), the compound of formula (I) is a compound of formula (1-2):

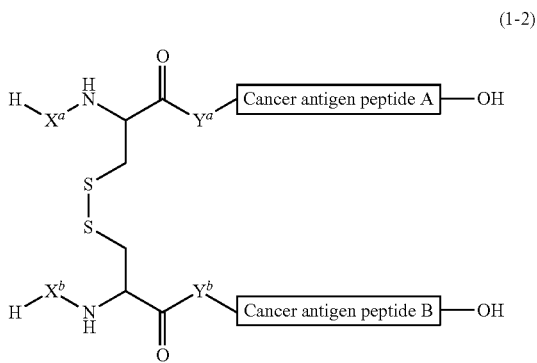
(1-2)

wherein $X^a$, $Y^a$ and cancer antigen peptide A have the same meanings as defined above in relation to formula (1), and $X^b$, $Y^b$ and cancer antigen peptide B have the same meanings as defined above in relation to formula (2).

"$X^b$" And "$Y^b$" independently represent a single bond or a divalent peptide group consisting of 1 to 4 amino acid residues, provided that the sum of the number of amino acid residues in $X^b$ and $Y^b$ is an integer of 0 to 4. For example, when the sum of the number of amino acid residues in $X^b$ and $Y^b$ is an integer of 0, both $X^b$ and $Y^b$ must be single bonds; and when the sum of the number of amino acid residues in $X^b$ and $Y^b$ is an integer of 4, each of $X^b$ and $Y^b$ may be a divalent peptide group consisting of two amino acid residues, or $X^b$ may be a divalent peptide group consisting of three amino acid residues, and $Y^b$ may be a divalent peptide group consisting of one amino acid residue, or $X^b$ may be a divalent peptide group consisting of four amino acid residues, and $Y^b$ may be a single bond.

The sum of the number of amino acid residues in $X^b$ and $Y^b$ is preferably an integer of 0 to 2, more preferably an integer of 0 to 1, or most preferably zero. That is, most preferably, $X^b$ and $Y^b$ are both single bonds.

For example, when the sum of the number of amino acid residues in $X^b$ and $Y^b$ is an integer of 2, $X^b$ may be a divalent peptide group consisting of two amino acid residues, and $Y^b$ may be a single bond, each of $X^b$ and $Y^b$ may independently be a divalent peptide group consisting of one amino acid residue, or $X^b$ may be a single bond, and $Y^b$ may be a divalent peptide group consisting of two amino acid residues.

When the sum of the number of amino acid residues in $X^b$ and $Y^b$ is an integer of 1, $X^b$ may be a divalent peptide group consisting of one amino acid residue, and $Y^b$ may be a single bond, or $X^b$ may be a single bond, and $Y^b$ may be a divalent peptide group consisting of one amino acid residue. In a preferred embodiment, $X^b$ is a single bond, and $Y^b$ is a residue of alanine, leucine or methionine, or $X^b$ is a residue of alanine, leucine or methionine, and $Y^b$ is a single bond.

"Cancer antigen peptide B" is an MHC class I-restricted WT1 peptide consisting of 7 to 30 amino acid residues, or an altered form thereof which is capable of inducing CTLs. Cancer antigen peptide B binds to $Y^b$ shown in formula (2) (or formula (1-2)) via an amino group of its N-terminal amino acid residue, and binds to OH shown in formula (2) via a carbonyl group of its C-terminal amino acid residue.

"Cancer antigen peptide C" is an MHC class I-restricted WT1 peptide consisting of 7 to 30 amino acid residues including one cysteine residue, or an altered form of the peptide which is capable of inducing CTLs, or an MHC class II-restricted WT1 peptide consisting of 7 to 30 amino acid residues including one cysteine residue, or an altered form of the peptide which is capable of inducing helper T cells. When $R^1$ is cancer antigen peptide C, a thioether group of a cysteine residue of the cancer antigen peptide C binds to the thioether group in formula (1). In the compound of formula (1), cancer antigen peptide C has a different amino acid sequence from cancer antigen peptide A.

Cancer antigen peptide C has least one cysteine residue in its amino acid sequence, wherein the number of cysteine residue is preferably 1 to 3, more preferably 1 to 2, or most preferably one.

In an embodiment, $R^1$ is cancer antigen peptide B or cancer antigen peptide C, and formula (1) represents a compound in the form of a heterodimer. In contrast to a homodimer which means a dimerized product of the same peptide monomers, a heterodimer means a dimerized product of different peptide monomers.

"Cancer antigen peptide D" is an MHC class II-restricted WT1 peptide consisting of 7 to 30 amino acid residues, or an altered form thereof which is capable of inducing helper T cells.

As used herein, the term "WT1 peptide", which is synonymous with "partial peptide of WT1 protein", refers to a peptide consisting of contiguous amino acid residues of the amino acid sequence of human WT1 protein of SEQ ID NO: 1.

The term "MHC class I-restricted" means an ability of a peptide to bind to a Major Histocompatibility Complex (MHC) class I molecule and induce CTLs.

MHC of human is called human leukocyte-type antigen (HLA). HLA Molecules corresponding to MHC class I-molecules include HLA-A, B, Cw, F and G subtypes. Restriction to HLA-A, HLA-B, or HLA-Cw is preferred as the restriction to MHC class I of an "MHC class I-restricted" peptide.

Allelic polymorphism is known for each HLA subtype. For HLA-A, 27 or more types of polymorphism including HLA-A1, HLA-A0201, and HLA-A24 are known. For HLA-B, 59 or more types of polymorphism including HLA-B7, HLA-B40, and HLA-B4403 are known. For HLA-Cw, 10 or more types of polymorphism including HLA-Cw0301, HLA-Cw0401, and HLA-Cw0602 are known. Among such polymorphism, HLA-A0201 and HLA-A24 are preferred.

The term "MHC class I-restricted WT1 peptide" as used herein refers to a WT1 peptide which is capable of binding to an MHC class I molecule in vitro and/or in vivo to form a complex which is recognizable by precursor T cells. Upon recognizing the complex, precursor T cells differentiate into CTLs. (Thus, an MHC class I-restricted WT1 peptide has an ability to induce CTLs.) The "MHC class I-restricted WT1 peptide" is often herein referred to as "WT1 killer peptide". The "MHC class I-restricted WT1 peptide" may consists of a sequence of any number of amino acids of any type, so long as it functions as the "MHC class I-restricted WT1 peptide" as defined above. However, the longer a peptide chain is, the more susceptible it may be to degradation by a proteolytic enzyme. Also, too small peptide may not successfully be caught in a peptide-binding groove of an MHC class I molecule. The "MHC class I-restricted WT1 peptide" typically consists of 7 to 30 amino acid residues, preferably 7 to 15 amino acid residues, more preferably 8 to 12 amino acid residues, still more preferably 8 to 11 amino acid residues, or most preferably 8 or 9 amino acid residues.

"MHC Class I-restricted WT1 peptide" consisting of 7-12 amino acid residues, or preferably 9 amino acid residues is herein often referred to as "MHC class I-restricted WT1 epitope". The term "MHC class I-restricted WT1 epitope" refers to a peptide corresponding to part of a peptide complexed with an MHC class I molecule, which part is to be presented as an epitope. Therefore, the "MHC class I-restricted WT1 peptide" includes such a peptide that may be degraded in vivo or in vitro by proteasome and/or protease to an "MHC class I-restricted WT1 epitope", and/or be cut or trimmed with Endoplasmic reticulum aminopeptidase 1 (ERAP1) off an "MHC class I-restricted WT1 epitope" having a certain appropriate peptide length. In a specific embodiment, an "MHC class I-restricted WT1 epitope" may be derived from an "MHC class I-restricted WT1 peptide" by degradation with proteasome and/or protease, followed by trimming (cutting) with ERAP1, wherein a C-terminal amino acid residue and an N-terminal amino acid residue of the "MHC class I-restricted WT1 epitope" may be determined by the action of proteasome/protease and ERAP1, respectively. However, an "MHC class I-restricted WT1 epitope" may be derived by any other way. ERAP1, Which is also referred to as ERAAP (ER aminopeptidase associated with antigen presentation), was formerly called A-LAP, PILS-AP or ARTS-1.

Accordingly, a preferable example of the "MHC class I-restricted WT1 peptide" is a peptide consisting of 7 to 30 amino acid residues corresponding to a product derived from an "MHC class I-restricted WT1 epitope" consisting of 7 to 12 amino acid residues through peptide chain elongation to an carbonyl group of its C-terminal amino acid residue with 1 to 23 amino acids.

The "MHC class I-restricted WT1 peptide" may preferably be a peptide consisting of an amino acid sequence selected from:

```
                                      (SEQ ID NO: 15)
            RMFPNAPYL, (SEQ ID NO: 16)
            CMTWNQMNL, (SEQ ID NO: 18)
            ALLPAVPSL, (SEQ ID NO: 19)
            SLGFQQYSV, (SEQ ID NO: 20)
            RVPGVAPTL,
            and (SEQ ID NO: 21)
            VLDFAPPGA,
``` or a peptide consisting of an amino acid sequence that differs from the amino acid sequence selected from SEQ ID NOS: 15, 16, 18, 19, 20 and 21 by alteration of one or several amino acid residues. A peptide consisting of an amino acid sequence selected from SEQ ID NOS: 15, 16, 17, 18, 19, 20 and 21 is also preferable.

As used herein, the term "peptide comprising an amino acid sequence" refers to a peptide having a particular amino acid sequence, which may, as usually understood, optionally have extra sequence(s) of amino acid residue(s) attached to the N-terminal and/or C-terminal amino acid of the particular sequence. An "MHC class I-restricted WT1 peptide" as "cancer antigen peptide A" or "cancer antigen peptide B" may have an extra sequence of amino acid residue(s) attached preferably to its C-terminus. An "MHC class I-restricted WT1 epitope" may have an extra sequence of amino acid residue(s) attached preferably to its C-terminus.

As used herein, the term "altered peptide" refers to a peptide consisting of an amino acid sequence that differs from the amino acid sequence of the original peptide by alteration of one or several amino acid residues. In an altered peptide, one or several amino acid residues, for example, 1 to 9 amino acid residues, preferably 1 to 5, 1 to 4 or 1 to 3 amino acid residues, more preferably 1 to 2 amino acid residues, or most preferably one amino acid residue is deleted from, substituted in, and/or added (or inserted) to an amino acid sequence of an original peptide. The number of amino acid(s) deleted from an original peptide may preferably be 1 to 5, 1 to 4, or 1 to 3, more preferably 1 to 2, or most preferably one. The number of amino acid(s) added (or inserted) to an original peptide may preferably be 1 to 5, 1 to 4, or 1 to 3, more preferably 1 to 2, or most preferably one. Amino acid substitution for altering a peptide may be made at any position of amino acid residue in an original sequence with any type of amino acid. Conservative amino acid substitution is preferred. For example, substitution of Asp for Glu; Tyr for Phe; Ile for Leu; Ser for Ala; or Arg for His may be made. Amino acid addition or deletion may preferably be made at N- or C-terminus of a peptide. However, amino acid addition or deletion may be made internally. Amino acid addition or substitution may be addition of, or replacement with any of the twenty genetically encoded amino acids or even any non-natural amino acid.

When a killer peptide consists of an altered amino acid sequence, it is herein referred to as an "altered killer peptide". In an altered killer peptide, amino acid substitution may be made, specifically at amino acid position 1 (N-terminus), 2, 3 or 9 in a peptide consisting of nine amino acid residues. When an altered killer peptide has added (or inserted) amino acid residue(s), the number of added amino acid(s) is preferably 1 or 2, or more preferably one. Amino acid addition to C-terminus is preferred. When a killer peptide is altered by amino acid deletion, the number of deleted amino acid(s) is preferably one.

Each HLA subtype carries polymorphism. It is known that a peptide which can complex with a polymorphic sequence of an HLA antigen has a specific pattern of amino acid sequence (that is, binding motif) for binding to the polymorphic sequence of the HLA antigen. As a peptide which can bind to HLA-A24, a peptide consisting of 8 to 11 amino acid residues is known, which has Tyr, Phe, Met or Trp as amino acid at position 2, and Phe, Leu, Ile, Trp or Met as C-terminal amino acid (J. Immunol., 152, p 3913, 1994; J. Immunol., 155, p 4307, 1994; Immunogenetics, 41, p 178, 1995). Therefore, for example, a peptide consisting of nine amino acid residues may be altered by amino acid substitution to have Tyr, Phe, Met or Trp at position 2, and/or Phe, Leu, Ile, trp or Met at position 9 to give an altered peptide useful as an altered killer peptide. As a peptide which can bind to HLA-A0201, a peptide consisting of 8 to 11 amino acid residues is known, which has Leu or Met as an amino acid at position 2, and Val or Leu as C-terminal amino acid. Therefore, for example, a peptide consisting of nine amino acid residues may be altered by amino acid substitution to have Leu or Met at position 2, and/or Val or Leu at position 9 to give an altered peptide useful as an altered killer peptide.

Examples of altered killer peptides include:

```
                                        (SEQ ID NO: 22)
RYFPNAPYL as an altered killer peptide of (SEQ ID NO: 15)
RMFPNAPYL (WO 03/106682);

(SEQ ID NO: 23)
EMFPNAPYL, (SEQ ID NO: 24)
RLFPNAPYL, (SEQ ID NO: 25)
RMMPNAPYL, (SEQ ID NO: 26)
RMFPNAPYV;
or (SEQ ID NO: 27)
YMFPNAPYL (WO 2009/072610);

(SEQ ID NO: 17)
CYTWNQMNL as an altered killer peptide of (SEQ ID NO: 16)
CMTWNQMNL (WO 02/79253);
```

```
                                        -continued
                                        (SEQ ID NO: 28)
Xaa-Met-Thr-Trp-Asn-Gln-Met-Asn-Leu, (wherein Xaa is Ser or Ala),
or (SEQ ID NO: 29)
Xaa-Tyr-Thr-Trp-Asn-Gln-Met-Asn-Leu (wherein Xaa is Ser, Ala, Abu, Arg, Lys, Orn, Cit, Leu, Phe or Asn) (WO 2004/026897);

(SEQ ID NO: 30)
AYLPAVPSL as an altered killer peptide of (SEQ ID NO: 18)
ALLPAVPSL (WO 2003/106682);

(SEQ ID NO: 31)
FLGEQQYSV, (SEQ ID NO: 32)
SMGEQQYSV,
or (SEQ ID NO: 33)
SLMEQQYSV as an altered killer peptide of (SEQ ID NO: 19)
SLGEQQYSV (WO 2009/072610); or (SEQ ID NO: 34)
RYPGVAPTL as an altered killer peptide of (SEQ ID NO: 20)
RVPGVAPTL (WO 2003/106682).
```

In one embodiment, the compound of formula (1) may be any of:

the compound of formula (3):

$$\begin{array}{c} \text{CRMFPNAPYL (SEQ ID NO: 35),} \\ | \\ \text{CMTWNQMNL (SEQ ID NO: 16)} \end{array} \quad (3)$$

(wherein C—C shown in the formula means that the C residues are linked together by a disulfide bond), the compound of formula (4):

$$\begin{array}{c} \text{CRMFPNAPYL (SEQ ID NO: 35)} \\ | \\ \text{CYTWNQMNL (SEQ ID NO: 17)} \end{array} \quad (4)$$

(wherein C—C shown in the formula means that the C residues are linked together by a disulfide bond), a compound of formula (5):

$$\begin{array}{c} \text{CCYTWNQMNL (SEQ ID NO: 70),} \\ | \\ \text{CMTWNQMNL (SEQ ID NO: 16)} \end{array} \quad (5)$$

(wherein C—C shown in the formula means that the C residues are linked together by a disulfide bond), a compound of formula (6):

$$\begin{matrix} \text{CCMTWNQMNL} & \text{(SEQ ID NO: 71),} \\ | & \\ \text{CYTWNQMNL} & \text{(SEQ ID NO: 17)} \end{matrix} \qquad (6)$$

(wherein C—C shown in the formula means that the C residues are linked together by a disulfide bond), a compound of formula (7):

$$\begin{matrix} \text{CALLPAVPSL} & \text{(SEQ ID NO: 72),} \\ | & \\ \text{CMTWNQMNL} & \text{(SEQ ID NO: 16)} \end{matrix} \qquad (7)$$

(wherein C—C shown in the formula means that the C residues are linked together by a disulfide bond), a compound of formula (8):

$$\begin{matrix} \text{CALLPAVPSL} & \text{(SEQ ID NO: 72),} \\ | & \\ \text{CYTWNQMNL} & \text{(SEQ ID NO: 17)} \end{matrix} \qquad (8)$$

(wherein C—C shown in the formula means that the C residues are linked together by a disulfide linkage), a compound of formula (9):

$$\begin{matrix} \text{CSLGEQQYSV} & \text{(SEQ ID NO: 73),} \\ | & \\ \text{CMTWNQMNL} & \text{(SEQ ID NO: 16)} \end{matrix} \qquad (9)$$

(wherein C—C shown in the formula means that the C residues are linked together by a disulfide bond), a compound of formula (10):

$$\begin{matrix} \text{CSLGEQQYSV} & \text{(SEQ ID NO: 73),} \\ | & \\ \text{CYTWNQMNL} & \text{(SEQ ID NO: 17)} \end{matrix} \qquad (10)$$

(wherein C—C shown in the formula means that the C residues are linked together by a disulfide bond), a compound of formula (11):

$$\begin{matrix} \text{CRVTPGVAPTL} & \text{(SEQ ID NO: 74),} \\ | & \\ \text{CMTWNQMNL} & \text{(SEQ ID NO: 16)} \end{matrix} \qquad (11)$$

(wherein C—C shown in the formula means that the C residues are linked together by a disulfide bond), a compound of formula (12):

$$\begin{matrix} \text{CRVPGVAPTL} & \text{(SEQ ID NO: 74),} \\ | & \\ \text{CYTWNQMNL} & \text{(SEQ ID NO: 17)} \end{matrix} \qquad (12)$$

(wherein C—C shown in the formula means that the C residues are linked together by a disulfide bond), a compound of formula (13):

$$\begin{matrix} \text{CVLDFAPPGA} & \text{(SEQ ID NO: 75),} \\ | & \\ \text{CMTWNQMNL} & \text{(SEQ ID NO: 16)} \end{matrix} \qquad (13)$$

(wherein C—C shown in the formula means that the C residues are linked together by a disulfide bond), or a compound of formula (14):

$$\begin{matrix} \text{CVLDFAPPGA} & \text{(SEQ ID NO: 75),} \\ | & \\ \text{CYTWNQMNL} & \text{(SEQ ID NO: 17)} \end{matrix} \qquad (14)$$

(wherein C—C shown in the formula means that the C residues are linked together by a disulfide bond).

The term "MHC class II-restricted" means the ability of a peptide to bind to an MHC class II molecule and induce helper T cells.

HLA Corresponding to MHC class II-molecules has subtypes including HLA-DR, DQ and DP subtypes. Restriction to HLA-DR, HLA-DQ, or HLA-DP is preferred as the restriction to MHC class II of an "MHC class II-restricted" peptide. Restriction to a subtype selected from the following is more preferred: DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602 and DRB5*0102. Restriction to a subtype selected from DRB1*0101, DRB1*0405, DRB1*1502, DPB1*0201, DPB1*0202 and DQB1*0601 is most preferred.

The term "MHC class II-restricted WT1 peptide" as used herein refers to a WT1 peptide which is capable of binding to an MHC class II molecule in vitro and/or in vivo and inducing helper T cells. (Thus, an MHC class II-restricted WT1 peptide has an ability to induce helper T cells.) The "MHC class II-restricted WT1 peptide" is often herein referred to as "WT1 helper peptide". The "MHC class II-restricted WT1 peptide" may consists of a sequence of any number of amino acids of any type, so long as it functions as the "MHC class II-restricted WT1 peptide" as defined above. However, the longer a peptide chain is, the more susceptible it may be to degradation by a proteolytic enzyme. Also, too small peptide may not successfully be caught in a peptide-binding groove of an MHC class II molecule. The "MHC class II-restricted WT1 peptide" typically consists of 7 to 30 amino acid residues, preferably 9 to 30 amino acid residues, more preferably 10 to 25 amino acid residues, still more preferably 12 to 24 amino acid residues, or most preferably 15 or 22 amino acid residues.

The inventors of the present invention have found that amino acid sequences of WT1 helper peptides commonly have a motif: KLSHL from amino acid sequence of WT1 protein. The motif: KLSHL corresponds to the amino acid sequence at positions 336-340 of SEQ ID NO: 1. Thus, in an embodiment of the present invention, an "MHC class II-restricted WT1 peptide" is a partial peptide of WT1 protein consisting of an amino acid sequence of 9 to 30 amino acid residues including the motif: KLSHL as part thereof, or a peptide consisting of an amino acid sequence that differs from the amino acid sequence of the partial peptide by alteration of one or several amino acid residues and has an ability to induce helper T cells.

In another embodiment of the present invention, an "MHC class II-restricted WT1 peptide" is a partial peptide of WT1 protein consisting of an amino acid sequence of 10 to 25 amino acid residues, 12 to 24 amino acid residues, or 15 to 22 amino acid residues comprising the motif: KLSHL as part thereof, or a peptide consisting of an amino acid sequence that differs from the amino acid sequence of the partial peptide by alteration of one or several amino acid residues and has an ability to induce helper T cells.

As defined above, the term "peptide comprising an amino acid sequence" refers to a peptide having a particular amino acid sequence, which may, as usually understood, optionally have extra sequence(s) of amino acid residue(s) attached to the N-terminal and/or C-terminal amino acid of the particular sequence. Therefore, when a partial peptide of WT1 protein has an amino acid sequence of 9 to 30 amino acid residues, 10 to 25 amino acid residues, 12 to 24 amino acid residues, or 15 to 22 amino acid residues including the motif: KLSHL as part thereof, the partial peptide of WT1 protein may be a peptide corresponding to part of the amino acid sequence of SEQ ID NO: I consisting of the motif: KLSHL and sequence(s) of necessary number of amino acid residues directly attached to the N-terminus and/or C-terminus of the motif. Specifically, such a partial peptide may correspond to an amino acid sequence consisting of contiguous 9 to 30 amino acids, 10 to 25 amino acids, 12 to 24 amino acids, or 15 to 22 amino acids including the motif: KLSHL from SEQ ID NO: 69, which corresponds to the sequence of amino acids 311-365 in SEQ ID NO: 1.

The amino acid sequence at positions 311-365 of SEQ ID NO: 1 (corresponding to the amino acid sequence of SEQ ID NO: 69) is as follows:

```
Val Arg Ser Ala Ser Glu Thr Ser Glu Lys Arg Pro Phe Met Cys Ala Tyr Pro Gly Cys
            315                 320                 325                 330
Asn Lys Arg Tyr Phe Lys Leu Ser His Leu Gln Met His Ser Arg Lys His Thr Gly Glu
            335                 340                 345                 350
Lys Pro Tyr Gln Cys Asp Phe Lys Asp Cys Glu Arg Arg Phe Ser
            355                 360                 365
```

Examples of peptides useful as the "MHC class II-restricted WT1 peptide" include a peptide comprising an amino acid sequence selected from:

AYPGCNKRYFKLSHL, (SEQ ID NO: 2)

YPGCNKRYEKLSHLQ, (SEQ ID NO: 3)

PGCNKRYFKLSHLQMHSRKHTG, (SEQ ID NO: 4)

PGCNKRYFKLSHLQMHSRK, (SEQ ID NO: 5)

GCNKRYFKLSHLQMHSRK, (SEQ ID NO: 6)

CNKRYFKLSHLQMHSRK, (SEQ ID NO: 7)

NKRYFKLSHLQMHSRK, (SEQ ID NO: 8)

KRYFKLSHLQMHSRK, (SEQ ID NO: 9)

KRYFKLSHLQMHSRKH, (SEQ ID NO: 10)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)

and

KLSHLQMHSRKHTGE, (SEQ ID NO: 14)

or a peptide consisting of an amino acid sequence that differs from the amino acid sequence selected from SEQ ID NOS: 2-14 by alteration of one or several amino acid residue and has an ability to induce helper T cells.

Further examples of peptides useful as the "MHC class II-restricted WT1 peptide" include a peptide comprising an amino acid sequence selected from:

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

AYFGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

-continued

RYFKLSHLQMHSRKHT, (SEQ ID NO: 48)

RYFKLSHLQMHSRKHTGE, (SEQ ID NO: 49)

KLSHLQMHSRKH, (SEQ ID NO: 50)

YPGCNKRYFKLSHLQMHSRK, (SEQ ID NO: 51)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

NKRYFKLSHL, (SEQ ID NO: 64)

KLSHLQMHSRKHTG, (SEQ ID NO: 65)

KLSHLQMHSRKHT, (SEQ ID NO: 66)

KLSHLQMHSRK, (SEQ ID NO: 67)
and

KLSHLQMHSR, (SEQ ID NO: 68)

or a peptide consisting of an amino acid sequence that differs from the amino acid sequence selected from SEQ ID NOS: 39-68 by alteration of one or several amino acid residue and has an ability to induce helper T cells.

An MHC class II-restricted WT1 peptide may complex with an MHC class II molecule in any of HLA-DR, HLA-DQ or HLA-DP subclass. In a preferred embodiment of the present invention, an MHC class II-restricted WT1 peptide induces helper T cells by binding to an MHC class II molecule selected from DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602 and DRB5*0102. More preferably, an MHC class II-restricted WT1 peptide induces helper T cells by binding to an MHC class II molecule selected from DRB1*0101, DRB1*0405, DRB1*1403, DRB1*1502, DPB1*0201, DPB1*0202, DPB1*0901, DQB1*0301, DQB1*0601 and DRB5*0102. Most preferably, an MHC class II-restricted WT1 peptide induces helper T cells by binding to an MHC class II molecule selected from DRB1*0101, DRB1*0405, DRB1*1502, DPB1*0201, DPB1*0202 and DQB1*0601.

A helper peptide consisting of an altered amino acid sequence is herein referred to as an "altered helper peptide". If a partial peptide of WT1 protein useful as a WT1 helper peptide consisting of an amino acid sequence of 9 to 30 amino acid residues comprising the sequence: KLSHL is altered, the altered peptide preferably has modification in amino acid residue(s) out of the sequence: KLSHL.

If a helper peptide consisting of an amino acid sequence of nine amino acid residues including a binding motif to HLA-DRB1*0405 is altered by amino acid substitution, substitution may preferably be made at amino acid position 1, 4, 6 and/or 9. In a preferred embodiment, a helper peptide consisting of a sequence of nine amino acid residues including a binding motif to HLA-DRB1*0405 may be altered by amino acid substitution to have amino acid residue(s) selected from:

phenylalanine, tryptophan, valine, isoleucine, leucine or methionine at position 1;
valine, isoleucine, methionine, aspartic acid and glutamic acid at position 4;
asparagine, serine, threonine, glutamine, lysine and aspartic acid at position 6; and/or
aspartic acid, glutamic acid and glutamine at position 9.

A peptide may have modification in amino acid residue(s) in its sequence. Modification may be made by a conventional way, for example by esterification, alkylation, halogenation, phosphorylation, sulfonation, or amidation on a functional group in an amino acid residue. Amino acid modification in a peptide can also be addition of an amino acid, a peptide, or an analog thereof, or other moiety to N-terminus and/or C-terminus of a peptide. A peptide modified by such addition of a moiety may undergo, for example, biological enzymatic decomposition or intracellular processing, and be converted to a peptide capable of complexing with an MHC class I molecule or an MHC class II molecule. A peptide may be modified by addition of such a moiety that would modulate solubility of the peptide, stabilize the peptide against, for example, proteolytic degradation, direct the peptide to a specific tissue or organ, or improve capturing of the peptide by antigen presenting cells. A peptide may be altered by addition of a different peptide which may be a different killer or helper peptide.

In a peptide, an amino group of its N-terminal amino acid or a carboxyl group of its C-terminal amino acid may be modified. The amino group may be modified, for example by addition of one to three groups selected from $C_{1-6}$-alkyl, phenyl, cycloalkyl, or acyl such as $C_{1-6}$-alkanoyl, phenyl-$C_{1-6}$-alkanoyl, $C_{5-7}$-cycloalkyl-carbonyl, $C_{1-6}$-alkylsulfonyl, phenylsulfonyl, $C_{2-6}$-alkoxy-carbonyl, phenyl-alkoxycarbonyl, $C_{5-7}$-cycloalkoxy-carbonyl, or phenoxycarbonyl. The carboxyl group of the C-terminal amino acid may be modified, for example by conversion to an ester, such as a $C_{1-6}$-alkyl ester, a phenyl-$C_{0-6}$-alkyl ester, or a $C_{5-7}$-cycloalkyl ester, or to an amide such as an unsubstituted amide, a mono- or di-$C_{1-6}$-alkylamide, a mono- or di-phenyl-$C_{0-6}$-alkylamide, or a di-substituted amide wherein the two substituents forms together with the nitrogen atom they attach to a 5- to 7-membered azacycloalkane.

In a peptide of the present invention, a bond between amino acid residues may be peptide bond or other type of bond such as carbon-carbon bond, carbon-nitrogen bond, or carbon-sulfur bond. A peptide of the present invention may comprise one or more D-amino acid residues.

The above description about modification in a peptide is illustrative only, and variations thereof within the scope of the present invention would be obvious to a person skilled in the art. Such a modified peptide would be prepared, tested or used by an ordinarily skilled person in the art.

The ability of a peptide to induce CTLs or helper T cells can be confirmed by a conventional method. Induction of CTLs can be confirmed, for example by counting CTLs by HLA tetramer method (Int. J. Cancer: 100, 565-570 (2002)) or limiting dilution method (Nat. Med.: 4, 321-327 (1998)). Induction of CTLs by an HLA-A24-restricted peptide may also be confirmed by using an HLA-A24 mouse model as described in WO 02/47474 or Int. J. Cancer: 100, 565-570 (2002). Induction of helper T cells can be confirmed, for example by a method as described in Cancer Immunol. Immunother. 51: 271 (2002) or in the Example section herein.

In another aspect, the present invention provides a polynucleotide encoding a WT1 peptide or an altered WT1 peptide (hereinafter also referred to as WT1 polynucleotide) The polynucleotide of the present invention can be DNA or RNA. The polynucleotide of the present invention has a nucleotide sequence corresponding to an amino acid sequence of a WT1 peptide or an altered WT1 peptide the polynucleotide encodes. The polynucleotide of the present invention may be synthesized by a method for DNA or RNA synthesis, or PCR.

The present invention includes a polynucleotide which is able to hybridize to a complementary sequence of a polynucleotide encoding a WT1 peptide or an altered WT1 peptide under a stringent condition, and encodes a peptide having a similar ability of inducing CTLs or helper T cells to a WT1 peptide or an altered WT1 peptide of the present invention. The hybridization under a stringent condition may be conventional hybridization as described in Sambrook J., Frisch E. F., Maniatis T., Molecular Cloning 2nd edition, Cold Spring Harbor Laboratory press. A "stringent condition" may be created, for example in a solution of 6×SSC (in this regard, 10×SSC contains 1.5 M NaCl, and 0.15 M trisodium citrate) with 50% formamide at 45° C. for forming a hybrid, and in a solution of 2×SSC for washing a hybrid (Molecular Biology, John Wiley & Sons, N.Y. (1989), 6.3.1-6.3.6).

In another aspect, the present invention provides an expression vector comprising a polynucleotide of the present invention (hereinafter also referred to as a WT1 expression vector). The expression vector of the present invention may be of any appropriate type, and have any appropriate sequence outside a sequence of a polynucleotide of the present invention, depending on type of a host to be transfected with the vector or any other specific factors. The vector may be a plasmid, a phage vector, or a viral vector. For transfection to E. coli, a plasmid vector such as pUC118, pUC119, pBR322 or pCR3, or a phage vector such as λZAPII or λgt11 may be used. For transfection to yeast, pYES2 or pYEUra3 may be used. For transfection to insect cells, pAcSGHisNT-A may be used. For transfection to animal cells, a plasmid vector such as pKCR, pCDM8, pGL2, pcDNA3.1, pRc/RSV or pRc/CMV, or a viral vector such as a retroviral vector, an adenoviral vector, or an adeno-associated viral vector may be used. A vector for the present invention may further comprise a promotor for expression induction, a gene coding a signal sequence, a marker gene for selection, or a terminator. A vector for the present invention may also comprise a sequence encoding a tag such as thioredoxin, a His tag or GST (glutathione S-transferase) so that a protein is expressed with a tag fused thereon for facilitation of isolation or purification of the protein. Such a vector may comprise an appropriate promotor depending on a host to be transfected with the vector, and can be a GST-fused protein expression vector (for example pGEX4T), a vector comprising a sequence of a tag such as Myc or His (for example, pcDNA3.1/Myc-His), or an expression vector for a protein fused to thioredoxin or a His tag (for example, pET32a).

The expression vector of the present invention expresses in vitro or in vivo a WT1 peptide or an altered WT1 peptide capable of inducing WT1-specific CTLs or helper T-cells and, therefore, is useful for treatment or prevention of a cancer.

In a further aspect, the present invention provides an antibody against a peptide or polynucleotide of the present invention (hereinafter also referred to as WT1 antibody). The antibody may be polyclonal or monoclonal, and can be prepared in accordance with a conventional method for preparation of a polyclonal or monoclonal antibody (Current protocols in Molecular Biology edit. Ausubel et al. (1987) Publish. John Wiley and Sons. Section 11.12-11.13, Antibodies; A Laboratory Manual, Lane, H, D. et al (Ed.), Cold Spring Harber Laboratory Press, New York 1989). The antibody of the present invention can be obtained as an antibody which recognizes a peptide of the present invention, or an antibody which recognizes and neutralizes a peptide of the present invention, from an animal immunized by a conventional method with a peptide of the present invention. The antibody of the present invention can be used in affinity chromatography, or in immunological diagnosis based, for example, on immunoblotting, radioimmunoassay (RIA), enzyme-linked immunosorbent assay (ELISA), or fluorescent or luminescent immunoassay, for a cancer, especially a cancer associated with WT1 gene expression or an elevated level of WT1 gene expression.

A peptide or compound of the present invention, or an intermediate peptide for the synthesis thereof may be synthesized in accordance with a method described in the Example section herein or by using a conventional technique for peptide synthesis as described, for example, in Peptide Synthesis, Interscience, New York, 1966; The Proteins, Vol 2, Academic Press Inc., New York, 1976; peptide synthesis, Maruzen Co., LTD., 1975; Basics and Experiment of Peptide Synthesis, Maruzen Co., LTD., 1985; or Development of Pharmaceutical Product subsequent vol. 14, Peptide Synthesis, Hirokawa Shoten, 1991. Examples of such a technique include solid phase synthesis by Fmoc method or Boc method, or liquid phase synthesis by sequential condensation of Boc-amino acid or Z-amino acid in a liquid phase (wherein Fmoc means 9-fluorenylmethoxycarbonyl, Boc means t-butoxycarbonyl, and Z means benzyloxycarbonyl). A peptide of the present invention may be obtained by a genetic technique by using a nucleotide sequence encoding the peptide in accordance with a conventionally known method as described, for example, in Molecular Cloning, T. Maniatis et al., CSH Laboratory (1983), DNA Cloning, D M. Glover, IRL PRESS (1985).

The compound of formula (1) of the present invention can be prepared from two different MHC class I-restricted WT1 peptides, or from an MHC class I-restricted WT1 peptide and an MHC class II-restricted WT1 peptide, by linking the peptides by a disulfide bond (WO 2014/157692).

In the course of the synthesis of a compound of formula (1), a functional group on an intermediate compound, such as amino, carboxyl or mercapto may be protected with an appropriate protecting group, or deprotected as needed by a conventional technique. For information about such a protecting group, or a protection or deprotection method, "Protective Groups in Organic Synthesis 2nd Edition (John Wiley & Sons, Inc.; 1990)" may be referred to. As a protecting group for mercapto, an acetamidomethyl group or a trityl group may be useful.

When a compound of formula (1) of the present invention includes a disulfide bond, the linkage is formed between two different, cysteine-comprising peptide components in the compound, or between a cysteine-comprising peptide component and a cysteine residue in the compound. Such a disulfide bond can be formed by a method as described, for example, in Peptide Synthesis, Interscience, New York, 1966; The Proteins, Vol. 2, Academic Press Inc., New York, 1976; peptide synthesis, Maruzen Co., LTD., 1975; Basics and Experiment of peptide synthesis, Maruzen Co., LTD., 1985; or Development of Pharmaceutical Product sequential vol. 14, Peptide Synthesis, Hirokawa Shoten, 1991.

Specifically, for preparing a compound having a disulfide bond (a disulfide compound) of the present invention from a peptide having one cysteine residue, the peptide may be subjected to a deprotection reaction for removal of any protecting groups on functional groups including mercapto on the cysteine residue, and then treated in an inert solvent under an oxidative condition for forming a disulfide bond. A disulfide compound may also be prepared from two different, mercapto-having intermediates by treating them in an appropriate solvent under an oxidative condition. Oxidative conditions for disulfide bond formation are known in the field of peptide synthesis. For example, a known method of iodine oxidation, air oxidation under an alkaline condition, or oxidation by an oxidizing agent under an alkaline or acidic condition may be used for forming a disulfide bond in the present invention. As an oxidizing agent, iodine, dimethyl sulfoxide (DMSO), or potassium ferricyanide may be used. As a solvent for the reaction, water, acetic acid, methanol, chloroform, DMF, or DMSO, or a mixture thereof may be used. Such an oxidative condition often gives a product in the form of a mixture of symmetric and asymmetric disulfide compounds. A desired asymmetric disulfide compound may be recovered or purified by an appropriate chromatographic method or recrystallization. A mercapto group may be activated for disulfide bond formation by conversion of the group to an Npys group (3-nitro-2-pyridinesulphenyl group). For forming a disulfide bond on a certain mercapto group on an intermediate, the group may be activated by 2,2'-dithiobis(5-nitropyridine) in advance of coupling with another intermediate compound (Tetrahedron Letters. Vol. 37. No. 9, pp. 1347-1350).

The methods as described above may be useful for preparing a disulfide compound from a peptide having more than one cysteine residue. In that case, however, a mixture of different disulfide compounds having disulfide bonds between different cysteine residues may be formed. For selectively preparing a product dimerized by a disulfide bond between specific positions of monomers, different protecting groups can be used in combination for protection of functional groups on the cysteine residues. Examples of such combination of protecting groups include a combination of MeBzl (methylbenzyl) and Acm (acetamidomethyl); Trt (trityl) and Acm; Npys (3-nitro-2-pyridylthio) and Acm group; and S-Bu-t (S-tert-butyl) and Acm. For example, when a peptide protected with a combination of MeBzl and Acm is used for selective disulfide bond formation, all the MeBzl protecting groups, and the Acm protecting groups on functional groups on amino acid residues other than certain cysteine residues may be removed in the first step. Then, by treating the peptide monomer in a solution under air oxidation condition, a disulfide bond can be formed between selectively deprotected cysteine residues of the monomers. Then, through removal of remaining Acm protecting groups and treatment under oxidative condition with iodine, a further disulfide bond can be formed on the newly deprotected cysteine residues.

A peptide, compound or intermediate synthesized for the present invention may be purified by any purification method know in the art or in the field of peptide chemistry. Examples of such a purification technique include various types of chromatography (e.g., silica gel column chromatography, ion exchange column chromatography, gel filtration or reversed-phase chromatography), and recrystallization from a solvent, for example an alcohol, such as methanol, ethanol or 2-propanol; an ether, such as diethyl ether; an ester, such as ethyl acetate; an aromatic hydrocarbon, such as benzene or toluene; a ketone, such as acetone; a hydrocarbon, such as hexane; an aprotic solvent, such as dimethylformamide or acetonitrile; water; or a mixture thereof. For further useful purification methods, reference can be made, for example, to Jikken Kagaku Kouza (The Chemical Society of Japan ed., Maruzen) vol. 1. Purification methods for disulfide compounds are also described in Peptide Synthesis, Interscience, New York, 1966; peptide synthesis, Maruzen Co., LTD., 1975; Basics and Experiment of peptide synthesis, Maruzen Co., LTD., 1985; or Development of Pharmaceutical Product sequential vol. 14, Peptide Synthesis, Hirokawa Shoten, 1991. Purification by HPLC is preferred.

A compound of formula (1) of the present invention may have one or more asymmetric centers. Such a compound can be prepared from a starting material (an amino acid) having corresponding asymmetric centers. Also, a compound of formula (1) can be obtained in a high optical purity by inclusion of an optical resolution step in a process for its synthesis. For example, in accordance with a diastereomer method for optical resolution, a compound of formula (1) or an intermediate product can be treated with an optically active acid (e.g., a monocarboxylic acid such as mandelic acid, N-benzyloxyalanine, or lactic acid, a dicarboxylic acid such as tartaric acid, o-diisopropylidenetartaric acid, or malic acid, or a sulfonic acid such as camphorsulfonic acid or bromocamphorsulfonic acid) in an inert solvent (e.g., an alcohol such as methanol, ethanol, or 2-propanol, an ether such as diethyl ether, an ester such as ethyl acetate, a hydrocarbon such as toluene, an aprotic solvent such as acetonitrile, or a mixture thereof) to form salts. For optically resolving a compound of formula (I) or an intermediate having an acidic functional group such as carboxyl, its salts can be formed with an optically active amine (e.g., an organic amine such as α-phenethylamine, kinin, quinidine, cinchonidine, cinchonine, or strychnine).

The salts may be formed at a temperature in the range from room temperature up to the boiling point of a solvent used. For obtaining a product in a highly optically pure form, it may be desirable to raise the temperature to around the boiling point of the solvent for a period of time. Salts formed are crystallized, and then filtered, optionally with cooling for an improved yield. An optically active acid or amine used for the salt formation may be used in an amount of about 0.5 to about 2.0 equivalents, preferably about 1 equivalent, relative to the amount of a compound to optically resolve. A crystalline product may optionally be further purified by recrystallization from an inert solvent (e.g., an alcohol such as methanol, ethanol, or 2-propanol, an ether such as diethyl ether, an ester such as ethyl acetate, a hydrocarbon solvent such as toluene, an aprotic solvent such as acetonitrile, or a mixture thereof). A product recovered in the form of a salt may optionally be converted to a free base or acid by treatment with an acid or base.

The term "pharmaceutically acceptable salt" as used herein includes an acid addition salt and an base addition salt. The acid addition salt may be an inorganic acid salt, such as hydrochloride, hydrobromide, sulfate, hydroiodide, nitrate, or phosphate, or an organic acid salt such as citrate, oxalate, acetate, formate, propionate, benzoate, trifluoroacetate, maleate, tartrate, methanesulfonate, benzenesulfonate, or p-toluenesulfonate. The base addition salt may be a salt with an inorganic base, such as sodium salt, potassium salt, calcium salt, magnesium salt, or ammonium salt, a salt with an organic base, such as triethylammonium salt, triethanolammonium salt, pyridinium salt, or diisopropylammonium salt. The "pharmaceutically acceptable salt" also includes a salt with a basic or acidic amino acid, such as arginine, aspartic acid, or glutamic acid. The term "peptide" or "compound" used herein includes a peptide or compound in the form of a pharmaceutically acceptable salt, unless the context requires otherwise.

The present invention further includes a hydrate or a solvate such as an ethanol solvate of the peptide or the compound of formula (1) or a pharmaceutically acceptable salt thereof as described herein. The present invention also includes any stereoisomer such as a diastereomer or an enantiomer, and any crystalline form of the peptide or the compound as described herein.

When the peptide or a pharmaceutically acceptable salt thereof as described herein is used in combination with the compound of formula (1) or a pharmaceutically acceptable salt thereof as described herein, and optionally with a further active agent, they may be formulated in separate compositions or incorporated in a single composition. In an embodiment of the present invention, a WT1 helper peptide and a compound of formula (1) are incorporated in a single composition. In another embodiment, a WT1 helper peptide and a compound of formula (1) are formulated in separate compositions. A composition comprising either a compound of formula (1) or a WT1 helper peptide may be provided together with instructions of dosage and administration for use of the composition in combination with the other active agent. A composition comprising a compound of formula (1), and a composition comprising a WT1 helper peptide may be incorporated in a single kit. Such a kit may further comprise instructions of dosage and administration for use of the compositions in combination, or may be packaged. In administration of more than one active agent in combination, the agents may be administered on the same administration schedule or different administration schedules.

The peptide or the compound of formula (1), or a pharmaceutically acceptable salt thereof, or a combination thereof as described herein is useful in treatment or prevention (including prevention of recurrence) of a cancer, especially a cancer associated with WT1 gene expression or an elevated level of WT1 gene expression. For example, the peptide or the compound of formula (1), or a pharmaceutically acceptable salt thereof, or a combination thereof as described herein can be an active ingredient of a pharmaceutical composition (for example, a cancer vaccine), or a composition for inducing CTLs in cellular immunotherapy for a cancer.

The peptide, the compound of formula (1), a pharmaceutically acceptable salt thereof, or a combination thereof as described herein may be administered in combination with other drug(s) (hereinafter referred to as coadministration drug(s)).

In an embodiment, the peptide or the compound of formula (1), or a pharmaceutically acceptable salt thereof, or a combination thereof as described herein may be administered in combination with an "immunomodulator". As used herein, the term "immunomodulator" means any agent that controls transmission of costimulatory signals generated during T cell activation by antigen-presenting cells by interacting with molecules which are involved in the transmission of the costimulatory signals and are present on the antigen-presenting cells and/or T cells, as well as any agent that directly or indirectly controls function of molecules involved in establishment of immune tolerance (immunosuppression) in the immune system. Since a cancer antigen peptide is effective for increasing tumor-reactive CTLs in a tumor, it is potentially useful as an agent for coadministration with an immunomodulator, for lowering a necessary dose of an immunomodulator or reducing adverse event caused by an immunodulator. Thus, the present disclosure provides, through the use of a WT1 antigen peptide in combination with an immumomodulator, patients with a therapy having improved efficacy and safety.

The "immunomodulator" can be an agent in the form of an antibody, a nucleic acid, a protein, a peptide, or a small compound, but is not limited thereto. The "antibody" as the "immunomodulator" includes an antibody fragment. Examples of the antibody fragment include heavy and light chain variable regions of an antibody (VH and VL), F(ab')2, Fab', Fab, Fv, Fd, sdFv, and scFV. The "protein" as the "immunomodulator" means any protein other than antibodies. Examples of the "immunomodulator" include immune checkpoint inhibitors, costimulatory molecule agonists, immune activating agents, and low-molecular inhibitors.

The "immune checkpoint inhibitor" inhibits immunosuppressive effect induced by cancer cells or antigen presenting cells. Examples of the immune checkpoint inhibitor include, but are not limited to, agents against a molecule selected from the group consisting of: (1) CTLA-4 (e.g., ipilimumab and tremelimumab); (2) PD-1 (e.g., nivolumab, pembrolizumab, AMP-224, AMP-514 (MEDI0680), and pidilizumab (CT-011)); (3) LAG-3 (e.g., iMP-321 and BMS-986016); (4) BTLA; (5) KIR (e.g., IPH2101); (6) TIM-3; (7) PD-L1 (e.g., durvalumab (MEDI4736), MPDL3280A, BMS-936559, and avelumab (MSB0010718C)); (8) PD-L2; (9) B7-H3 (e.g., MGA-271); (10) B7-H4; (11) HVEM; (12) GAL9; (13) CD160; (14) VISTA; (15) BTNL2; (16) TIGIT; (17) PVR; (18) BTN1A1; (19) BTN2A2; (20) BTN3A2 (Nat Rev Drug Discov. 2013; 12: 130-146; Nikkei Medical Cancer Review 2014; 9; Nat Rev Immunol. 2014; 14: 559-69); and (21) CSFE-R.

The "costimulatory molecule agonist" enhances T cell activation by transmission of an auxiliary signal via a costimulatory molecule on the T cells and/or antigen presenting cells, and attenuates the immunosuppressive effect of cancer cells or antigen presenting cells. Examples of the costimulatory molecule agonist include, but are not limited to, agents against a molecule selected from the group consisting of: (1) 4-1BB; (2) 4-1BB-L; (3) OX40 (4) OX40-L; (5) GITR; (6) CD28; (7) CD40; (8) CD40-L; (9) ICOS; (10) ICOS-L; (11) LIGHT; and (12) CD27.

The "immune activating agent" efficiently stimulates killer T cells in the lymph nodes by directly or indirectly activating immune cells such as T cells and dendritic cells. Examples of the immune activating agent include, but are not limited to, Toll-like receptor (TLR) agonists, stimulator of interferon genes (STING) agonists, cytokines, and agents against heat shock protein (HSP).

Examples of the "Toll-like receptor (TLR) agonist" include, but are not limited to, TLR1/2 agonists, TLR2 agonists, TLR3 agonists (e.g., PolyI:C), TLR4 agonists (e.g., S-type lipopolysaccharide, paclitaxel, lipid A, and monophosphoryl lipid A), TLR5 agonists (e.g., flagellin), TLR6/2 agonists (e.g., MALP-2), TLR7 agonist, TLR7/8 agonists (e.g., gardiquimod, imiquimod, loxoribine, and resiquimod (R848)), TLR7/9 agonists (e.g., hydroxychloroquine sulfate), TLR8 agonists (e.g., motolimod (VTX-2337)), TLR9 agonists (e.g., CpG-ODN), and TLR11 agonists (e.g., profilin).

Examples of the "cytokine" include, but are not limited to, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (INF)-α, INF-β, INF-γ, SCF, GM-CSF, G-CSF, M-CSF, erythropoietin, thrombopoietin, macrophage inflammatory protein (MIP), and monocyte chemoattractant protein (MCP).

Examples of the "heat shock protein (HSP)" include, but are not limited to, HSP70, HSP90, HSP90α, HSP90β, HSP105, HSP72, and HSP40. Agents against a heat shock protein include HSP inhibitors. Examples of inhibitors to HSP90, for example, include, but are not limited to, tanespimycin (17-AAG), luminespib (AUY-922, NVP-AUY922), alvespimycin (17-DMAG) hydrochloride, ganetespib (STA-9090), BIIB021, onalespib (AT13387), geldanamycin, NVP-BEP800, SNX-2112 (PF-04928473), PF-4929113 (SNX-5422), KW-2478, XL888, VER155008, VER-50589, CH5138303, VER-49009, NMS-E973, PU-H71, HSP990 (NVP-HSP990) and KNK437.

Examples of the "low-molecular inhibitor" include, but are not limited to, histone deacetylase inhibitors, histone demethylase inhibitors, histone acetyltransferase inhibitors, histone methyltransferase inhibitors, DNA methyltransferase inhibitors, anthracycline antibiotics, platinum formulations, MAPK inhibitors, β-catenin inhibitors, STAT3 inhibitors, NF-kB inhibitors, JAK inhibitors, mTOR inhibitors, IDO inhibitors, COX-2 inhibitors, CXCR4 inhibitors, and arginase inhibitors.

Examples of the "histone deacetylase inhibitor" include, but are not limited to, vorinostat (SAHA, MKO683), entinostat (MS-275), panobinostat (LBH589), trichostatin A (TSA), mocetinostat (MGCDO103), BG45, BRD73954, belinostat (PXD101), romidepsin (FK228, depsipeptide), 4SC-202, HPOB, LMK-235, CAY10603, tasquinimod, TMP269, nexturastat A, rocilinostat (ACY-1215), RGFP966, RG2833 (RGFP109), scriptaid, tubastatin A, pracinostat (SB939), CUDC-101, M344, PCI-34051, dacinostat (LAQ824), tubastatinA hydrochloride, abexinostat (PCI-24781), CUDC-907, AR-42, sodium phenylbutyrate, resminostat, tubacin, quisinostat (JNJ-26481585) dihydrochloride, MC1568, givinostat (ITF2357), droxinostat, chidamide (C S055, HBI-8000), CHR-2485, CHR-3996, DAC-060, FRM-0334 (EVP-0334), MGCD-290, CXD-101 (AZD-9468), CG200745, arginine butyrate, sulforaphane, SHP-141, CUDC-907, YM753 (OBP-801), sodium valproate, apicidin, and CI994 (tacedinaline).

Examples of the "histone demethylase inhibitor" include, but are not limited to, GSK J4 HCl, OG-L002, JIB-04, IOX1, SP2509, ORY-1001 (RG-6016), GSK J1, ML324, and GSK-LSD1 2HCl.

Examples of the "histone acetyltransferase inhibitor" include, but are not limited to, C646, MG149, remodelin, and anacardic acid.

Examples of the "histone methyltransferase inhibitor" include, but are not limited to, pinometostat (EPZ5676), EPZ005678, GSK343, BIX01294, tazemetostat (EPZ6438), 3-deazaneplanocin A (DZNeP) HCl, UNC1999, MM-102, SGC0946, entacapone, EPZ015666, UNC0379, E1, MI-2 (menin-MLL inhibitor), MT-3 (menin-MLL inhibitor), PFI-2, GSK126, EPZ04777, BRD4770, GSK-2816126, and UNC0631.

Examples of the "DNA methyltransferase inhibitor" include, but are not limited to, decitabine, azatidine, RG108, thioguanine, zebularine, SGI-110, CC-486, SGI-1027, lomeguatrib, and procainamide hydrochloride.

The "anthracycline antibiotic" is intercalated between DNA strands to inhibit DNA relaxation. Examples of the anthracycline antibiotic include, but are not limited to, doxorubicin, liposomal doxorubicin, daunorubicin, pirarubicin, epirubicin, idarubicin, aclarubicin, amrubicin, aloin, and mitoxantrone.

Examples of the "platinum formulation" include, but are not limited to, cisplatin, carboplatin, miboplatin, nedaplatin, satraplatin (JM-126), oxaliplatin (ELOXATIN), triplatin tetranitrate, and DDS formulations thereof.

Examples of the "MAPK inhibitor" include, but are not limited to, SB203580, doramapimod (BTRB796), SB202190 (FHPI), LY2228820, VX-702, SB239063, pexmetinib (ARRY-614), PH-797804, VX-745, and TAK-715.

Examples of the "β-catenin inhibitor" include, but are not limited to, XAV-939, ICG-001, IWR-1-endo, Wnt-C59 (C59), LGK-974, KY02111, IWP-2, IWP-L6, WIKI4, and FH535.

Examples of the "STAT3 inhibitor" include, but are not limited to, S3I-201, Stattic, niclosamide, nifuroxazide, napabucasin (BBI608), cryptotanshinone, HO-3867, WHI-P154, FLLL32, STA-21, WP1066, and SH-4-54.

Examples of the "NF-kB inhibitor" include, but are not limited to, QNZ (EVP4593), sodium 4-aminosalicylate, JSH-23, phenethyl caffeate, sodium salicylate, andrographolide, and SC75741.

Examples of the "JAK inhibitor" include, but are not limited to, ruxolitinib (INCB018424), tofacitinib (CP-690550) citrate, AZD1480, fedratinib (SAR302503, TG101348), AT9283, tyrphostin B42 (AG-490), momelotinib (CYT387), tofacitinib (CP-690550, tasocitinib), WP1066, TG101209, gandotinib (LY2784544), NVP-BSKS05 2HCl, baricitinib (LY3009104, INCB02850), AZ960, CEP-33779, pacritinib (SB1518), WHI-P154, XL019, S-ruxolitinib (INCB018424), ZM39923 HCl, decernotinib (VX-509), cerdulatinib (PRT062070, PRT2070), filgotinib (GLPG0634), FLLL32, peficitinib (ASP015K, JNJ-54781532), GLPG0634 analogue, Go6976, and Curcumol.

Examples of the "mTOR inhibitor" include, but are not limited to, sirolimus (rapamycin), deforolimus (AP23573, MK-8669), everolimus (RAD-001), temsirolimus (CCI-779, NSC683864), zotarolimus (ABT-578), biolimus A9 (umirolimus), AZD8055, KU-0063794, voxtalisib (XL765, SAR245409), MHY1485, dactolisib (BEZ235, NVP-BEZ235), PI-103, and torkinib (PP242).

Examples of the "IDO inhibitor" include, but are not limited to, NLG919, INCB024360 analog, indoximod (NLG-8189), and epacadostat (INCB024360).

Examples of the "COX-2 inhibitor" include, but are not limited to, valdecoxib, rofecoxib, carprofen, celecoxib, lumiracoxib, tolfenamic acid, nimesulide, niflumic acid, asaraldehyde, lornoxicam, sodium meclofenamate, amfenac sodium hydrate, diclofenac sodium, ketoprofen, ketorolac, naproxen sodium, indomethacin, ibuprofen, aspirin, mefenamic acid, bromfenac sodium, oxaprozin, zaltoprofen, and nepafenac.

Examples of the "CXCR4 inhibitor" include, but are not limited to, WZ811, plerixafor (AMD3100), and plerixafor 8HCl (AMD3100 8HCl).

The peptide or the compound of formula (1), or a pharmaceutically acceptable salt thereof, or a combination thereof as described herein may also be used in combination with one or more drugs selected from the group consisting of "hormone therapy agent", "immunotherapeutic agent", "biopharmaceutical", "cell growth factor", "cell growth factor inhibitor", "cell growth factor receptor inhibitor", "radiotherapeutic agent", "auxiliary agent", and "chemotherapeutic agent". For example, one to five drugs, one to three drugs, or one drug selected from the above group of drugs may be used in combination with the peptide or the compound of formula (1), or a pharmaceutically acceptable salt thereof, or a combination thereof as described herein.

Examples of the "hormone therapy agent" include adrenal cortical hormone agents (e.g., steroidal anti-inflammatory agents, estrogen preparations, progesterone preparations, and androgen preparations), anti-estrogen agents, estrogen-controlling agents, estrogen synthesis inhibitors, anti-androgen agents, androgen-controlling agents, androgen synthesis inhibitors, LH-RH agonist preparations, LH-RH antagonist preparations, aromatase inhibitors, steroid-lactonase inhibitors, contraceptive pills, retinoids, and agents which delay metabolism of a retinoid.

Examples of the "hormone therapy agent" include fosfestrol, diethylstilbestrol, fluoxymesteral, chlorotrianisene, methyl testosterone, medroxyprogesterone acetate, megestrol acetate, chlormadinone acetate, cyproterone acetate, danazol, allylestrenol, gestrinone, mepartricin, raloxifene, ormeloxifene, levormeloxifene, tamoxifen citrate, toremifene citrate, iodoxyfene, pill formulations, mepitiostane, testololactone, aminoglutethimide, goserelin acetate, buserelin, leuprorelin, leuprolide, droloxifene, epitiostanol, ethinylestradiol sulfonate, estramustine, fadrozole hydrochloride, anastrozole, terorazole, ketoconazole, letrozole, exemestane, vorozole, formestane, flutamide, bicalutamide, nilutamide, enzalutamide, mifepristone, finasteride, dexamethasone, prednisolone, betamethasone, triamcinolone, abiraterone, liarozole, bexarotene, and DN101.

Examples of the "immunotherapeutic agent" include picibanil, krestin, sizofiran, lentinan, ubenimex, inLerferon (IFN)-α, interferon (IFN)-β, interferon (IFN)-γ, interleukin, macrophage colony stimulating factor, granulocyte-colony stimulating factor, erythropoietin, lymphotoxin, BCG vaccine, *Corynebacterium parvum*, levamisole, polysaccharide K, procodazole, anti-CTLA4 antibody, anti-PD-1 antibody, and TLR agonists (e.g., TLR7 agonists, TLR8 agonists, TLR9 agonists).

Examples of the "biopharmaceutical" include, but are not limited to, interleukin-2 (aldesleukin), interferon-α, interferon-β, interferon-γ, erythropoietin (EPO), granulocyte-colony stimulating factor (filgrastim), granulocyte-macrophage-colony stimulating factor (sargramostim), IL13-PE38QQR, Bacille Calmette-Guerin, levamisole, octreotide, CPG7909, Provenge, GVAX, Myvax, Favld, lenalidomide, trastuzumab, rituximab, gemtuzumab ozogamicin, alemtuzumab, endostatin, ibritumomab tiuxetan, tositumomab, cetuximab, zanolimumab, ofatumumab, HGS-ETR1, pertuzumab, M200, SGN-30, matuzumab, adecatumumab, denosumab, zalutumumab, MDX-060, nimotuzumab, MORAb-003, Vitaxin, MDX-101, MDX-010, DPC4 antibodies, NF-1 antibodies, NF-2 antibodies, Rb antibodies, p53 antibodies, WT1 antibodies, BRCA1 antibodies, BRCA2 antibodies, ganglioside (GM2), prostate specific antigens (PSA), α-fetoprotein (AFP), carcinoembryonic antigens (CEA), melanoma-associated antigens (MART-1, gap100, MAGE 1,3 tyrosine), papilloma virus E6 and E7 fragments, and DDS formulations thereof.

Regarding the "cell growth factor", "cell growth factor inhibitor" and "cell growth factor receptor inhibitor", cell growth factor may be any agent that promotes cell proliferation. For example, a cell growth factor may be a peptide that has a molecular weight of not more than 20,000 and can bind to a receptor and function at a low concentration.

Examples of the "cell growth factor" include, but are not limited to, epidermal growth factor (EGF), insulin-like growth factor (IGF (e.g., insulin, IGF-1, and IGF-2)), transforming growth factor (TGF (e.g., TGF-α and TGF-β)), nerve growth factor (NGF), brain-derived neurotrophic factor (BDNF), vascular endothelial growth factor (VEGF), colony stimulating factor (CSF (e.g., granulocyte-colony stimulating factor (G-CSF)), granulocyte-macrophage-colony stimulating factor (GM-CSF)), platelet-derived growth factor (PDGF), erythropoietin (EPO), fibroblast growth factor (FGF (e.g., acidic FGF, basic FGF, keratinocyte growth factor (KGK), and FGF-10)), hepatocyte growth factor (HGF), heregulin, and angiopoietin. The term "cell growth factor" is synonymous with the term "growth factor".

Examples of the "cell growth factor inhibitor" include, but are not limited to, epidermal growth factor inhibitors (EGF inhibitors), insulin-like growth factor inhibitors (IGF inhibitors), nerve growth factor inhibitors (NGF inhibitors), brain-derived neurotrophic factor inhibitors (BDNF inhibitors), vascular endothelial cell growth factor inhibitors (VEGF inhibitors), colony stimulating factor inhibitors (CSF inhibitors), platelet-derived growth factor inhibitors (PDGF inhibitors), erythropoietin inhibitors (EPO inhibitors), fibroblast growth factor inhibitors (FGF inhibitors), hepatocyte growth factor inhibitors (HGF inhibitors), heregulin inhibitors, and angiopoietin inhibitors. The term "cell growth factor inhibitor" is synonymous with the term "growth factor inhibitor".

Examples of the "cell growth factor receptor inhibitor" include, but are not limited to, epidermal growth factor receptor inhibitors (EGFR inhibitors), insulin-like growth factor receptor inhibitors (IGFR inhibitors), nerve growth factor receptor inhibitors (NGFR inhibitors), brain-derived neurotrophic factor receptor inhibitors (BDNFR inhibitors), vascular endothelial cell growth factor receptor inhibitors (VEGFR inhibitors), colony stimulating factor inhibitors (CSF inhibitors), platelet-derived growth factor receptor inhibitors (PDGFR inhibitors), erythropoietin receptor inhibitors (EPOR inhibitors), fibroblast growth factor receptor inhibitors (FGFR inhibitors), hepatocyte growth factor receptor inhibitors (HGFR inhibitors), heregulin receptor inhibitors, and angiopoietin receptor inhibitors. The term "cell growth factor receptor inhibitor" is synonymous with the term "growth factor receptor inhibitor".

Examples of the "radiotherapeutic agent" include, but are not limited to, radioactive materials and radiosensitizers.

The "auxiliary agent" is an agent used together with an anticancer agent for suppressing a side effect or vomiting caused by the anticancer agent. Examples of the "auxiliary agent" include, but are not limited to, aprepitant, ondansetron, lorazepam, dexamethasone, diphenhydramine, ranitidine, cimetidine, ranitidine, famotidine, cimetidine, Procrit, epoetin alfa, filgrastim, oprelvekin, leucovorin, and granulocyte-macrophage-colony stimulating factor (GM-CSF).

Examples of the "chemotherapeutic agent" include, but are not limited to, alkylating agents, platinum formulations, antimetabolites, topoisomerase inhibitors, DNA intercalators, antimitotic agents, antitumor antibiotics, plant-derived anticancer agents, epigenome drugs, immunomodulators, molecular targeted drugs, angiogenesis inhibitors, and other chemotherapeutic agents. Some typical examples of chemotherapeutic agent are listed below.

Examples of the "alkylating agent" include, but are not limited to, nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, procarbazine, ranimustine, estramustine sodium phosphate, triethylenemelamine, carmustine, lomustine, streptozocin, pipobroman, etoglucid, altretamine, ambamustine, dibrospidium hydrochloride, fotemustine, prednimustine, bendamustine, uramustine, semustine, pumitepa, ribomustin, temozolomide, treosulfan, trofosfamide, zinostatin stimalamer, adozelesin, cystemustine, bizelesin, mechlorethamine, uracil mustard, trabectedin, becaterin, chlormethine, mannosulfan, triaziquone, procarbazine, canfosfamide, nitrosoureas, and DDS formulations thereof.

Examples of the "platinum formulation" include, but are not limited to, cisplatin, carboplatin, miboplatin, nedaplatin, satraplatin, oxaliplatin, triplatin tetranitrate, and DDS formulations thereof.

Examples of the "antimetabolite" include, but are not limited to, antifolates, pyrimidine metabolism inhibitors, purine metabolism inhibitors, ribonucleotide reductase inhibitors, and nucleotide analogs.

Examples of the "antimetabolite" include, but are not limited to, mercaptopurine, 6-mercaptopurine riboside, thioinosine, methotrexate, pemetrexed, eoshitabin, enocitabine, cytarabine, cytarabine ocfosfate, ancitabine hydrochloride, 5-FU agents (e.g., fluorouracil, Carzonal, Bennan, Lunachol, Lunapon, tegafur, tegafur-uracil, tegafur-gimeracil-oteracil potassium (TS-1), UFT, doxifluridine, carmofur, gallocitabine, emitefur, and capecitabine), aminopterin, nelarabine, leucovorin calcium, Tabloid, butocine, folinate calcium, levofolinate calcium, cladribine, emitefur, fludarabine, gemcitabine, hydroxycarbamide, pentostatin, piritrexim, idoxuridine, mitoguazone, tiazofurine, ambamustine, bendamustine, floxuridine, leucovorin, hydroxyurea, thioguanine, asparaginase, bortezomib, raltitrexed, clofarabine, enocitabine, sapacitabine, azacytidine, sulfadiazine, sulfamethoxazole, trimethoprim, Liproxstatin-1, D4476, Xanthohumol, Epacadostat (INCB024360), Vidofludimus, P7C3, GMX1778 (CHS828), NCT-501, SW033291, Ro61-8048, and DDS formulations thereof.

Examples of the "topoisomerase inhibitor" include, but are not limited to, doxorubicin, daunorubicin, epirubicin, idarubicin, anthracenedione, mitoxantrone, mitomycin C, bleomycin, dactinomycin, plicatomycin, irinotecan, camptothecin, rubitecan, belotecan, etoposide, teniposide, topotecan, amsacrine, and DDS formulations thereof.

Examples of the "DNA intercalator" include, but are not limited to, proflavine, doxorubicin (adriamycin), daunorubicin, dactinomycin, thalidomide, and DDS formulations thereof.

Examples of the "antimitotic agent" include, but are not limited to, paclitaxel, paclitaxel derivatives (e.g., DHA paclipaclitaxe, paclitaxel polyglutamate, nab-paclitaxel, micellar paclitaxel, 7α-glucosyloxyacetylpaclitaxel, and BMS-275183), docetaxel, vinorelbine, vincristine, vinblastine, vindesine, vinzolidine, etoposide, teniposide, ixabepilone, larotaxel, ortataxel, tesetaxel, ispinesib, colchicine, vinflunine, and DDS formulations thereof.

Examples of the "antitumor antibiotic" include, but are not limited to, actinomycin D, actinomycin C, mitomycin C, chromomycin A3, mithramycin A, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, amrubicin hydrochloride, neocarzinostatin, zinostatin stimalamer, mithramycin, sarkomycin, carzinophilin, mitotane, zorubicin hydrochloride, mitoxantrone hydrochloride, idarubicin hydrochloride, liposomal doxorubicin, and DDS formulations thereof.

Examples of the "plant-derived anticancer agent" include, but are not limited to, irinotecan, nogitecan, etoposide, etoposide phosphate, eribulin, sobuzoxane, vinblastine sulfate, vincristine sulfate, vindesine sulfate, teniposide, paclitaxel, paclitaxel injection, docetaxel, DJ-927, vinorelbine, topotecan, and DDS formulations thereof.

Examples of the "epigenome drug" include, but are not limited to, DNA methylation inhibitors, histone deacetylase (HDAC) inhibitors, DNA methyl transferase (DNMT) inhibitors, histone deacetylase activators, histone demethylase inhibitors, and methylated nucleotides.

Specific examples of the "epigenome drug" include, but are not limited to, vorinostat, belinostat, mocetinostat (MGCDO103), entinostat (SNDX-275), romidepsin, azacytidine, decitabine, GSK2879552 2HI, SGC707, ORY-1001 (RG-6016), PFI-4, SirReal2, GSK2801, CPI-360, GSK503, AMI-1, CPI-169, and DDS formulations thereof.

Examples of the "immunomodulator" include, but are not limited to, thalidomide, lenalidomide, pomalidomide, and DDS formulations thereof.

The "molecular targeted drug" can be a small compound or an antibody. Examples of the "molecular targeted drug" include, but are not limited to, kinase inhibitors, proteasome inhibitors, monoclonal antibodies, mTOR inhibitors, TNF inhibitors, and T-cell inhibitors.

Examples of the "kinase inhibitor" include, but are not limited to, tyrosine kinase inhibitors, serine/threonine kinase inhibitors, Raf kinase inhibitors, cyclin-dependent kinase (CDK) inhibitors, and mitogen-activated protein kinase (MEK) inhibitors.

Specific examples of the "kinase inhibitor" include, but are not limited to, imatinib, gefitinib, erlotinib, afatinib, dasatinib, bosutinib, vandetanib, sunitinib, axitinib, pazopanib, lenvatinib, lapatinib, nintedanib, nilotinib, crizotinib, ceritinib, alectinib, ruxolitinib, tofacitinib, ibrutinib, sorafenib, vemurafenib, dabrafenib, palbociclib, trametinib, regorafenib, cedivanib, lestaurtinib, bandetinib, vatalanib, seliciclib, tivantinib, canertinib, pelitinib, tesevatinib, cediranib, motesanib, midostaurin, foretinib, cabozantinib, selumetinib, neratinib, volasertib, saracatinib, enzastaurin, tandutinib, semaxanib, alvocidib, ICR-62, AEE788, PD0325901, PD153035, TK787, amcasertib (BBI503), E6201, E7050, and DDS formulations thereof.

Examples of the "proteasome inhibitor" include, but are not limited to, bortezomib, carfilzomib, and DDS formulations thereof.

Examples of the "monoclonal antibody" include, but are not limited to, anti-CD22 antibodies, anti-CD20 antibodies, anti-CD25 antibodies, anti-CD30 antibodies, anti-CD33 antibodies, anti-CD5 antibodies, anti-CD52 antibodies, antiepidermal growth factor receptor antibodies (EGFR antibodies), anti-vascular endothelial cell growth factor antibodies (VEGF antibodies), anti-TNF-α antibodies, anti-IL-1 receptor antibodies, anti-IL-2 receptor antibodies, anti-IL-5 receptor antibodies, anti-IL-6 receptor antibodies, anti-HER2 antibodies, anti-IgE antibodies, anti-IgG antibodies, anti-RS virus antibodies, anti-CCR4 antibodies, anti-cytotoxic T lymphocyte-associated antigen 4 (CTLA-4, CD152) antibodies, anti-PD-1 antibodies, anti-receptor activator of nuclear factor KB ligand (RANKL) antibodies, anti-c-Met antibodies, and anti-CXCR4 antibodies.

Specific examples of the "monoclonal antibody" include, but are not limited to, ibritumomab tiuxetan, rituximab, cetuximab, infliximab, basiliximab, brentuximab vedotin, tocilizumab, trastuzumab, bevacizumab, omalizumab, mepolizumab, qemtuzumab, ozogamicin, palivizumab, ranibizumab, certolizumab, ocrelizumab, mogamulizumab, eculizumab, pertuzumab, alemtuzumab, inotuzumab, panitumumab, ofatumumab, golimumab, adalimumab, ramucirumab, nivolumab, anakinra, denosumab, ipilimumab, pembrolizumab, matuzumab, farletuzumab, MORAb-004, MORA-b009, and DDS formulations thereof.

Examples of the "mTOR inhibitor" include, but are not limited to, everolimus (RAD001), rapamycin (sirolimus), AZD8055, temsirolimus (CCI-779, NSC683864), KU-0063794, voxtalisib (XL-765, SAR245409), MHY1485, dactolisib (BEZ235), PI-103, torkinib (PP242), ridaforolimus (deforolimus, MK-8669), INK-128 (MLN0128), Torin1, omipalisib (GSK2126458, GSK458), OSI-027, PF-04691502, apitolisib (GDC-0980, RG7422), GSK1059615, gedatolisib (PF-05212384, PKI-587), WYE-132, PP121, WYE-354, AZD2014, Torin2, WYE-687, CH5132799, WAY-600, ETP-46464, GDC-0349, XL388, zotarolimus (ABT-578), tacrolimus (FK506), BGT226 (NVP-BGT226), Palomid 529 (P529), chrysophanic acid, and DDS formulations thereof.

Examples of the "TNF inhibitor" include, but are not limited to, etanercept, lenalidomide (CC-5013), pomalidomide, thalidomide, necrostatin-1, and QNZ (EVP4593).

Examples of the "T-cell inhibitor" include, but are not limited to, abatacept.

Examples of the "angiogenesis inhibitor" include, but are not limited to, CM101, IFN-α, IL-12, platelet factor-4, suramin, semaxanib, thrombospondin, VEGFR antagonists, combinations of an angiostatic steroid and heparin, cartilage-derived angiogenesis inhibitors, matrix metalloproteinase inhibitors, batimastat, marimastat, angiostatin, endostatin, 2-methoxyestradiol, tecogalan, thrombospondin, axV3 inhibitors, linomide, ADH-1, E7820, and DDS formulations thereof.

Examples of the "other chemotherapeutic agent" include, but are not limited to, finasteride, sobuzoxane, obatoclax, efaproxiral, tipifarnib, and lonafarnib.

The peptide or the compound of formula (1), or a pharmaceutically acceptable salt thereof, or a combination thereof as described herein may be administered in combination with a non-drug therapy, or even more than one non-drug therapy selected, for example, from surgery, radiotherapy, gene therapy, hyperthermia, cryotherapy, or laser burning therapy. For example, the peptide or the compound of formula (I), or a pharmaceutically acceptable salt thereof, or a combination thereof as described herein may be administered before or after a non-drug therapy such as surgery, or before or after a combination of two or three non-drug therapies.

The pharmaceutical composition of the present invention may comprise the peptide or the compound of formula (1), or a pharmaceutically acceptable salt thereof, or a combination thereof as described herein as an active ingredient together with a pharmaceutically acceptable carrier. Also, the pharmaceutical composition of the invention may further comprise, or be administered in combination with, an appropriate adjuvant for enhancing the induction of WT1-specific CTLs and/or helper T cells by the composition.

The "pharmaceutically acceptable carrier" refers to a carrier which is non-toxic to a cell or a mammal exposed to the carrier at an amount or concentration it is used. In some embodiments, a pH buffered aqueous solution is used as a pharmaceutically acceptable carrier. Examples of the "pharmaceutically acceptable carrier" include buffering agents (such as phosphate, citrate, lactate, tartrate, trifluoroacetate and other organic acids); antioxidants (such as ascorbic acid); low molecular weight polypeptides (less than about 10 residues); proteins (such as serum albumin, gelatin or immunoglobulin); hydrophilic polymers (such as polyvinylpyrrolidone); amino acids (such as glycine, glutamine, asparagine, arginine, methionine or lysine); monosaccharides, disaccharides and other carbohydrates (such as glucose, mannose or dextrin); chelating agents (such as EDTA); sugar alcohols (such as mannitol, trehalose or sorbitol); stabilizers (such as diethylenetriaminepentaacetic acid); salt forming counterions (such as sodium); solubilizing agents (such as polysorbate 80®), and/or nonionic surfactants (such as TWEEN®, polyethylene glycol (PEG) and PLURONICS®). A macromolecular material which is metabolized slowly, such as a protein, a polypeptide, a liposome, a polysaccharide, polylactide, polyglycolic acid, polymeric amino acids, amino acid copolymers, and inactive virus particles may also be useful as a pharmaceutically acceptable carrier for the present invention. For administration of a WT1 antigen peptide as described herein, the peptide may be formulated in a liposome preparation, attached to beads having a diameter of a micrometer order, or associated with a lipid carrier.

Any adjuvant as described in Clin. Microbiol. Rev., 7: 277-289, 1994 may be useful as an adjuvant for the present invention. Specifically, an adjuvant useful for the present invention may be a microorganism-derived agent, GM-CSF, a cytokine such as interleukin-2, interleukin-7, or interleukin-12, a plant-derived agent, a marine organism-derived agent, a mineral gel such as aluminum hydroxide, lysolecithin, a surfactant such as pluronic polyol, a polyanion, a peptide, or an oil emulsion (an emulsion preparation). Examples of the microorganism-derived agent include lipid A, monophosphoryl lipid A, which is a derivative of lipid A, killed bacteria (e.g., *Mycobacterium* bacteria such as BCG bacteria), bacterium-derived proteins, polynucleotides, Freund's incomplete adjuvant, Freund's complete adjuvant, cell wall skeleton components (e.g., BCG-CWS), trehalose dimycolate (TDM).

An adjuvant for the present invention may be a sedimentary adjuvant or an oil adjuvant. A sedimentary adjuvant can be a suspension of an inorganic substance to which a peptide can be adsorbed. Examples of the sedimentary adjuvant include sodium hydroxide, aluminum hydroxide (Alum), calcium phosphate, aluminum phosphate, alum, Pepesu, and carboxyvinyl polymer. An oil adjuvant can be an oil emulsifier which is able to emulsify a peptide by forming micelles comprising an aqueous peptide solution phase encapsulated in a mineral oil membrane. Examples of the oil adjuvant include, but are not limited to, liquid paraffin, lanolin, Freund's adjuvant (Freund's complete adjuvant, and Freund's incomplete adjuvant), Montanide, and a W/O emulsion (see WO2006/078059).

The pharmaceutical composition of the present invention may comprise a sugar alcohol such as mannitol, trehalose, or lactose; a pH adjusting agent conventionally used for pharmaceutical preparations, for example selected from the group consisting of hydrochloric acid, sulfuric acid, nitric acid, acetic acid, citric acid, tartaric acid, lactic acid, maleic acid, phosphoric acid, sodium hydroxide, potassium hydroxide, aqueous ammonia, sodium acetate hydrate, anhydrous sodium acetate, sodium citrate hydrate, sodium dihydrogen citrate, sodium tartrate, disodium phosphate, dipotassium phosphate, sodium dihydrogen phosphate, potassium dihydrogen phosphate, and trisodium phosphate; a filler; a buffer; a suspending agent; a wetting agent; a solubilizer; a dispersant; a preservative; and/or a coloring agent; or any other excipient.

The pharmaceutical composition of the present invention may be provided as a solid or liquid dosage form for oral administration, or a dosage form for parenteral administration, for example an injectable preparation, a suppository, an inhalable preparation, or a nasal preparation. Examples of the solid dosage form for oral administration include a tablet, a pill, a capsule (including a hard capsule and a soft capsule), a powder, and a granule. The pharmaceutical composition may also be formulated into such a tablet form as a sublingual tablet, a buccal tablet, or a rapidly disintegrating oral tablet. In a preferred embodiment, the pharmaceutical composition is provided as an injectable preparation.

The pharmaceutical composition in a solid oral dosage form may be prepared in accordance with a conventionally known preparation method, and may comprise one or more active agents either alone or in admixture with a filler (such as lactose, mannitol, glucose, microcrystalline cellulose, or starch), a binder (such as hydroxypropyl cellulose, polyvinylpyrrolidone, or magnesium aluminometasilicate), a disintegrating agent (such as calcium cellulose glycolate), a lubricant (such as magnesium stearate), a stabilizer, a solubilizing aid (such as glutamic acid, or aspartic acid), or other appropriate excipient. A solid oral dosage form may optionally be coated with sucrose, gelatin, hydroxypropyl cellulose, hydroxypropylmethyl cellulose phthalate, or other appropriate coating agent. Two or more layers of coating may be applied on the dosage form. A solid oral dosage form may be prepared in a capsule which may be formed of a bioabsorbable material such as gelatin. A solid oral dosage form may additionally comprise a preservative, an antioxidant, a coloring agent, a sweetener, or other appropriate additive.

The pharmaceutical composition in the form of a sublingual tablet may be prepared in accordance with a conventionally known preparation method, an may comprise one or more active agents in admixture with a filler (such as lactose, mannitol, glucose, microcrystalline cellulose, colloidal silica, or starch), a binder (such as hydroxypropyl cellulose, polyvinylpyrrolidone, or magnesium aluminometasilicate), a disintegrating agent (such as starch, L-hydroxypropyl cellulose, carboxymethyl cellulose, croscarmellose sodium, or calcium cellulose glycolate), a lubricant (such as magnesium stearate), a swelling agent (such as hydroxypropyl cellulose, hydroxypropylmethyl cellulose, carbopol, carboxymethyl cellulose, polyvinyl alcohol, xanthan gum, or guar gum), a swelling aid (such as glucose, fructose, mannitol, xylitol, erythritol, maltose, trehalose, phosphate, citrate, silicate, glycine, glutamic acid, or arginine), a stabilizer, a solubilizing aid (such as polyethylene glycol, propylene glycol, glutamic acid, or aspartic acid), a flavoring agent (such as an orange, strawberry, mint, lemon, or vanilla flavor), or other appropriate excipient. A sublingual tablet may optionally be coated with sucrose, gelatin, hydroxypropyl cellulose, hydroxypropylmethyl cellulose phthalate, or other appropriate coating agent. Two or more layers of coating may be applied on a tablet. A sublingual tablet may additionally comprise a preservative, an antioxidant, a coloring agent, a sweetener, or other appropriate additive.

The pharmaceutical composition in the form of a buccal tablet may be prepared in accordance with a conventionally known preparation method, and may comprise one or more active agents in admixture with a filler (such as lactose, mannitol, glucose, microcrystalline cellulose, colloidal silica, or starch), a binder (such as hydroxypropyl cellulose, polyvinylpyrrolidone, or magnesium aluminometasilicate), a disintegrating agent (such as starch, L-hydroxypropyl cellulose, carboxymethyl cellulose, croscarmellose sodium, or calcium cellulose glycolate), a lubricant (such as magnesium stearate), an adhesive agent (such as hydroxypropyl cellulose, hydroxypropylmethyl cellulose, carbopol, carboxymethyl cellulose, polyvinyl alcohol, xanthan gum, or guar gum), an adhesive aid (such as glucose, fructose, mannitol, xylitol, erythritol, maltose, trehalose, phosphate, citrate, silicate, glycine, glutamic acid, or arginine), a stabilizer, a solubilizing aid (such as polyethylene glycol, propylene glycol, glutamic acid, or aspartic acid), a flavoring agent (such as an orange, strawberry, mint, lemon, or vanilla flavor), or other appropriate excipient. A buccal tablet may optionally be coated with sucrose, gelatin, hydroxypropyl cellulose, hydroxypropylmethyl cellulose phthalate, or other appropriate coating agent. Two or more layers of coating may be applied on a tablet. A buccal tablet may additionally comprise a preservative, an antioxidant, a coloring agent, a sweetener, or other appropriate additive.

The pharmaceutical composition in the form of a rapidly disintegrating oral tablet may be prepared in accordance with a conventionally known preparation method, which may comprise steps of providing one or more active agents in a powder or granule form, and optionally coating them with a coating agent (such as ethyl cellulose, hydroxypropyl cellulose, hydroxypropylmethyl cellulose, or an acrylic acid/methacrylic acid copolymer) or a plasticizer (such as polyethylene glycol, or triethyl citrate), and admixing them with a filler (such as lactose, mannitol, glucose, microcrystalline cellulose, colloidal silica, or starch), a binder (such as hydroxypropyl cellulose, polyvinylpyrrolidone, or magnesium aluminometasilicate), a disintegrating agent (such as starch, L-hydroxypropyl cellulose, carboxymethyl cellulose, croscarmellose sodium, or calcium cellulose glycolate), a lubricant (such as magnesium stearate), a disintegrating aid (such as glucose, fructose, mannitol, xylitol, erythritol, maltose, trehalose, phosphate, citrate, silicate, glycine, glutamic acid, or arginine), a stabilizer, a solubilizing aid (such as polyethylene glycol, propylene glycol, glutamic acid, or aspartic acid), a flavoring agent (such as an orange, strawberry, mint, lemon, or vanilla flavor), or other appropriate excipient. A rapidly disintegrating oral tablet may optionally be coated with sucrose, gelatin, hydroxypropyl cellulose, hydroxypropylmethyl cellulose phthalate, or other appropriate coating agent. Two or more layers of coating may be applied on a tablet. A rapidly disintegrating oral tablet may additionally comprise a preservative, an antioxidant, a coloring agent, a sweetener, or other appropriate additive.

The pharmaceutical composition in a liquid dosage form for oral administration may be in the form of a solution, a suspension, an emulsion, a syrup, or an elixir, in which one or more active agents are dissolved, dispersed or emulsified in a conventionally used pharmaceutically acceptable vehicle (such as purified water, ethanol, or a mixture thereof). A liquid oral dosage form may optionally comprise a wetting agent, a dispersant, an emulsifier, a sweetener, a flavoring agent, a preservative, a buffer, or other appropriate additive.

The pharmaceutical composition in a dosage form for topical application may be in the form of an ointment, a gel, a cream, a plaster, a patch, a liniment, a spray, an inhalant, an aerosol, an eye drop, or a nasal drop, which may be prepared in accordance with a conventionally known preparation method, and may comprise one or more active agents.

An ointment may be prepared in accordance with a conventionally known preparation method, for example by incorporating one or more active agents in an ointment base by grinding or melting. For preparing an ointment, any conventionally used ointment base may be used, which may comprise a higher fatty acid or fatty acid ester (such as adipic acid, myristic acid, palmitic acid, stearic acid, or oleic acid, or an ester thereof), a wax (such as beeswax, spermaceti, or ceresin), a surfactant (such as polyoxyethylene alkyl ether phosphate), a higher alcohol (such as cetanol, stearyl alcohol, or cetostearyl alcohol), a silicone oil (such as dimethylpolysiloxane), a hydrocarbon (such as a hydrophilic petrolatum, white petrolatum, purified lanolin, or liquid paraffin), a glycol (such as ethylene glycol, diethylene glycol, propylene glycol, polyethylene glycol, or macrogol), a vegetable oil (such as castor oil, olive oil, sesame oil, or turpentine oil), an animal oil (such as mink oil, egg-yolk oil, squalane, or squalene), water, an absorption enhancer, a skin protective agent, or a combination thereof. An ointment may additionally comprise a humectant, a preservative, a stabilizer, an antioxidant, a fragrance, or other appropriate additive.

The pharmaceutical composition in a gel form may be prepared in accordance with a conventionally known preparation method, for example by incorporating one or more active agents in a gel base by melting. For preparing a gel, any conventionally used pharmaceutical gel base may be used, which may comprise a lower alcohol (such as ethanol, or isopropyl alcohol), a gelling agent (such as carboxymethyl cellulose, hydroxyethyl cellulose, hydroxypropyl cellulose, or ethyl cellulose), a neutralizing agent (such as triethanolamine, or diisopropanolamine), a surfactant (such as polyoxyethylene glycol monostearate), a gum, water, an absorption enhancer, a skin protective agent, or a combination thereof. A gel may additionally comprise a preservative, an antioxidant, a fragrance, or any other appropriate additive (s). The pharmaceutical composition in a cream form may be prepared in accordance with a conventionally known preparation method, for example by incorporating one or more active agents in a pharmaceutical cream base by melting or emulsification. For preparing a cream, any conventionally used pharmaceutical cream base may be used, which may comprise a higher fatty acid ester, a lower alcohol, a hydrocarbon, a polyhydric alcohol (such as propylene glycol, or 1,3-butylene glycol), a higher alcohol (such as 2-hexyldecanol, or cetanol), an emulsifier (such as a polyoxyethylene alkyl ether, or a fatty acid ester), water, an absorption enhancer, a skin protective agent, or a combination thereof. A cream may additionally comprise a preservative, an antioxidant, a fragrance, or other appropriate additive.

The pharmaceutical composition in the form of a plaster may be prepared in accordance with a conventionally known preparation method, for example by incorporating one or more active agents in a plaster base by melting, and applying the mixture onto a support. For preparing a plaster, any conventionally used pharmaceutical plaster base may be used, which may comprise a thickening agent (such as polyacrylic acid, polyvinylpyrrolidone, gum arabic, starch, gelatin, or methyl cellulose), a humectant (such as urea, glycerol, or propylene glycol), a filler (such as kaolin, zinc oxide, talc, calcium, or magnesium), water, a solubilizing aid, a tackifier, a skin protective agent, or a combination thereof. A plaster may additionally comprise a preservative, an antioxidant, a fragrance, or other appropriate additive.

The pharmaceutical composition in the form of a patch may be prepared in accordance with a conventionally known preparation method, for example by incorporating one or more active agents in a patch base by melting, and applying the mixture onto a support. For preparing a patch, any conventionally used pharmaceutical patch base may be used, which may comprise a polymer, an oil or fat, a higher fatty acid, a tackifier, a skin protective agent, or a combination thereof. A patch may additionally comprise a preservative, an antioxidant, a fragrance, or other appropriate additive.

The pharmaceutical composition in the form of a liniment may be prepared in accordance with a conventionally known preparation method, for example by dissolving, dispersing or emulsifying one or more active agents in a vehicle which may comprise water, an alcohol (such as ethanol, or polyethylene glycol), a higher fatty acid, glycerol, soap, an emulsifier, a dispersant, or a combination thereof. A liniment may additionally comprise a preservative, an antioxidant, a fragrance, or other appropriate additive.

The pharmaceutical composition in the form of a spray, or an inhalant may comprise active agent(s), and optionally a stabilizing agent such as sodium hydrogen sulfite, or a tonicity agent or buffer, such as sodium chloride, sodium citrate or citric acid, in a vehicle.

The pharmaceutical composition in a dosage form for injection may be in the form of a solution, a suspension, or an emulsion, which comprises one or more active agents dissolved, dispersed or emulsified in a liquid for injection, or may be provided as a solid formulation comprising active agent(s) to be dissolved or dispersed in a liquid for injection before use. A liquid for injection may comprise distilled water for injection, physiological saline, a vegetable oil, propylene glycol, polyethylene glycol, an alcohol such as ethanol, or a combination thereof. An injectable preparation may additionally comprise a stabilizer, a solubilizing aid (such as glutamic acid, aspartic acid, or polysorbate 80®), a dispersant, an emulsifier, an analgesic, a buffer, a preservative, or other appropriate additive. For providing an injectable preparation as a sterilized preparation, it may be subjected to sterilization in the final step of its production, or produced aseptically throughout its production. A formulation for injection may be provided as a sterilized solid formulation, for example a lyophilized formulation, which may be reconstituted in sterilized water for injection or other appropriate sterilized liquid before use.

The pharmaceutical composition in a dosage form for inhalation may be in the form of an aerosol, an inhalable powder, or an inhalable liquid, or may be provided as a liquid concentrate which is to be dissolved or dispersed in water or other appropriate vehicle to form an inhalable preparation before use. A preparation for inhalation may be prepared in accordance with a conventionally known preparation method. An inhalable liquid may optionally comprise a preservative (such as benzalkonium chloride, or paraben), a coloring agent, a buffer (such as sodium phosphate, or sodium acetate), a tonicity agent (such as sodium chloride, or concentrated glycerin), a thickening agent (such as a carboxyvinyl polymer), an absorption enhancer, or other appropriate additive.

An inhalable powder may optionally comprise a lubricant (such as stearic acid, or a salt thereof), a binder (such as starch, or dextrin), a filler (such as lactose, or cellulose), a coloring agent, a preservative (such as benzalkonium chloride, or paraben), an absorption enhancer, or other appropriate additive.

For administration of an inhalable liquid, a spray device (such as an atomizer, or a nebulizer) is usually used. An inhalable powder is usually dispensed from a powder inhalation device.

The pharmaceutical composition in the form of a spray may comprise active agent(s), and optionally a stabilizing agent (such as sodium hydrogen sulfite), or a tonicity agent or buffer (such as sodium chloride, sodium citrate, or citric acid) in a vehicle. A spray may be prepared in accordance with a preparation method as described, for example, in U.S. Pat. No. 2,868,691, or U.S. Pat. No. 3,095,355.

The pharmaceutical composition of the present invention may be prepared in other parenteral dosage form. For example, one or more active agents may be formulated into a rectal suppository or a vaginal pessary by a conventionally known preparation method.

In one embodiment, the composition of the present invention comprising the peptide or the compound of formula (1), or a pharmaceutically acceptable salt thereof, or a combination thereof as described herein comprises one or more pharmaceutically acceptable carriers selected from the group consisting of trehalose, mannitol, methionine, citric acid, lactic acid, tartaric acid, acetic acid, trifluoroacetic acid, and a pH adjusting agent.

The peptide or the compound of formula (1), or a pharmaceutically acceptable salt thereof, or a combination thereof as described herein can be administered to a subject by an appropriate method depending on a disease of the subject to treat, a condition of the subject, a target site of the administration, or other factor. For example, administration by intravenous, intramuscular, intradermal, intraperitoneal, subcutaneous or intraspinal injection or infusion, or other parenteral administration may be useful. The term "parenteral administration" as used herein refers to a usual mode of administration by injection or infusion other than enteral or topical administration, and includes, but is not limited to, intravenous, intramuscular, intraarterial, intrathecal, intracapsular, intraorbital, intracardiac, intradermal, intraperitoneal, intratracheal, subcutaneous, subepidermal, intraarticular, subcapsular, subarachnoidal, intraspinal, epidural or infrasternal injection or infusion. The peptide or compound of the present invention may be administered in a lymphocyte therapy or a DC (dendritic cell) therapy. When an immunomodulator is coadministered, it may be administered transdermally, or transmucosally by intranasal, buccal, vaginal, rectal, or sublingual administration.

Frequency of dose, or dosing interval may be appropriately selected depending on a disease to treat by the drug, a condition of a recipient of the drug, a route of administration of the drug, or other factor. Administration is usually repeated, preferably every few days or few months.

The peptide or the compound of formula (1), or a pharmaceutically acceptable salt thereof, or a coadministration drug, if any, as described herein can be administered to a subject in an appropriate amount depending on a disease of the subject to treat, a condition of the subject, a particular route of the administration, or other factor. The peptide or the compound, or a pharmaceutically acceptable salt thereof may usually be administered in an amount of 0.0001 mg to 1000 mg, preferably 0.001 mg to 1000 mg, more preferably 0.1 mg to 10 mg, at one time. A coadministration drug may be administered in an amount appropriately selected on the basis of a known clinical dose of the drug. For example, an immunomodulator as a coadministration drug may usually be administered in an amount of 0.0001 mg to 1000 mg per kg body weight, preferably 0.001 mg to 1000 mg per kg body weight, more preferably 0.1 mg to 10 mg per kg body weight.

When more than one active agent is incorporated in a single composition, they may be incorporated at an amount ratio appropriately selected depending on a disease to treat, a condition of a recipient of the composition, a route of administration of the composition, or other factor. For example, for treating a human subject by administration of a composition comprising a peptide of the present invention and/or a compound of the present invention and an immunomodulator or other coadministration drug, the immunomodulator or coadministration drug may be used in an amount of 0.01 to 100 parts by weight relative to the peptide and/or the compound of the present invention.

The term "subject" as used herein includes human and non-human mammals. Non-human mammals include, but are not limited to, non-human primate, ovine, canine, feline, equine, and bovine. A human subject, especially a human subject in need of potentiation of immune response is preferred.

The term "effective amount" as used herein means an amount of an active agent that completely or partially inhibits the progression of a cancer, or at least partially reduces one or more symptoms of a cancer. An effective amount may be a therapeutically or prophylactically effective amount. An effective amount an agent is determined depending on the age or sex of a recipient of the agent, the type or severity of a condition to treat with the agent, a desired outcome of the treatment with the agent, or other factor. A person skilled in the art can determine an effective amount for a particular patient.

The present invention is useful for treating or preventing (including prevention of recurrence) a "cancer accompanied by WT1 gene expression" or a "cancer accompanied by an elevated level of WT1 gene expression". Examples of such a cancer include a hematologic cancer such as leukemia, myelodysplastic syndrome, multiple myeloma, and malignant lymphoma, and a solid tumor such as gastric cancer, colorectal cancer, lung cancer, breast cancer, germ cell cancer, liver cancer, skin cancer, urinary bladder cancer, prostate cancer, uterine cancer, cervical cancer, ovarian cancer, glioblastoma multiforme, malignant melanoma, non-small cell lung cancer, renal cell carcinoma or brain tumor.

Further examples of cancers which can be treated or prevented by the present invention include bone cancer, pancreatic cancer, cancer of the head or neck, cutaneous or intraocular malignant melanoma, rectal cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia such as acute myeloid leukemia, chronic myeloid leukemia, acute lymphoblastic leukemia, or chronic lymphocytic leukemia, childhood solid tumor, lymphocytic lymphoma, cancer of the kidney or ureter, carcinoma of the renal pelvis, central nervous system (CNS) tumor, primary CNS lymphoma, tumor angiogenesis, spinal tumor, brainstem glioma, pituitary adenoma, Kaposi's sarcoma, epidermoid cancer, squamous cell cancer, T-cell lymphoma, environmentally induced cancers including asbestos-induced cancer, and combinations of the cancers as described above.

An unwanted side effect, if any, of a peptide or a compound of formula (I), or a pharmaceutically acceptable salt thereof, or a combination thereof as described herein can be counteracted by coadministration of an agent appropriate for the purpose, such as an antiemetic agent, sleep-inducing agent, or anticonvulsant.

The peptide or the compound of formula (1), or a pharmaceutically acceptable salt thereof, or a combination thereof as described herein may be used in combination with other cancer antigen peptide. For example, the administration of a WT1 helper peptide of the present invention may be preceded by, or followed by the administration of another cancer antigen peptide, for example a WT1 killer peptide, $WT1_{126}$ peptide. Such a combination is therapeutically beneficial, because the therapeutic effect of a WT1 killer peptide through the induction of CTL activity can be enhanced by a WT1 helper peptide which is able to induce WT1-specific helper T cells and activate B cells and other T cells.

Examples of such other cancer antigen peptide include peptides, or derivatives or conjugates thereof as described in the following publications: WO 2000/006602, WO 2002/079253, WO 2003/106682, WO 2004/026897, WO 2004/063903, WO 2007/063903, WO 2010/123065, WO 2014/157692, WO 2005/053618, WO 2007/047764, WO 2007/120673, WO 2005/045027, WO 2010037395, WO 2000/018795, WO 2002/028414, WO 2003/037060, and WO 2004/100870.

In another aspect, the present invention provides an antigen presenting cell (for example, a dendritic cell, B-lymphocyte, macrophage) which presents a WT1 helper peptide as described herein via an MHC class II molecule. By using the antigen presenting cell, a WT1-specific helper T cell is induced efficiently.

In another aspect, the present invention provides a method of inducing antigen presenting cells, wherein the method comprises culturing immature antigen presenting cells in the presence of the WT1 helper peptide as described herein, and inducing antigen presenting cells that present the peptide on the cells via an MHC class II molecule from the immature antigen presenting cells. As used herein, the term "immature antigen presenting cells" refers to cells which can mature into antigen presenting cells such as dendritic cells, B-lymphocytes or macrophages. The immature antigen presenting cells are found, for example, in a peripheral mononuclear cell population. Therefore, such a cell population may be cultured in the presence of a WT1 helper peptide in the method of inducing antigen presenting cells.

In another aspect, the present invention provides a method of preventing or treating a cancer in a subject, wherein the method comprises administering antigen presenting cells that present a WT1 helper peptide as described herein on the cells via an MHC class II molecule to a subject, wherein the subject has the same MHC class II molecule. The antigen presenting cells may be administered by any method appropriately selected depending on a disease to treat, a condition of the subject, or a target site of the administration, or other factor. The antigen presenting cells may be administered intravenously, intradermally, subcutaneously, intramuscularly, intranasally, or orally, or by other administration route.

In another aspect, the present invention provides a WT1-specific helper T cell which can be induced by a WT1 helper peptide as described herein. Once a complex of a WT1 helper peptide with an MHC class II molecule is recognized by a precursor cell, a WT1-specific helper T cell is induced, grown and activated. The activated WT1-specific helper T cell produces cytokines such as IL-2, IL-4, IL-5, IL-6 or interferon (IFN), and stimulates B cells or other T cell subsets to grow, differentiate, or mature. Therefore, the helper T cell of the present invention is useful for inducing cytotoxicity in WT1-expressing tumor cells.

In another aspect, the present invention provides a method of inducing WT1-specific helper T cells, wherein the method comprises culturing peripheral blood mononuclear cells in the presence of a WT1 helper peptide as described herein, so that WT1-specific helper T cells are induced from the peripheral blood mononuclear cells. In particular, when peripheral blood mononuclear cells are cultured in the presence of a WT1 helper peptide, WT1-specific helper T cells are induced from precursor helper T cells in the peripheral blood mononuclear cell population. The WT1-specific helper T cells obtained by the method can be administered to a subject to treat or prevent a cancer in the subject.

In another aspect, the present invention provides a method of preventing or treating a cancer, wherein the method comprises administering WT1-specific helper T cells to a subject. The WT1-Specific helper T cells can be administered by a method appropriately selected depending on a disease to treat, a condition of the subject, or a target site of the administration, or other factor. The WT1-Specific helper T cells may be administered intravenously, intradermally, subcutaneously, intramuscularly, intranasally, or orally, or by other administration route.

In another aspect, the present invention provides a kit for inducing WT1-specific helper T cells, wherein the kit comprises a WT1 helper peptide as described herein as a component. In an embodiment, the kit is for use in the method for inducing WT1-specific helper T cells as described above. Besides a WT1 helper peptide, the kit may comprise, for example, a means for harvesting peripheral blood mononuclear cells, an adjuvant, or a container for reaction, and usually instructions for use.

In another aspect, the present invention provides a kit for preventing or treating a cancer, wherein the kit comprises a peptide, a polynucleotide or an expression vector as described herein as a component. In an embodiment, the kit is for use in inducing antigen presenting cells that present a WT1 helper peptide on the cells via an MHC class II molecule. Besides the essential component, the kit may comprise, for example, a means for obtaining a sample, or a container for reaction, and usually instructions for use.

In another aspect, the present invention provides a method of determining the presence or amount of WT1-specific helper T cells in a subject, wherein the method comprises the steps of:
(a) contacting a sample from a subject with a WT1 helper peptide; and
(b) determining the presence or amount of a cytokine in the sample. Any sample from a subject can be used in the method, provided that it potentially contains lymphocytes. For example, a peripheral blood mononuclear cell sample, a blood sample, a body fluid sample, or a tissue sample may be used. A peripheral blood mononuclear cell sample is preferred. In step (a) of the method, a sample from a subject can be cultured in the presence of a WT1 helper peptide for reaction with the peptide. A person skilled in the art can determine appropriate culture conditions for the step. The presence or amount of a cytokine in the sample can be determined by a method known in the art. A cytokine in the sample can be interferon α, interleukin 10, or other cytokine helper T cells can produce. A cytokine in the sample can be labeled with a fluorescent label, a radio label, or other appropriate label known in the art. The method of the present invention is useful in detection of a cancer, especially a cancer accompanied by WT1 gene expression or an elevated level of WT1 gene expression, or in monitoring immune response to such a cancer or response to a therapy for such a cancer.

The compound of formula (1) has favorable physicochemical properties and high stability, and can be prepared easily and conveniently to comprise in a molecule different cancer antigen peptides which can be selected from a wide variety of cancer antigen peptides. For example, the compound may comprise in a molecule a peptide capable of binding to cells of A02 type (for example, A-0201, or A0206) and a peptide capable of binding to cells of A24 type (for example, A-2402). The compound of the present invention can be used in combination with a WT1 helper peptide according to the present invention. Thus, the present invention provides an improved method for treatment or prevention of a cancer.

EXAMPLES

The present invention is described in further detail in the following Examples which are not in any way intended to limit the scope of the invention.

Example 1

Synthesis of a peptide consisting of the amino acid sequence:

```
                                        (SEQ ID NO: 5)
PGCNKRYFKLSHLQMHSRK (Pro-Gly-Cys-Asn-Lys-Arg-Tyr-

Phe-Lys-Leu-Ser-His-Leu-Gln-Met-His-Ser-Arg-Lys)
```

The peptide was synthesized by an Fmoc/tBu method for solid-phase peptide synthesis. Specifically, peptide chain elongation was performed by using as a starting material 1.00 g of Fmoc-Lys(Boc)-Alko-PEG resin (wherein Fmoc represents 9-fluorenylmethyloxycarbonyl, Boc represents tert-butoxycarbonyl, Alko represents p-alkoxybenzyl alcohol, and PEG represents polyethylene glycol) (Watanabe Chemical Industries; 0.23 mmol/g, 0.23 mmol) in CS Bio CS336X peptide synthesizer. For removing the Fmoc protecting group, the resin was treated with a solution of 20% piperidine in N,N-dimethylformamide (DMF) for 5 minutes or 20 minutes. For coupling a protected amino acid to the resin, a solution of 1.05 mmol of a protected amino acid, 1 mmol of O-(benzotriazol-1-yl)-N,N,N',N'-tetramethyluronium hexafluorophosphate (HBTU), 2 mmol of N,N-diisopropylethylamine (DIPEA) in DMF was added to the resin and reacted for one hour. The resin from the reaction was washed with DMF and diethyl ether, and dried under vacuum. The resin to which a synthesized peptide chain was attached was incubated for two hours in 10 ml of a mixture of trifluoroacetic acid (TFA)/water/triisopropylsilane (TIS)/ethane dithiol (EDT) (volume ratio: 94/2.5/2.5/1) at room temperature. The resin was then filtered off. The filtrate was concentrated under vacuum, and then cooled on ice and diluted in 50 ml of diethyl ether to precipitate the peptide. The precipitated peptide was filtered, washed with diethyl ether, and dried under vacuum. A crude peptide product thus obtained was dissolved in a mixture of 20% acetic acid/acetonitrile (volume ratio 1/1) and subjected to purification under the conditions described below. The peptide consisting of the sequence: PGCNKRYFKLSHLQMHSRK (Pro-Gly-Cys-Asn-Lys-Arg-Tyr-Phe-Lys-Leu-Ser-His-Leu-Gln-Met-His-Ser-Arg-Lys) (SEQ ID NO: 5) (0.16 g) was obtained.

Purification Conditions:
  HPLC System: Gilson high throughput preparative HPLC system
  Column: YMC ODS-A 3 cm φ×25 cm, 10 μm
  Eluent 1: 0.1% TFA in water
  Fluent 2: 0.035% TFA in acetonitrile
  Flow rate: 20 ml/min
Gradient Method:

| Time (min.) | Concentration of Eluent 2 (%) |
|---|---|
| 0 | 10 |
| 15 | 10 |
| 25 | 22 |
| 45 | 27 |

Identification of the product was conducted by analysis under the following conditions:
  MS System: Shimazu LCMS-IT-TOF system
  Column: Kinetex Minibore column, 2.1 mm φ×50 mm, 1.7 μm
  Eluent 1: 0.1% formic acid in water
  Eluent 2: 0.1% formic acid in acetonitrile
  Flow rate: 1.2 ml/min
Gradient Method

| Time (min.) | Concentration of Eluent 2 (%) |
|---|---|
| 0 | 10 |
| 1.4 | 95 |
| 1.6 | 95 |

MS: m/z = 1166.10 $[M + 2H]^{2+}$, retention time: 0.68 min.

Examples 2 to 10

In accordance with the procedure as described in Example 1, peptides listed in Table 1 below were synthesized from corresponding starting materials:

TABLE 1

| Example No. | SEQ ID NO: | Amino Acid Sequence | LC-TOFMS (m/z, retention time (min.)) |
|---|---|---|---|
| 2 | 6 | GCNKRYFKLSHLQMHSRK | 1117.57 $[M + 2H]^{2+}$, 0.77 |
| 3 | 2 | AYPGCNKRYFKLSHL | 1798.83 $[M + H]^{+}$, 0.80 |
| 4 | 3 | YPGCNKRYFKLSHLQ | 1854.88 $[M + H]^{+}$, 0.82 |
| 5 | 8 | NKRYFKLSHLQMHSRK | 1037.55 $[M + 2H]^{2+}$, 0.67 |
| 6 | 9 | KRYFKLSHLQMHSRK | 490.73 $[M + 4H]^{4+}$, 0.74 |
| 7 | 11 | RYFKLSHLQMHSRKH | 493.00 $[M + 4H]^{4+}$, 0.71 |

TABLE 1-continued

| Example No. | SEQ ID NO: | Amino Acid Sequence | LC-TOFMS (m/z, retention time (min.)) |
|---|---|---|---|
| 8 | 12 | YFKLSHLQMHSRKHT | 479.23 $[M + 4H]^{4+}$, 0.72 |
| 9 | 13 | FKLSHLQMHSRKHTG | 452.72 $[M + 4H]^{4+}$, 0.71 |
| 10 | 14 | KLSHLQMHSRKHTGE | 448.21 $[M + 4H]^{4+}$, 0.30 |

Reference Examples 1 to 6

In accordance with the procedure as described in Example 1, peptides listed in Table 2 below were synthesized from corresponding starting materials:

TABLE 2

| Reference Example No. | SEQ ID NO: | Amino Acid Sequence or Structure | LC-TOFMS (m/z, retention time (min.)) |
|---|---|---|---|
| 1 | 15 | RMFPNAPYL | 554.73 $[M + 2H]^{2+}$, 0.82 |
| 2 | 17 | CYTWNQMNL | 586.69 $[M + 2H]^{+2}$, 0.87 |
| 3 | 35 | C(Npys)RMFPNAPYL | 683.21 $[M + 2H]^{2+}$, 0.95 |
| 4 | 4 | PGCNKRYFKLSHLQMH SRKHTG | 1313.66 $[M + 2H]^{2+}$, 0.76 |
| 5 | 7 | CNKRYFKLSHLQMHSRK | 436.19 $[M + 5H]^{5+}$, 0.64 |
| 6 | 10 | KRYFKLSHLQMHSRKII | 420.23 $[M + 5H]^{5+}$, 0.24 |

In accordance with a procedure described in WO 2014/157692, a compound shown in Table 3 below was synthesized. (In the structural formula shown in Table 3, C—C means that the C residues are linked together by a disulfide bond.)

TABLE 3

| Reference Example No. | Formula | Structure | LC-TOFMS (m/z, retention time (min.)) |
|---|---|---|---|
| 7 | (4) | 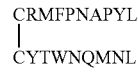 | 794.60 $[M + 3H]^{3+}$, 0.88 |

Experimental Example 1

In Vivo CTL Induction in HLA-A*02:01 Transgenic Mouse

A cocktail vaccine comprising the compound of formula (4) synthesized in Reference Example 7 and the peptide of SEQ ID NO: 5 synthesized in Example 1 was prepared and evaluated for ability to induce CTLs in vivo in an HLA-A*02:01 transgenic mouse. In the compound of formula (4):

$$\begin{array}{c} \text{CRMFPNAPYL} \\ | \\ \text{CYTWNQMNL} \end{array} \quad (4)$$

wherein C—C shown means that the C residues are linked together by a disulfide linkage, the sequence RMFPNAPYL (SEQ ID NO: 15) corresponds to an HLA-A*02:01-restricted WT1 peptide, and the sequence CYTWNZMNL (SEQ ID NO: 17) corresponds to an HLA-A*24:02-restricted WT1 peptide.

The HLA-A*02:01 transgenic mouse (C57BL/6CrHLA-A2.1DR1) lacks mouse MHC, and instead expresses a chimeric IILA of a human MHC, HLA-A*02:01 with a mouse MHC, H-2Db, and HLA-DRB1*01:01. The mouse is useful for screening peptides for potential ability to induce CTLs in HLA-A*02:01-positive human (Eur J Immunol. 2004; 34: 3060-9), and also for evaluating helper peptides that can bind to the human MHC, HLA-DRB1*01:01 and induce helper T cells for ability to enhance CTL induction.

Induction of CTLs specific to the peptide of SEQ ID NO: 15 by the cocktail vaccine of the compound of formula (4) and the peptide of SEQ ID NO: 5 in the mouse was measured, compared with a vaccine comprising the compound of formula (4) alone, as the level of IFNγ produced by splenocytes from the mouse upon stimulation of the cells with the peptide of SEQ ID NO: 15. Increase in the number of CTLs specific to the peptide of SEQ ID NO: 15 in a sample from a mouse treated with the cocktail vaccine comprising the peptide of SEQ ID NO: 5 and the compound of formula (4) compared with a sample from a mouse treated with the vaccine comprising the compound of formula (4) reflects the effect of co-administration of the peptide of SEQ ID NO: 5 with the compound of formula (4) on the CTL induction.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 5 (298.67 mg/ml) in DMSO was prepared, diluted with water for injection to concentrations of the compound of formula (4) of 10 mg/ml and the peptide of SEQ ID NO: 5 of 11.2 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 280 µg of the peptide of SEQ ID NO: 5 per site. The cocktail vaccine was prepared to comprise the compound of formula (4) and the peptide of SEQ ID NO: 5 in a molar ratio of 1:1.14. One week after the administration, the mice were sacrificed with $CO_2$ gas. Splenocytes were harvested from spleens removed from the mice. For detecting IFNγ-producing splenocytes, an IFNγ ELISPOT assay kit was used. In particular, an ELISPOT plate was treated with an anti-mouse-IFNγ antibody on the day before preparation of the splenocyte samples. On the next day, the plate was blocked by treatment with an RPMI 1640 medium with 10% FBS. To the blocked ELISPOT plate, the splenocyte samples from the HLA-A*02:01 transgenic mice were added at $1.25 \times 10^5$ cells/well.

For in vitro stimulation of the cells, the peptide of SEQ ID NO: 15 was dissolved in DMSO at a concentration of 40 mg/ml, diluted with RPMI 1640 with 10% FBS to 40 μg/ml, and added to the splenocyte-containing wells at a final concentration of 10 μg/ml. The plate was incubated for 17 hours at 37° C. under an atmosphere of 5% $CO_2$. Then, after removal of the culture medium from the wells, the ELISPOT plate was subjected to treatment for cell staining in accordance with the manufacturer's protocol. Stained spots were counted on ImmunoSpot Analyzer (C.T.L.).

FIG. 1 shows results from the IFNγ ELISPOT assay using the HLA-A*02:01 transgenic mouse. The scale on the vertical axis of the graph of FIG. 1 indicates the number of cells (CTLs) which produced IFNγ in response to the stimulation with the peptide of SEQ ID NO: 15. The compound and the peptide administered to the mice are described under the bars. The black bar shows the number of splenocytes which produced IFNγ in response to the stimulation with the peptide of SEQ ID NO: 15. The white bar shows the number of splenocytes which produced IFNγ in the absence of the peptide stimulation. Therefore, effect of each vaccine in CTL induction is known from the difference in cell count between the black bar and the white bar. When no IFNγ is produced by cells in the absence of the stimulation with SEQ ID NO: 15, a white bar cannot have a height. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 5 in addition to the compound of formula (4).

The cocktail vaccine comprising the peptide of SEQ ID NO: 5 in addition to the compound of formula (4) was highly effective in CTL induction as confirmed with the increase in the number of CTLs induced in the mice treated with the cocktail vaccine compared with the vaccine comprising the compound of formula (4).

Experimental Example 2

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 6 synthesized in Example 2 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VC. The emulsion was injected to mice intradermally at two sites in the tail base area in an amount for administering 250 μg of the compound of formula (4) per site. On the other hand, a solution of the compound of formula (4) (266.67 mg/ml) and the peptide of SEQ ID NO: 6 (282.67 mg/ml) in DMSO was prepared, diluted with water for injection to concentrations of the compound of formula (4) of 10 mg/ml and the peptide of SEQ ID NO: 6 of 10.6 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 265 μg of the peptide of SEQ ID NO: 6 per site. The cocktail vaccine was prepared to comprise the compound of formula (4) and the peptide of SEQ ID NO: 6 in a molar ratio of 1:1.14.

Figure 2:
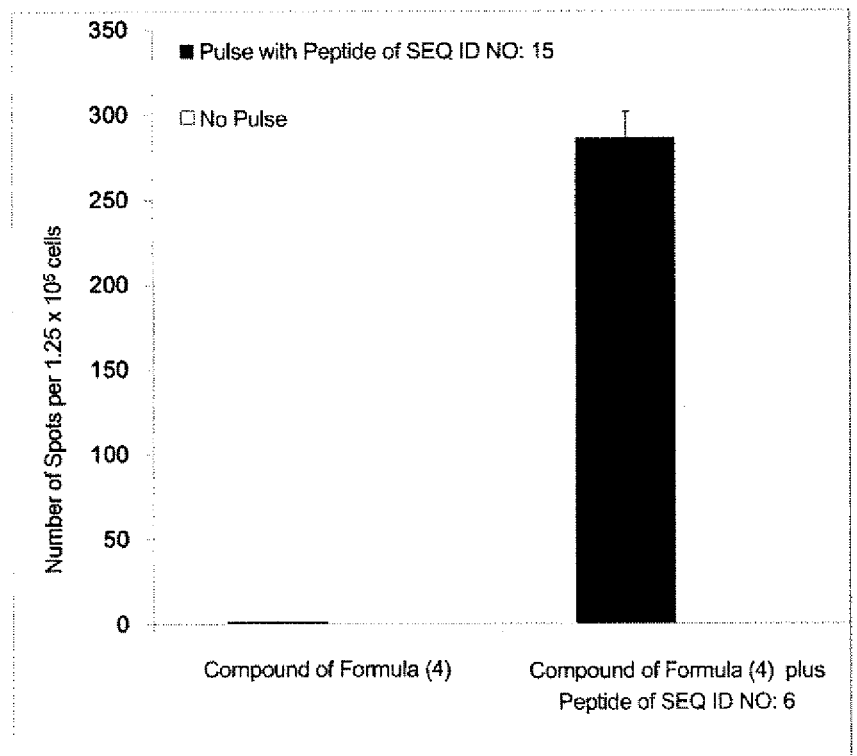
FIG. 2 shows in vivo CTL induction in an HLA-A*02:01 transgenic mouse by a cocktail vaccine comprising the compound of formula (4) synthesized in Reference Example 7 and the peptide of SEQ ID NO: 6 in an IFNγ ELISOPOT assay of Experimental Example 1.

FIG. 2 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 6 in addition to the compound of formula (4).

The cocktail vaccine comprising the peptide of SEQ ID NO: 6 in addition to the compound of formula (4) was highly effective in CTL induction as confirmed with the increase in the number of CTLs induced in the mice treated with the cocktail vaccine compared with the vaccine comprising the compound of formula (4).

Comparison Example 1

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 7 synthesized in Reference Example 5 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (266.67 mg/ml) and the peptide of SEQ ID NO: 7 (277.33 mg/ml) in DMSO was prepared, diluted with water for injection to concentrations of the compound of formula (4) of 1.0 mg/ml and the peptide of SEQ ID NO: 7 of 10.4 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 260 μg of the peptide of SEQ ID NO: 7 per site. The cocktail vaccine was prepared to comprise the compound of formula (4) and the peptide of SEQ ID NO: 7 in a molar ratio of 1:1.14.

Figure 3:
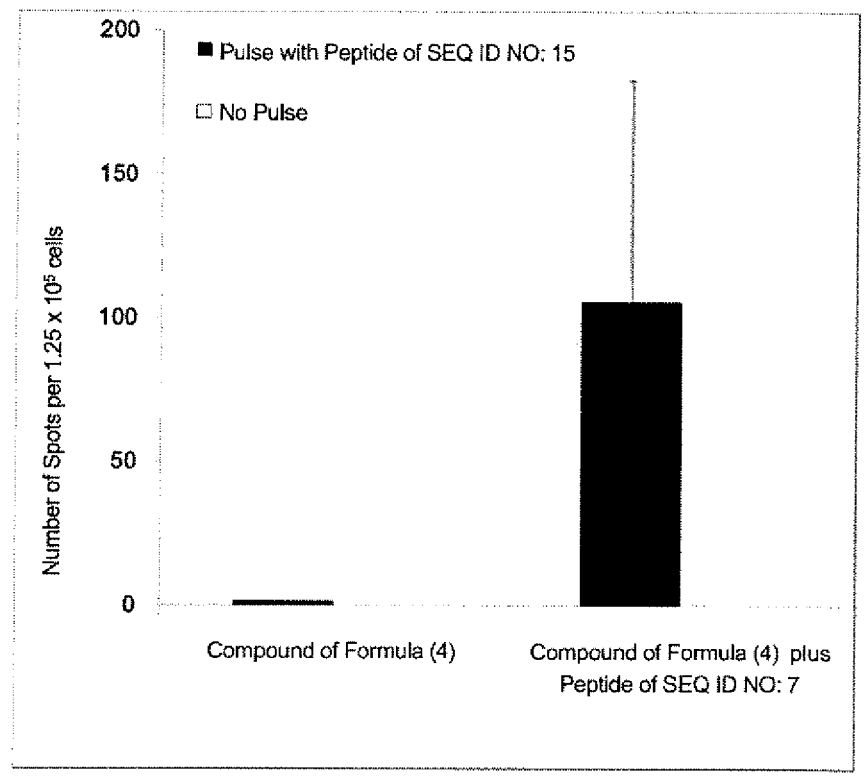
FIG. 3 shows in vivo CTL induction in an HLA-A*02:01 transgenic mouse by a cocktail vaccine comprising the compound of formula (4) synthesized in Reference Example 7 and the peptide of SEQ ID NO: 7 in an IFNγ ELISOPOT assay of Comparison Example 1.

FIG. 3 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 7 in addition to the compound of formula (4).

The cocktail vaccine comprising the peptide of SEQ ID NO: 7 in addition to the compound of formula (4) was highly effective in CTL induction as confirmed with the increase in the number of CTLs induced in the mice treated with the cocktail vaccine compared with the vaccine comprising the compound of formula (4).

Experimental Example 3

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 8 synthesized in Example 5 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (266.67 mg/ml) and the peptide of SEQ ID NO: 8 (261.33 mg/ml) in DMSO was prepared, diluted with water for injection to concentrations of the compound of formula (4) of 10 mg/ml and the peptide of SEQ ID NO: 8 of 9.8 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 245 μg of the peptide of SEQ ID NO: 8 per site. The cocktail vaccine was prepared to comprise the compound of formula (4) and the peptide of SEQ ID NO: 8 in a molar ratio of 1:1.14.

Figure 4:
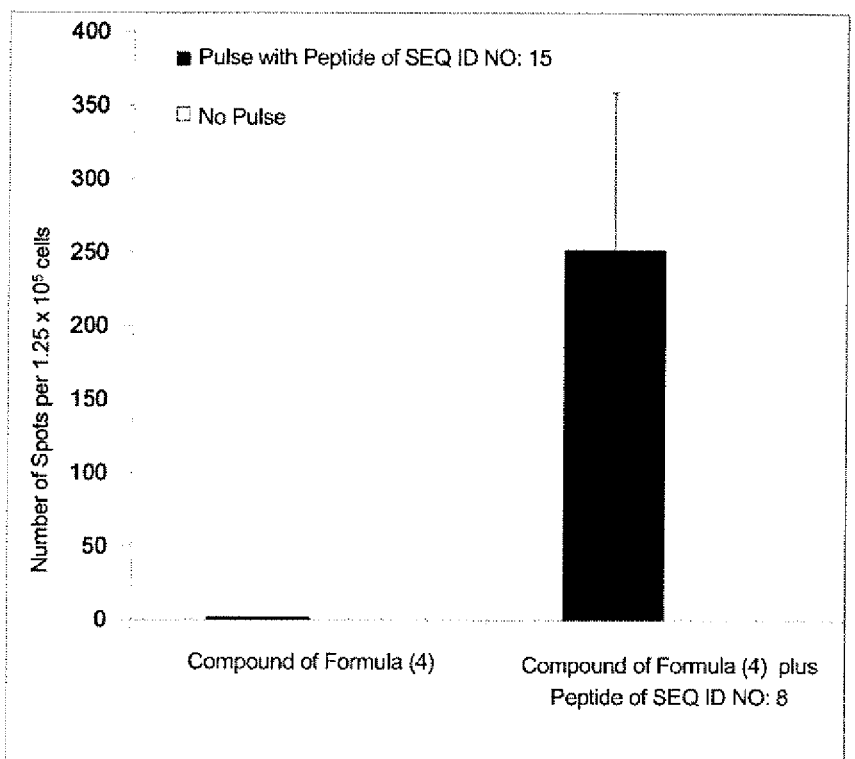
FIG. 4 shows in vivo CTL induction in an HLA-A*02:01 transgenic mouse by a cocktail vaccine comprising the compound of formula (4) synthesized in Reference Example 7 and the peptide of SEQ ID NO: 8 in an IFNγ ELISOPOT assay of Experimental Example 3.

FIG. 4 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 8 in addition to the compound of formula (4).

The cocktail vaccine comprising the peptide of SEQ ID NO: 8 in addition to the compound of formula (4) was highly effective in CTL induction as confirmed with the increase in the number of CTLs induced in the mice treated with the cocktail vaccine compared with the vaccine comprising the compound of formula (4).

Experimental Example 4

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 9 synthesized in Example 6 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (266.67 mg/ml) and the peptide of SEQ ID NO: 9 (250.67 mg/ml) in DMSO was prepared, diluted with water for injection to concentrations of the compound of formula (4) of 10 mg/ml and the peptide of SEQ ID NO: 9 of 9.4 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 235 μg of the peptide of SEQ ID NO: 9 per site. The cocktail vaccine was prepared to comprise the compound of formula (4) and the peptide of SEQ ID NO: 9 in a molar ratio of 1:1.14.

Figure 5:
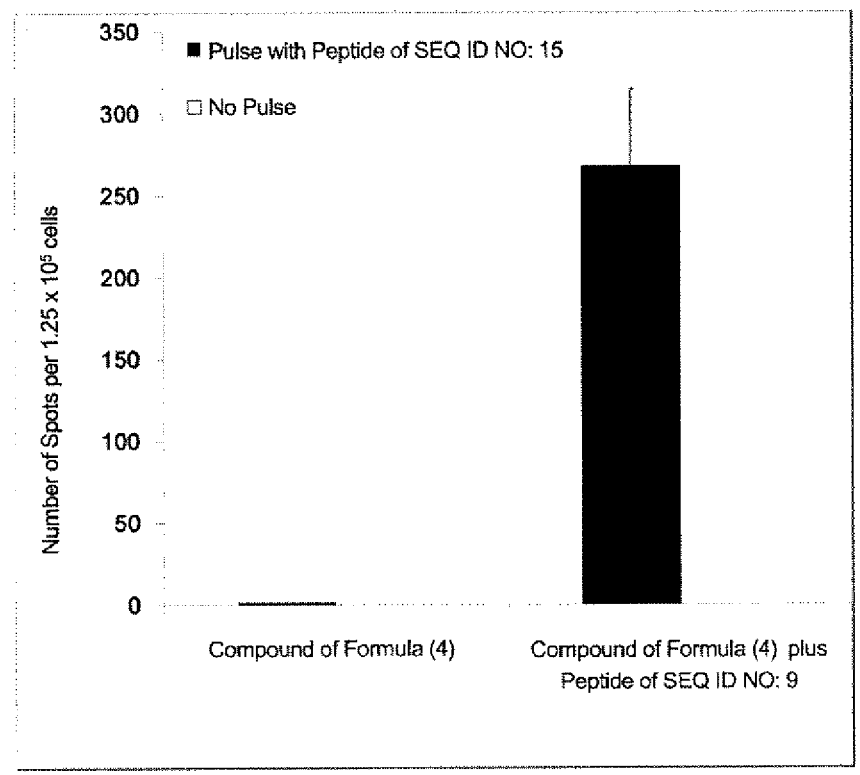
FIG. 5 shows in vivo CTL induction in an HLA-A*02:01 transgenic mouse by a cocktail vaccine comprising the compound of formula (4) synthesized in Reference Example 7 and the peptide of SEQ ID NO: 9 in an IFNγ ELISOPOT assay of Experimental Example 4.

FIG. 5 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 9 in addition to the compound of formula (4).

The cocktail vaccine comprising the peptide of SEQ ID NO: 9 in addition to the compound of formula (4) was highly effective in CTL induction as confirmed with the increase in the number of CTLs induced in the mice treated with the cocktail vaccine compared with the vaccine comprising the compound of formula (4).

Experimental Example 5

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 2 synthesized in Example 3 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (266.67 mg/ml) and the peptide of SEQ ID NO: 2 (231.11 mg/ml) in DMSO was prepared, diluted with water for injection to concentrations of the compound of formula (4) of 10 mg/ml and the peptide of SEQ ID NO: 2 of 8.7 mg/mil, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 215 μg of the peptide of SEQ ID NO: 2 per site. The cocktail vaccine was prepared to comprise the compound of formula (4) and the peptide of SEQ ID NO: 2 in a molar ratio of 1:1.14.

Figure 6:
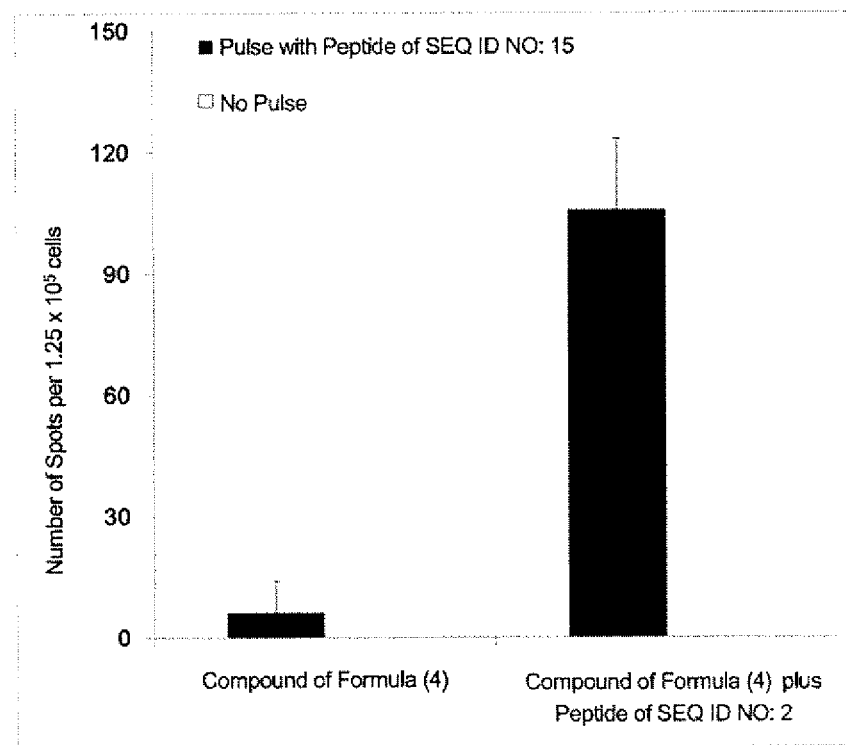
FIG. 6 shows in vivo CTL induction in an HLA-A*02:01 transgenic mouse by a cocktail vaccine comprising the compound of formula (4) synthesized in Reference Example 7 and the peptide of SEQ ID NO: 2 in an IFNγ ELISOPOT assay of Experimental Example 5.

FIG. 6 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 2 in addition to the compound of formula (4).

The cocktail vaccine comprising the peptide of SEQ ID NO: 2 in addition to the compound of formula (4) was highly effective in CTL induction as confirmed with the increase in the number of CTLs induced in the mice treated with the cocktail vaccine compared with the vaccine comprising the compound of formula (4).

Experimental Example 6

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 3 synthesized in Example 4 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 3 (235.56 mg/ml) in DMSO was prepared, diluted with water for injection to concentrations of the compound of formula (4) of 10 mg/ml and the peptide of SEQ ID NO: 3 of 8.8 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 220 µg of the peptide of SEQ ID NO: 3 per site. The cocktail vaccine was prepared to comprise the compound of formula (4) and the peptide of SEQ ID NO: 3 in a molar ratio of 1:1.13.

Figure 7:
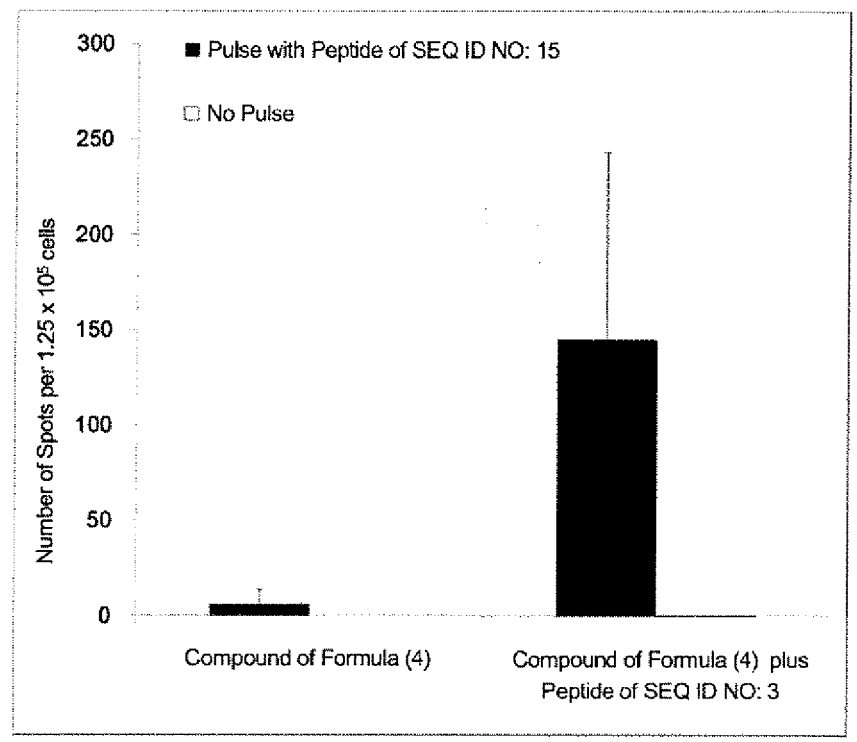
FIG. 7 shows in vivo CTL induction in an HLA-A*02:01 transgenic mouse by a cocktail vaccine comprising the compound of formula (4) synthesized in Reference Example 7 and the peptide of SEQ ID NO: 3 in an IFNγ ELISOPOT assay of Experimental Example 6.

FIG. 7 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 3 in addition to the compound of formula (4).

The cocktail vaccine comprising the peptide of SEQ ID NO: 3 in addition to the compound of formula (4) was highly effective in CTL induction as confirmed with the increase in the number of CTLs induced in the mice treated with the cocktail vaccine compared with the vaccine comprising the compound of formula (4).

Experimental Example 7

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 4 synthesized in Reference Example 4 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 4 (336.00 mg/ml) in DMSO was prepared, diluted with water for injection to concentrations of the compound of formula (4) of 10 mg/ml and the peptide of SEQ ID NO: 4 of 12.6 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 315 µg of the peptide of SEQ ID NO: 4 per site. The cocktail vaccine was prepared to comprise the compound of formula (4) and the peptide of SEQ ID NO: 4 in a molar ratio of 1:1.14.

Figure 8:
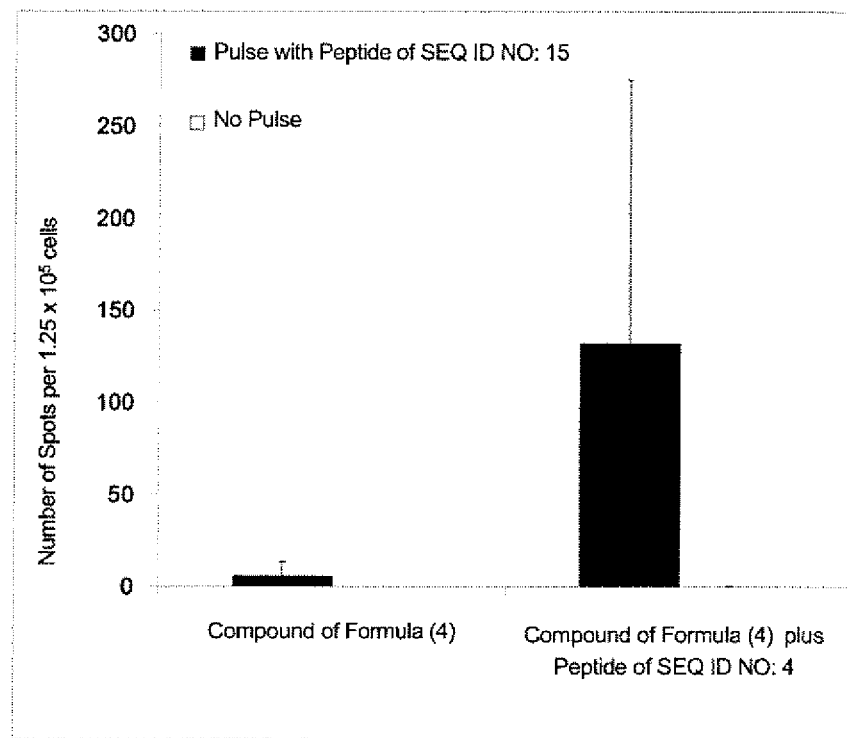
FIG. 8 shows in vivo CTL induction in an HLA-A*02:01 transgenic mouse by a cocktail vaccine comprising the compound of formula (4) synthesized in Reference Example 7 and the peptide of SEQ ID NO: 4 in an IFNγ ELISOPOT assay of Experimental Example 7.

FIG. 8 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 4 in addition to the compound of formula (4).

The cocktail vaccine comprising the peptide of SEQ ID NO: 4 in addition to the compound of formula (4) was highly effective in CTL induction as confirmed with the increase in the number of CTLs induced in the mice treated with the cocktail vaccine compared with the vaccine comprising the compound of formula (4).

Experimental Example 8

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 10 synthesized in Reference Example 6 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 10 (266.67 mg/ml) in DMSO was prepared, diluted with water for injection to concentrations of the compound of formula (4) of 10 mg/ml and the peptide of SEQ ID NO: 10 of 10 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 250 µg of the peptide of SEQ ID NO: 10 per site. The cocktail vaccine was prepared to comprise the compound of formula (4) and the peptide of SEQ ID NO: 10 in a molar ratio of 1:1.14.

Figure 9:
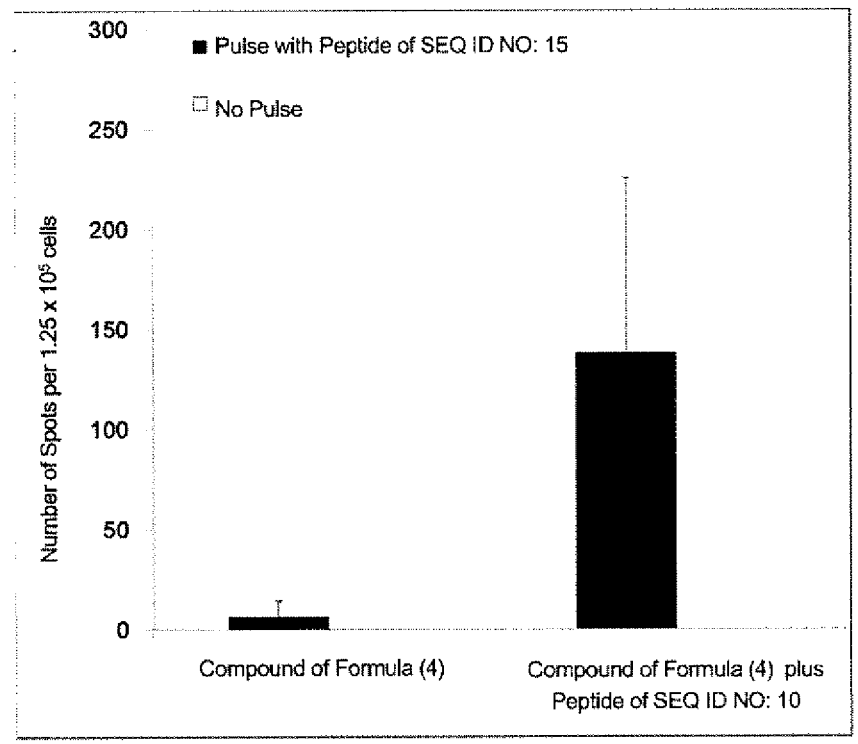
FIG. 9 shows in vivo CTL induction in an HLA-A*02:01 transgenic mouse by a cocktail vaccine comprising the compound of formula (4) synthesized in Reference Example 7 and the peptide of SEQ ID NO: 10 in an IFNγ ELISOPOT assay of Experimental Example 8.

FIG. 9 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 10 in addition to the compound of formula (4).

The cocktail vaccine comprising the peptide of SEQ ID NO: 10 in addition to the compound of formula (4) was highly effective in CTL induction as confirmed with the increase in the number of CTLs induced in the mice treated with the cocktail vaccine compared with the vaccine comprising the compound of formula (4).

Experimental Example 9

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 11 synthesized in Example 7 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 11 (248.89 mg/ml) in DMSO was prepared, diluted with water for injection to concentrations of the compound of formula (4) of 10 mg/ml and the peptide of SEQ ID NO: 11 of 9.3 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 235 µg of the peptide of SEQ ID NO: 11 per site. The cocktail vaccine was prepared to comprise the compound of formula (4) and the peptide of SEQ ID NO: 11 in a molar ratio of 1:1.14.

Figure 10:
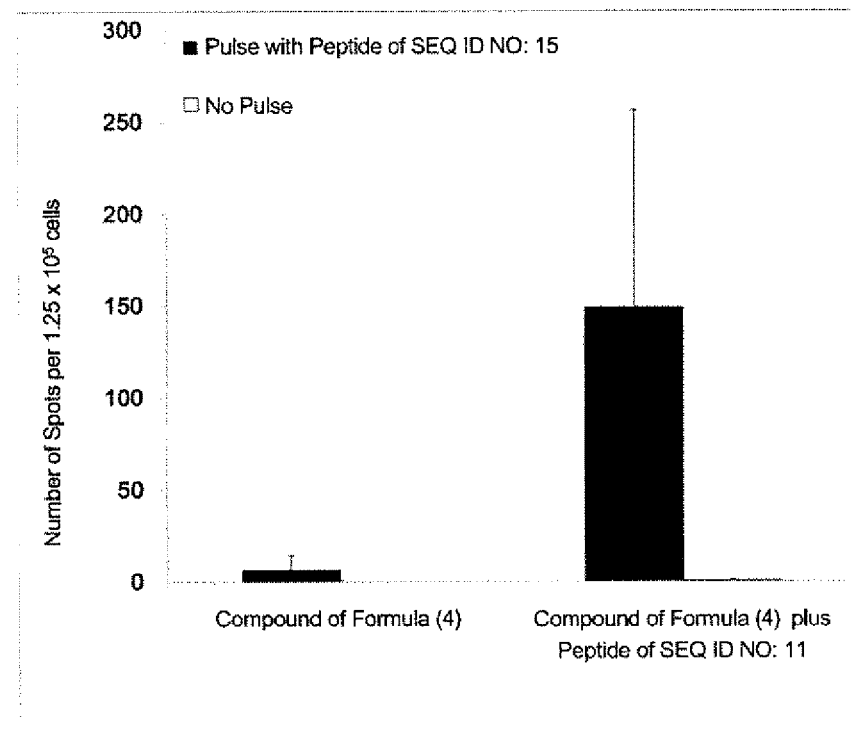
FIG. 10 shows in vivo CTL induction in an HLA-A*02:01 transgenic mouse by a cocktail vaccine comprising the compound of formula (4) synthesized in Reference Example 7 and the peptide of SEQ ID NO: 11 in an IFNγ ELISOPOT assay of Experimental Example 9.

FIG. 10 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 11 in addition to the compound of formula (4).

The cocktail vaccine comprising the peptide of SEQ ID NO: 11 in addition to the compound of formula (4) was highly effective in CTL induction as confirmed with the increase in the number of CTLs induced in the mice treated with the cocktail vaccine compared with the vaccine comprising the compound of formula (4).

Experimental Example 10

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 12 synthesized in Example 8 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 12 (244.44 mg/ml) in DMSO was prepared, diluted with water for injection to concentrations of the compound of formula (4) of 10 mg/ml and the peptide of SEQ ID NO: 12 of 9.2 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 230 µg of the peptide of SEQ ID NO: 12 per site. The cocktail vaccine was prepared to comprise the compound of formula (4) and the peptide of SEQ ID NO: 12 in a molar ratio of 1:1.15.

Figure 11:
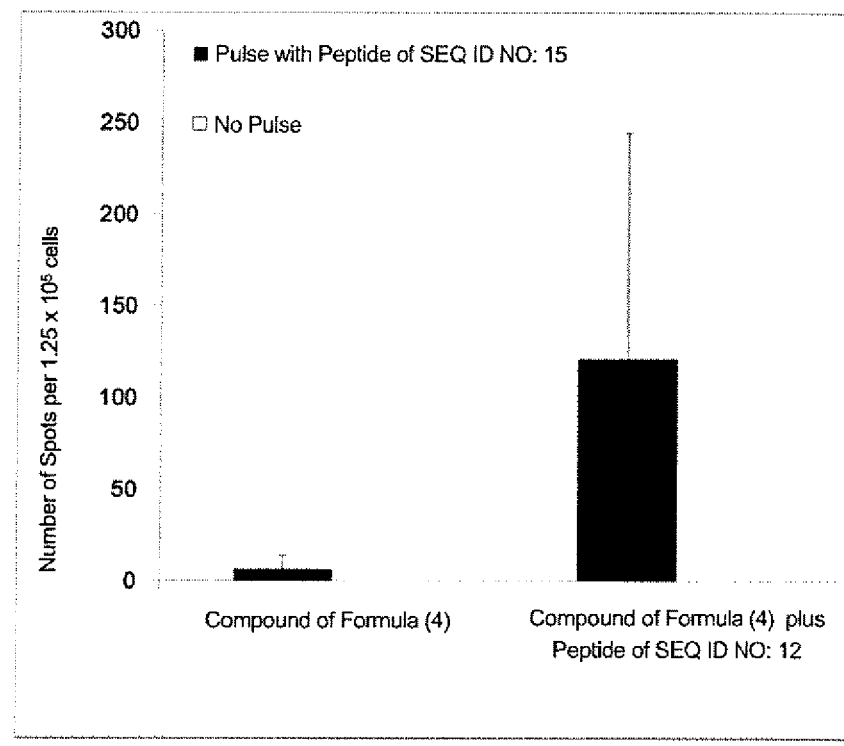
FIG. 11 shows in vivo CTL induction in an HLA-A*02:01 transgenic mouse by a cocktail vaccine comprising the compound of formula (4) synthesized in Reference Example 7 and the peptide of SEQ ID NO: 12 in an IFNγ ELISOPOT assay of Experimental Example 10.

FIG. 11 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 12 in addition to the compound of formula (4).

The cocktail vaccine comprising the peptide of SEQ ID NO: 12 in addition to the compound of formula (4) was highly effective in CTL induction as confirmed with the increase in the number of CTLs induced in the mice treated with the cocktail vaccine compared with the vaccine comprising the compound of formula (4).

Experimental Example 11

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 13 synthesized in Example 9 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 13 (231.11 mg/ml) in DMSO was prepared, diluted with water for injection to concentrations of the compound of formula (4) of 10 mg/ml and the peptide of SEQ ID NO: 13 of 8.7 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 215 µg of the peptide of SEQ ID NO: 13 per site. The cocktail vaccine was prepared to comprise the compound of formula (4) and the peptide of SEQ ID NO: 13 in a molar ratio of 1:1.13.

Figure 12:
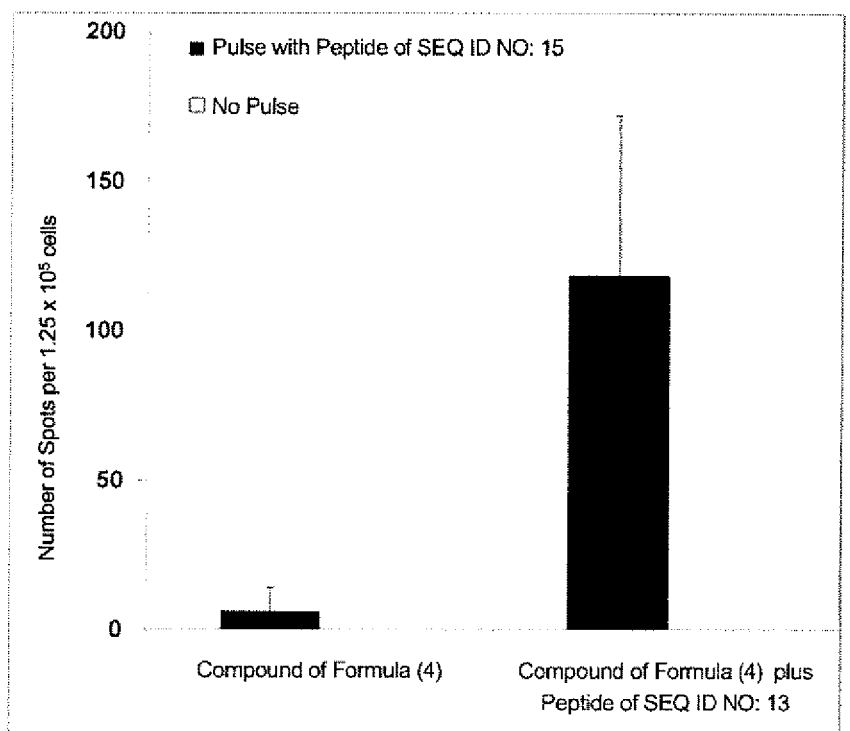
FIG. 12 shows in vivo CTL induction in an HLA-A*02:01 transgenic mouse by a cocktail vaccine comprising the compound of formula (4) synthesized in Reference Example 7 and the peptide of SEQ ID NO: 13 in an IFNγ ELISOPOT assay of Experimental Example 11.

FIG. 12 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 13 in addition to the compound of formula (4).

The cocktail vaccine comprising the peptide of SEQ ID NO: 13 in addition to the compound of formula (4) was highly effective in CTL induction as confirmed with the increase in the number of CTLs induced in the mice treated with the cocktail vaccine compared with the vaccine comprising the compound of formula (4).

Experimental Example 12

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 14 synthesized in Example 10 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (266.67 mg/ml) and the peptide of SEQ ID NO: 14 (231.11 mg/ml) in DMSO was prepared, diluted with water for injection to concentrations of the compound of formula (4) of 10 mg/ml and the peptide of SEQ ID NO: 14 of 8.7 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 215 μg of the peptide of SEQ ID NO: 14 per site. The cocktail vaccine was prepared to comprise the compound of formula (4) and the peptide of SEQ ID NO: 14 in a molar ratio of 1:1.14.

Figure 13:
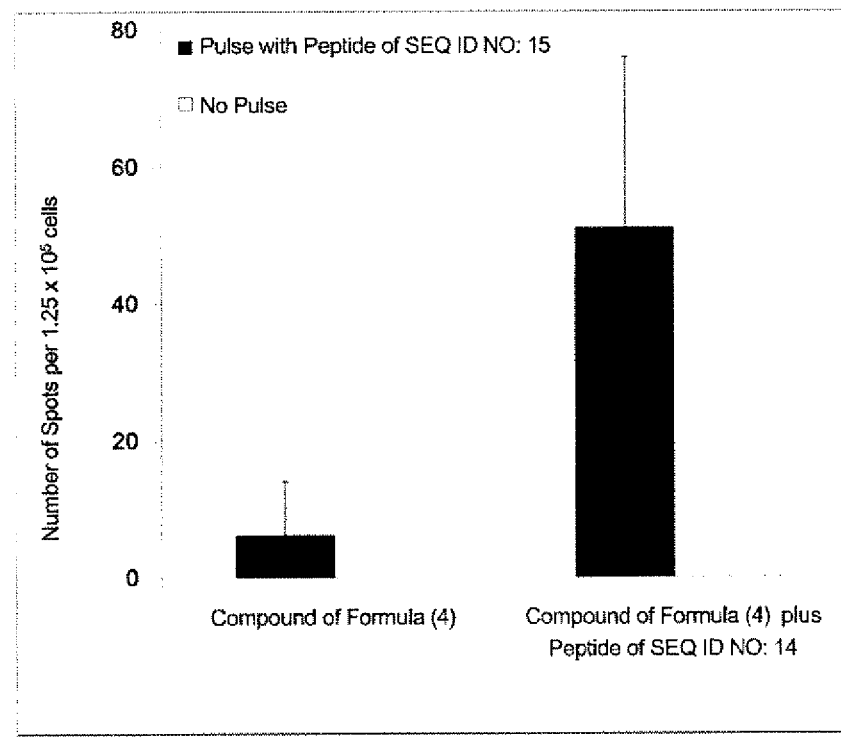
FIG. 13 shows in vivo CTL induction in an HLA-A*02:01 transgenic mouse by a cocktail vaccine comprising the compound of formula (4) synthesized in Reference Example 7 and the peptide of SEQ ID NO: 14 in an IFNγ ELISOPOT assay of Experimental Example 12.

FIG. 13 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 14 in addition to the compound of formula (4).

The cocktail vaccine comprising the peptide of SEQ ID NO: 14 in addition to the compound of formula (4) was highly effective in CTL induction as confirmed with the increase in the number of CTLs induced in the mice treated with the cocktail vaccine compared with the vaccine comprising the compound of formula (4).

Examples 1 to 40

In accordance with the procedure as described in Example 1, peptides listed in Tables 4-1 to 4-3 below were synthesized from corresponding starting materials:

TABLE 4-1

| Example No. | SEQ ID NO: | Amino Acid Sequence | LC-TOFMS (m/z, retention time (min.)) |
|---|---|---|---|
| 11 | 39 | RYFKLSHLQMHSRK | 458.70 [M + 4H]$^{+4}$, 0.85 |
| 12 | 40 | YFKLSHLQMHSRK | 423.15 [M + 4H]$^{+4}$, 0.76 |
| 13 | 41 | FKLSHLQMHSRK | 504.56 [M + 3H]$^{+3}$, 0.74 |

TABLE 4-1-continued

| Example No. | SEQ ID NO: | Amino Acid Sequence | LC-TOFMS (m/z, retention time (min.)) |
|---|---|---|---|
| 14 | 42 | KLSHLQMHSRK | 455.54 [M + 3H]$^{+3}$, 0.64 |
| 15 | 43 | AYPGCNKRYFKLSHLQMH | 439.95 [M + 5H]$^{+5}$, 0.91 |
| 16 | 44 | AYPGCNKRYFKLSHLQMHSRK | 428.36 [M + 6H]$^{+6}$, 0.82 |
| 17 | 45 | RYFKLSHLQMH | 487.24 [M + 3H]$^{+3}$, 0.28 |
| 18 | 46 | GCNKRYFKLSHL | 489.24 [M + 3H]$^{+3}$, 0.76 |
| 19 | 47 | FKLSHLQMHSRKHTGE | 485.00 [M + 4H]$^{+4}$, 0.80 |
| 20 | 48 | RYFKLSHLQMHSRKHT | 414.82 [M + 5H]$^{+5}$, 0.71 |

TABLE 4-2

| Example No. | SEQ ID NO: | Amino Acid Sequence | LC-TOFMS (m/z, retention time (min.)) |
|---|---|---|---|
| 21 | 49 | RYFKLSHLQMHSRKHTGE | 452.04 [M + 5H]$^{+5}$, 0.66 |
| 22 | 50 | KLSHLQMHSRKH | 501.28 [M + 3H]$^{+3}$, 0.35 |
| 23 | 51 | YPGCNKRYFKLSHLQMHSRK | 416.53 [M + 6H]$^{+6}$, 1.04 |
| 24 | 52 | AYPGCNKRYFKLSHLQMHSR | 488.22 [M + 5H]$^{+5}$, 0.98 |
| 25 | 53 | AYPGCNKRYFKLSHLQMHS | 457.00 [M + 5H]$^{+5}$, 0.99 |
| 26 | 54 | AYPGCNKRYFKLSHLQM | 514.98 [M + 4H]$^{+4}$, 1.02 |
| 27 | 55 | AYPGCNKRYFKLSHLQ | 482.22 [M + 4H]$^{+4}$, 1.00 |
| 28 | 56 | YFKLSHLQMHSRKHTGE | 420.80 [M + 5H]$^{+5}$, 0.95 |
| 29 | 57 | RYFKLSHLQMHSRKHTG | 426.20 [M + 5H]$^{+5}$, 0.67 |
| 30 | 58 | RYFKLSHLQMHSR | 426.45 [M + 4H]$^{+4}$, 0.90 |

TABLE 4-3

| Example No. | SEQ ID NO: | Amino Acid Sequence | LC-TOFMS (m/z, retention time (min.)) |
|---|---|---|---|
| 31 | 59 | RYFKLSHLQMHS | 516.24 [M + 3H]$^{+3}$, 0.89 |
| 32 | 60 | RYFKLSHLQM | 441.55 [M + 3H]$^{+3}$, 0.93 |

TABLE 4-3-continued

| Example No. | SEQ ID NO: | Amino Acid Sequence | LC-TOFMS (m/z, retention time (min.)) |
|---|---|---|---|
| 33 | 61 | YPGCNKRYFKLSHL | 432.45 [M + 4H]$^{+4}$, 0.76 |
| 34 | 62 | PGCNKRYFKLSHL | 521.59 [M + 3H]$^{+3}$, 0.75 |
| 35 | 63 | CNKRYFKLSHL | 470.23 [M + H]$^{+3}$, 0.75 |
| 36 | 64 | NKRYFKLSHL | 435.90 [M + H]$^{+3}$, 0.77 |
| 37 | 65 | KLSHLQMHSRKHTG | 415.96 [M + 4H]$^{+4}$, 0.45 |
| 38 | 66 | KLSHLQMHSRKHT | 534.93 [M + 3H]$^{+3}$, 0.26 |
| 39 | 67 | KLSHLQMHSRK | 455.57 [M + 3H]$^{+3}$, 0.35 |
| 40 | 68 | KLSHLQMHSR | 412.87 [M + 3H]$^{+3}$, 0.67 |

Experimental Example 13

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 39 synthesized in Example 11 was prepared and evaluated for ability to induce CTLs in vivo in an HLA-A*02:01 transgenic mouse.

Specifically, the compound of formula (4) was dissolved in dimethyl sulfoxide (DMSO) at a concentration of 133.33 mg/ml. The solution was diluted with water for injection to a concentration of 10 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (266.67 mg/ml) and the peptide of SEQ ID NO: 39 (231.11 mg/ml) in DMSO was prepared, diluted with water for injection to concentrations of the compound of formula (4) of 10 mg/ml and the peptide of SEQ 10 NO: 39 of 8.7 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 220 µg of the peptide of SEQ ID NO: 39 per site. The cocktail vaccine was prepared to comprise the compound of formula (4) and the peptide of SEQ ID NO: 39 in equimolar amounts. One week after the administration, the mice were sacrificed with CO$_2$ gas. Splenocytes were harvested from spleens removed from the mice and frozen-stored at −80° C. overnight. Then, the splenocytes from the HLA-A*02:01 transgenic mice were thawed and added to a blocked ELISPOT plate at 2.5×10$^5$ cells/well.

Figure 14:
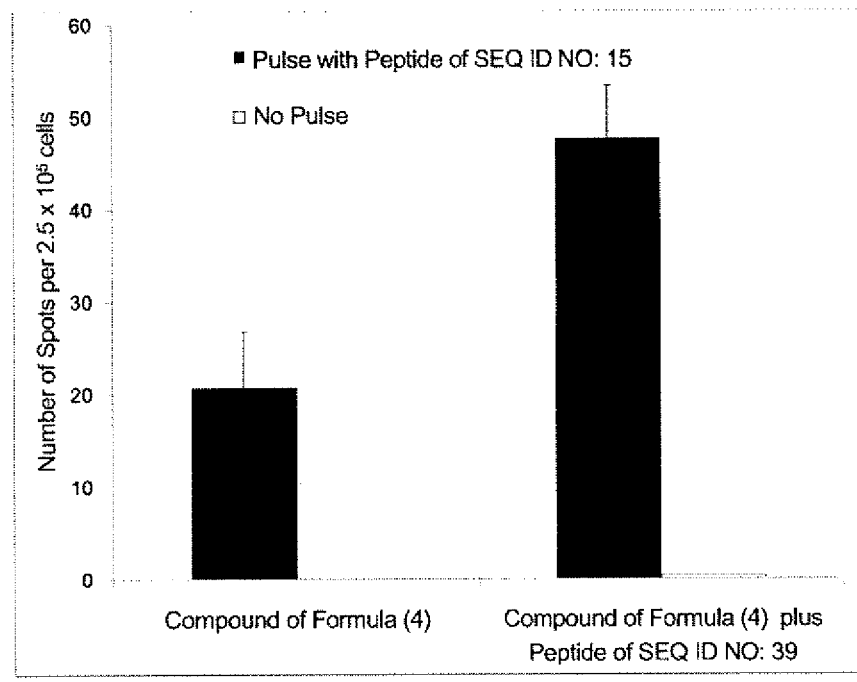
FIG. 14 shows in vivo CTL induction in an HLA-A*02:01 transgenic mouse by a cocktail vaccine comprising the compound of formula (4) synthesized in Reference Example 7 and the peptide of SEQ ID NO: 39 in an IFNγ ELISOPOT assay of Experimental Example 13.

FIG. 14 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 39 in addition to the compound of formula (4).

The cocktail vaccine comprising the peptide of SEQ ID NO: 39 in addition to the compound of formula (4) was highly effective in CTL induction as confirmed with the increase in the number of CTLs induced in the mice treated with the cocktail vaccine compared with the vaccine comprising the compound of formula (4).

Experimental Example 14

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 43 synthesized in Example 15 was prepared and evaluated for ability to induce CTLs in vivo in an HLA-A*02:01 transgenic mouse.

Specifically, the compound of formula (4) was dissolved in dimethyl sulfoxide (DMSO) at a concentration of 66.67 mg/ml. The solution was diluted with water for injection to a concentration of 5 mg/ml, and then converted to an emulsion by addition of an equal volume of Montanide ISA 51 VG. The emulsion was injected to mice intradermally at two sites in the tail base area in an amount for administering 250 µg of the compound of formula (4) per site. On the other hand, a solution of the compound of formula (4) (133.33 mg/ml) and the peptide of SEQ ID NO: 43 (137.5 mg/mi) in DMSO was prepared, diluted with water for injection to concentrations of the compound of formula (4) of 5 mg/ml and the peptide of SEQ ID NO: 43 of 5.2 mg/ml, and then converted into an emulsion by the addition of an equal volume of Montanide ISA 51 VG. The cocktail vaccine emulsion was injected to mice intradermally at two sites in the tail base area in an amount for administering 250 µg of the compound of formula (4) per site and 260 µg of the peptide of SEQ ID NO: 43 per site. The cocktail vaccine was prepared to comprise the compound of formula (4) and the peptide of SEQ ID NO: 43 in equimolar amounts.

Figure 15:
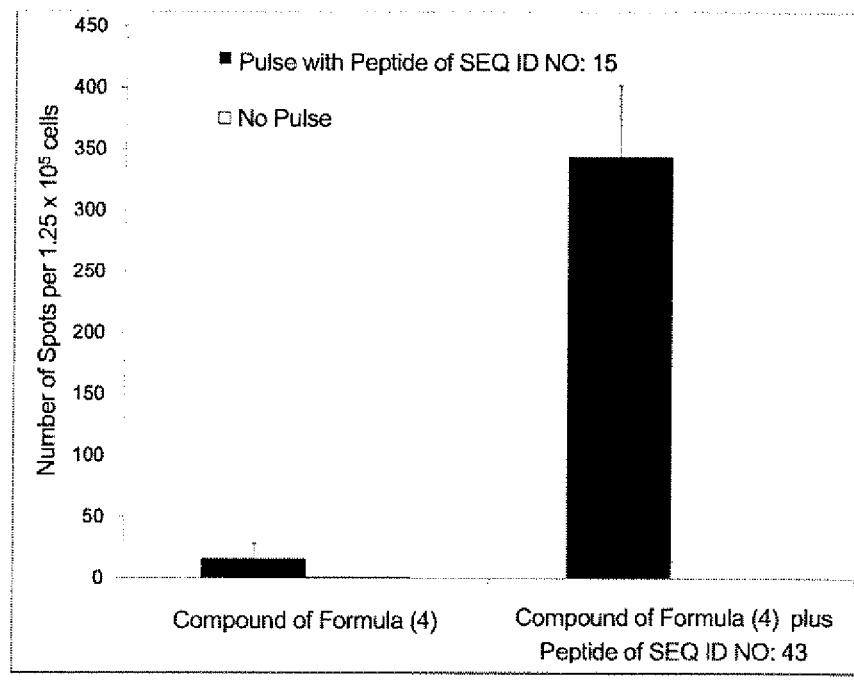
FIG. 15 shows in vivo CTL induction in an HLA-A*02:01 transgenic mouse by a cocktail vaccine comprising the compound of formula (4) synthesized in Reference Example 7 and the peptide of SEQ ID NO: 43 in an IFNγ ELISOPOT assay of Experimental Example 14.

FIG. 15 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 43 in addition to the compound of formula (4).

The cocktail vaccine comprising the peptide of SEQ ID NO: 43 in addition to the compound of formula (4) was highly effective in CTL induction as confirmed with the increase in the number of CTLs induced in the mice treated with the cocktail vaccine compared with the vaccine comprising the compound of formula (4).

Experimental Example 15

In Vivo CTL Induction in HLA-A02:01 Transgenic Mouse

In accordance with the procedure as described in Experimental Example 1, a cocktail vaccine comprising the compound of formula (4) synthesized in Reference Example 7 and the peptide of SEQ ID NO: 44 synthesized in Example 16 was prepared and evaluated for ability to induce CTLs in vivo in an HLA-A*02:01 transgenic mouse.

Specifically, the compound of formula (4) was dissolved in dimethyl sulfoxide (DMSO) at a concentration of 66.67 mg/ml. The solution was diluted with water for injection to a concentration of 5 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (133.33 mg/ml) and the peptide of SEQ ID NO: 44 (166.67 mg/ml) in DMSO was prepared, diluted with water for injection to concentrations of the compound of formula (4) of 5 mg/ml and the peptide of SEQ ID NO: 44 of 6.2 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 310 μg of the peptide of SEQ ID NO: 44 per site. The cocktail vaccine was prepared to comprise the compound of formula (4) and the peptide of SEQ ID NO: 44 in equimolar amounts.

Figure 16:
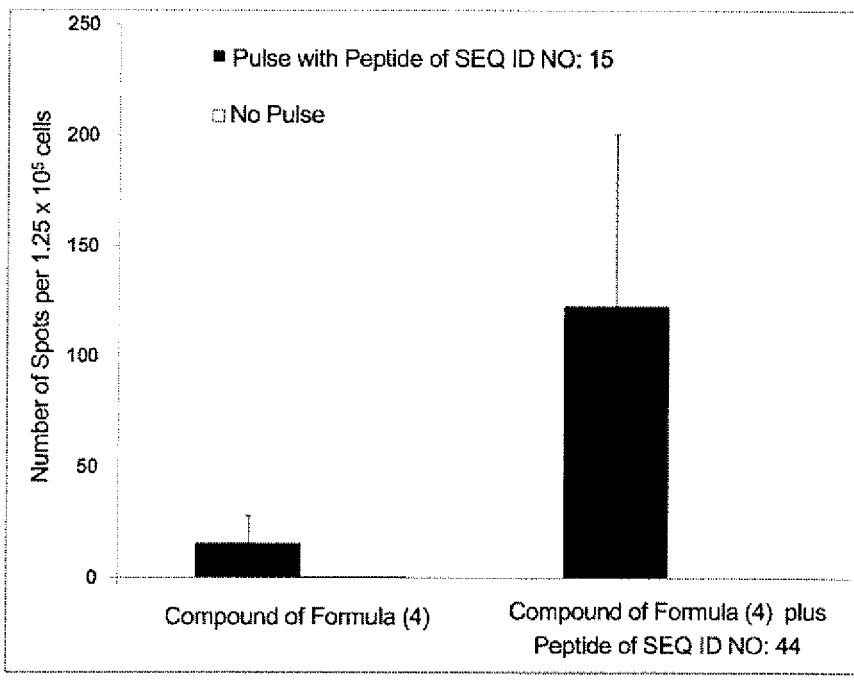
FIG. 16 shows in vivo CTL induction in an HLA-A*02:01 transgenic mouse by a cocktail vaccine comprising the compound of formula (4) synthesized in Reference Example 7 and the peptide of SEQ ID NO: 44 in an IFNγ ELISOPOT assay of Experimental Example 15.

FIG. 16 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 44 in addition to the compound of formula (4).

The cocktail vaccine comprising the peptide of SEQ ID NO: 44 in addition to the compound of formula (4) was highly effective in CTL induction as confirmed with the increase in the number of CTLs induced in the mice treated with the cocktail vaccine compared with the vaccine comprising the compound of formula (4).

Experimental Example 16

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 45 synthesized in Example 17 was prepared and evaluated for ability to induce CTLs in vivo in an HLA-A*02:01 transgenic mouse.

Specifically, the compound of formula (4) was dissolved in dimethyl sulfoxide (DMSO) at a concentration of 66.67 mg/ml. The solution was diluted with water for injection to a concentration of 5 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (133.33 mg/ml) and the peptide of SEQ ID NO: 45 (91.67 mg/ml) in DMSO was prepared, diluted with water for injection to concentrations of the compound of formula (4) of 5 mg/ml and the peptide of SEQ ID NO: 45 of 3.4 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 170 μg of the peptide of SEQ ID NO: 45 per site. The cocktail vaccine was prepared to comprise the compound of formula (4) and the peptide of SEQ ID NO: 45 in equimolar amounts.

Figure 17:
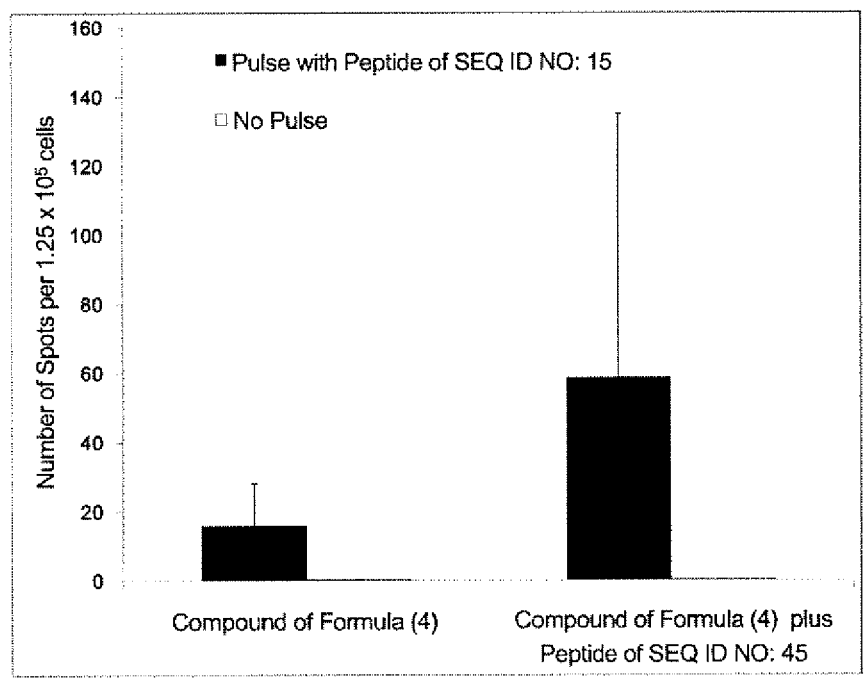
FIG. 17 shows in vivo CTL induction in an HLA-A02:01 transgenic mouse by a cocktail vaccine comprising the compound of formula (4) synthesized in Reference Example 7 and the peptide of SEQ ID NO: 45 in an IFNγ ELISOPOT assay of Experimental Example 16.

FIG. 17 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 45 in addition to the compound of formula (4).

The cocktail vaccine comprising the peptide of SEQ ID NO: 45 in addition to the compound of formula (4) was highly effective in CTL induction as confirmed with the increase in the number of CTLs induced in the mice treated with the cocktail vaccine compared with the vaccine comprising the compound of formula (4).

Experimental Example 17

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 46 synthesized in Example 18 was prepared and evaluated for ability to induce CTLs in vivo in an HLA-A*02:01 transgenic mouse.

Specifically, the compound of formula (4) was dissolved in dimethyl sulfoxide (DMSO) at a concentration of 66.67 mg/ml. The solution was diluted with water for injection to a concentration of 5 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (133.33 mg/ml) and the peptide of SEQ ID NO: 46 (91.67 mg/ml) in DMSO was prepared, diluted with water for injection to concentrations of the compound of formula (4) of 5 mg/ml and the peptide of SEQ ID NO: 46 of 3.4 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 170 μg of the peptide of SEQ ID NO: 46 per site. The cocktail vaccine was prepared to comprise the compound of formula (4) and the peptide of SEQ ID NO: 46 in equimolar amounts.

Figure 18:
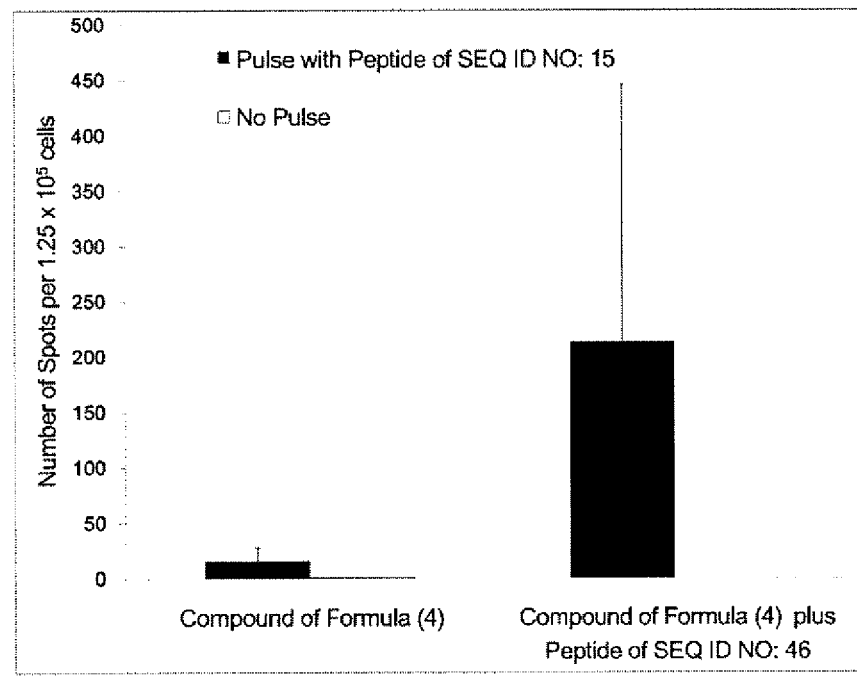
FIG. 18 shows in vivo CTL induction in an HLA-A*02:01 transgenic mouse by a cocktail vaccine comprising the compound of formula (4) synthesized in Reference Example 7 and the peptide of SEQ ID NO: 46 in an IFNγ ELISOPOT assay of Experimental Example 17.

FIG. 18 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 46 in addition to the compound of formula (4).

The cocktail vaccine comprising the peptide of SEQ ID NO: 46 in addition to the compound of formula (4) was highly effective in CTL induction as confirmed with the increase in the number of CTLs induced in the mice treated with the cocktail vaccine compared with the vaccine comprising the compound of formula (4).

Experimental Example 18

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 48 synthesized in Example 20 was prepared and evaluated for ability to induce CTLs in vivo in an HLA-A*02:01 transgenic mouse.

Specifically, the compound of formula (4) was dissolved in dimethyl sulfoxide (DMSO) at a concentration of 66.67 mg/ml. The solution was diluted with water for injection to a concentration of 5 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (133.33 mg/ml) and the peptide of SEQ ID NO: 48 (133.33 mg/ml) in DMSO was prepared, diluted with water for injection to concentrations of the compound of formula (4) of 5 mg/ml and the peptide of SEQ ID NO: 48 of 5.0 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 250 μg of the peptide of SEQ ID NO: 48 per site. The cocktail vaccine was prepared to comprise the compound of formula (4) and the peptide of SEQ ID NO: 48 in equimolar amounts.

Figure 19:
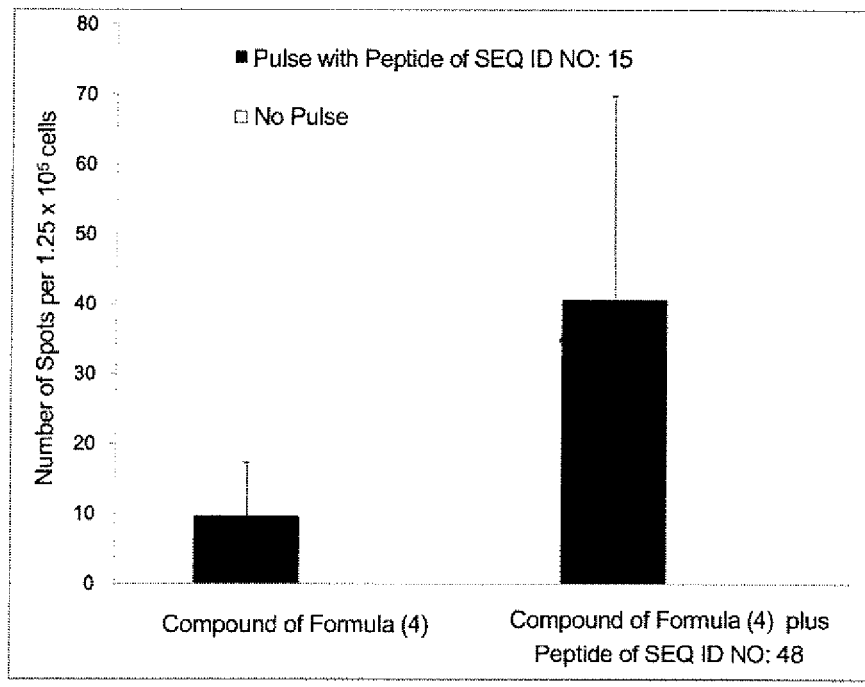
FIG. 19 shows in vivo CTL induction in an HLA-A*02:01 transgenic mouse by a cocktail vaccine comprising the compound of formula (4) synthesized in Reference Example 7 and the peptide of SEQ ID NO: 48 in an IFNγ ELISOPOT assay of Experimental Example 18.

FIG. 19 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 48 in addition to the compound of formula (4).

The cocktail vaccine comprising the peptide of SEQ ID NO: 48 in addition to the compound of formula (4) was highly effective in CTL induction as confirmed with the increase in the number of CTLs induced in the mice treated with the cocktail vaccine compared with the vaccine comprising the compound of formula (4).

Experimental Example 19

In Vivo CTL Induction in HLA-A*02:01 Transgenic Mouse

In accordance with the procedure as described in Experimental Example 1, a cocktail vaccine comprising the compound of formula (4) synthesized in Reference Example 7 and the peptide of SEQ ID NO: 49 synthesized in Example 21 was prepared and evaluated for ability to induce CTLs in vivo in an HLA-A*02:01 transgenic mouse.

Specifically, the compound of formula (4) was dissolved in dimethyl sulfoxide (DMSO) at a concentration of 66.67 mg/ml. The solution was diluted with water for injection to a concentration of 5 mg/ml, and then converted to an emulsion by addition of an equal volume of Montanide ISA 51 VG. The emulsion was injected to mice intradermally at two sites in the tail base area in an amount for administering 250 μg of the compound of formula (4) per site. On the other hand, a solution of the compound of formula (4) (133.33 mg/ml) and the peptide of SEQ ID NO: 49 (145.83 mg/ml) in DMSO was prepared, diluted with water for injection to concentrations of the compound of formula (4) of 5 mg/ml and the peptide of SEQ ID NO: 49 of 5.5 mg/ml, and then converted into an emulsion by the addition of an equal volume of Montanide ISA 51 VG. The cocktail vaccine emulsion was injected to mice intradermally at two sites in the tail base area in an amount for administering 250 μg of the compound of formula (4) per site and 270 μg of the peptide of SEQ ID NO: 49 per site. The cocktail vaccine was prepared to comprise the compound of formula (4) and the peptide of SEQ ID NO: 49 in equimolar amounts.

Figure 20:
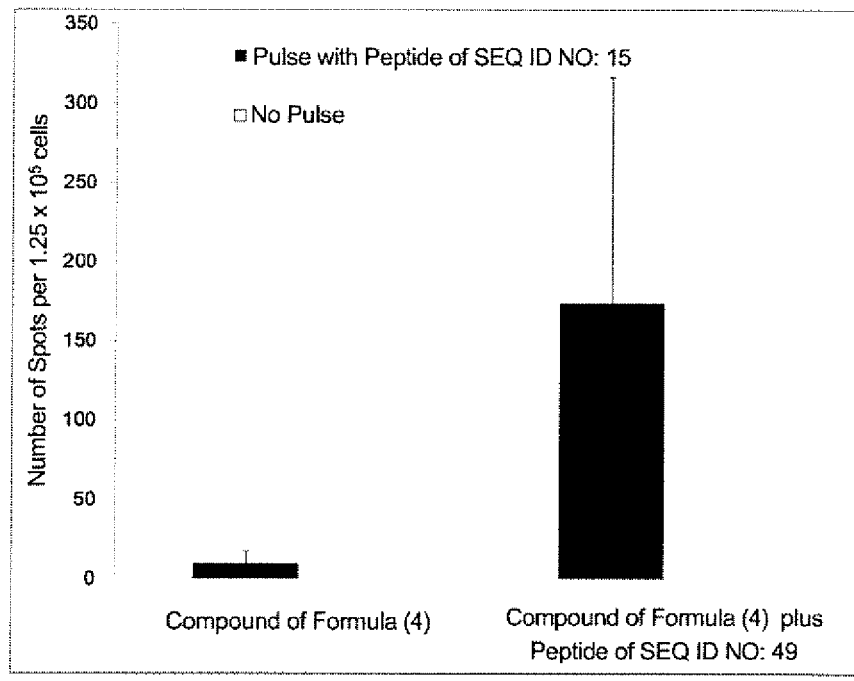
FIG. 20 shows in vivo CTL induction in an HLA-A*02:01 transgenic mouse by a cocktail vaccine comprising the compound of formula (4) synthesized in Reference Example 7 and the peptide of SEQ ID NO: 49 in an IFNγ ELISOPOT assay of Experimental Example 19.

FIG. 20 shows results from the IFNγ ELISPOT assay using the HLA-A*02:01 transgenic mouse. The results show that the compound of formula (4) induced CTLs responsive to the peptide of SEQ ID NO: 15 in the HLA-A*02:01 transgenic mouse, and that the CTL induction by the compound of formula (4) was enhanced by the cocktail vaccine comprising the peptide of SEQ ID NO: 49 in addition to the compound of formula (4).

The cocktail vaccine comprising the peptide of SEQ ID NO: 49 in addition to the compound of formula (4) was highly effective in CTL induction as confirmed with the increase in the number of CTLs induced in the mice treated with the cocktail vaccine compared with the vaccine comprising the compound of formula (4).

INDUSTRIAL APPLICABILITY

The present invention provides a cancer vaccine or a composition for cancer immunotherapy, which induces CTLs efficiently. Therefore, the present invention can find applications in the medical field, for example in development or production of compositions for treatment or prevention of a cancer.

Sequence Listing Free Text
SEQ ID NO: 2: Peptide
SEQ ID NO: 3: Peptide
SEQ ID NO: 4: Peptide
SEQ ID NO: 5: Peptide
SEQ ID NO: 6: Peptide
SEQ ID NO: 7: Peptide
SEQ ID NO: 8: Peptide
SEQ ID NO: 9: Peptide
SEQ ID NO: 10: Peptide
SEQ ID NO: 11: Peptide
SEQ ID NO: 12: Peptide
SEQ ID NO: 13: Peptide
SEQ ID NO: 14: Peptide
SEQ ID NO: 15: Peptide
SEQ ID NO: 16: Peptide
SEQ ID NO: 17: Peptide
SEQ ID NO: 18: Peptide
SEQ ID NO: 19: Peptide
SEQ ID NO: 20: Peptide
SEQ ID NO: 21: Peptide
SEQ ID NO: 22: Peptide
SEQ ID NO: 23: Peptide
SEQ ID NO: 24: Peptide
SEQ ID NO: 25: Peptide
SEQ ID NO: 26: Peptide
SEQ ID NO: 27: Peptide
SEQ ID NO: 28: Peptide
SEQ ID NO: 29: Peptide
SEQ ID NO: 30: Peptide
SEQ ID NO: 31: Peptide
SEQ ID NO: 32: Peptide
SEQ ID NO: 33: Peptide
SEQ ID NO: 34: Peptide
SEQ ID NO: 35: Peptide
SEQ ID NO: 36: Peptide
SEQ ID NO: 37: Peptide
SEQ ID NO: 38: Peptide
SEQ ID NO: 39: Peptide
SEQ ID NO: 40: Peptide
SEQ ID NO: 41: Peptide
SEQ ID NO: 42: Peptide
SEQ ID NO: 43: Peptide
SEQ ID NO: 44: Peptide
SEQ ID NO: 45: Peptide
SEQ ID NO: 46: Peptide
SEQ ID NO: 47: Peptide SEQ ID NO: 48: Peptide
SEQ ID NO: 49: Peptide
SEQ ID NO: 50: Peptide
SEQ ID NO: 51: Peptide
SEQ ID NO: 52: Peptide
SEQ ID NO: 53: Peptide
SEQ ID NO: 54: Peptide
SEQ ID NO: 55: Peptide
SEQ ID NO: 56: Peptide
SEQ ID NO: 57: Peptide
SEQ ID NO: 58: Peptide
SEQ ID NO: 59: Peptide
SEQ ID NO: 60: Peptide
SEQ ID NO: 61: Peptide
SEQ ID NO: 62: Peptide
SEQ ID NO: 63: Peptide
SEQ ID NO: 64: Peptide
SEQ ID NO: 65: Peptide
SEQ ID NO: 66: Peptide
SEQ ID NO: 67: Peptide
SEQ ID NO: 68: Peptide
SEQ ID NO: 69: Amino acid sequence corresponding to amino acids 311-365 in SEQ ID NO: 1

The invention claimed is:

1. A composition or kit comprising at least one compound selected from the compound of formula (3):

$$\begin{array}{c} \text{CRMFPNAPYL (SEQ ID NO: 35),} \\ | \\ \text{CMTWNQMNL (SEQ ID NO: 16)} \end{array} \quad (3)$$

or a pharmaceutically acceptable salt thereof, or a compound of formula (4):

$$\begin{array}{c} \text{CRMFPNAPYL (SEQ ID NO: 35)} \\ | \\ \text{CYTWNQMNL (SEQ ID NO: 17)} \end{array} \quad (4)$$

or a pharmaceutically acceptable salt thereof,
wherein C—C are linked together by disulfide bond,
and
cancer antigen peptide D or a pharmaceutically acceptable salt thereof, wherein the cancer antigen peptide D is a peptide which induces WT1-specific helper T cells by binding to an MHC class II molecule and consisting of the amino acid sequence selected from:

AYPGCNKRYFKLSHL, (SEQ ID NO: 2)

YPGCNKRYFKLSHLQ, (SEQ ID NO: 3)

NKRYFKLSHLQMHSRK, (SEQ ID NO: 8)

KRYFKLSHLQMHSRK, (SEQ ID NO: 9)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)

KLSHLQMHSRKHTGE, (SEQ ID NO: 14)

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

AYPGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

-continued

KLSHLQMHSRKH, (SEQ ID NO: 50)

AYPGCNKRYFKLSHLQMHSR, (SEQ ID NO: 52)

AYPGCNKRYFKLSHLQMHS, (SEQ ID NO: 53)

AYPGCNKRYFKLSHLQM, (SEQ ID NO: 54)

AYPGCNKRYFKLSHLQ, (SEQ ID NO: 55)

YFKLSHLQMHSRKHTGE, (SEQ ID NO: 56)

RYFKLSHLQMHSRKHTG, (SEQ ID NO: 57)

RYFKLSHLQMHSR, (SEQ ID NO: 58)

RYFKLSHLQMHS, (SEQ ID NO: 59)

RYFKLSHLQM, (SEQ ID NO: 60)

YPGCNKRYFKLSHL, (SEQ ID NO: 61)

PGCNKRYFKLSHL, (SEQ ID NO: 62)

CNKRYFKLSHL, (SEQ ID NO: 63)

NKRYFKLSHL, (SEQ ID NO: 64)

KLSHLQMHSRKHTG, (SEQ ID NO: 65)

KLSHLQMHSRKHT, (SEQ ID NO: 66)
and

KLSHLQMHSRK, (SEQ ID NO: 67)

or a peptide consisting of the amino acid sequence that differs from the amino acid sequence of the cancer antigen peptide D by alteration of one amino acid residue, provided that the cancer antigen peptide D is not SEQ ID NO:6, SEQ ID NO: 7, SEQ ID NO: 10, SEQ ID NO: 38, or SEQ ID NO:51.

2. The composition or kit according to claim 1, wherein the compound or a pharmaceutically acceptable salt thereof is the compound of formula (3):

CRMFPNAPYL (SEQ ID NO: 35),
|
CMTWNQMNL (SEQ ID NO: 16)
(3)

wherein C—C shown in the formula means that the C residues are linked together by a disulfide bond, or a pharmaceutically acceptable salt thereof.

3. The composition or kit according to claim 1, wherein the compound or a pharmaceutically acceptable salt thereof is the compound of formula (4):

CRMFPNAPYL (SEQ ID NO: 35)
|
CYTWNQMNL (SEQ ID NO: 17)
(4)

wherein C—C shown in the formula means that the C residues are linked together by a disulfide bond, or a pharmaceutically acceptable salt thereof.

4. The composition or kit according to claim 1, wherein the cancer antigen peptide D is a peptide consisting of the amino acid sequence selected from:

AYPGCNKRYFKLSHL, (SEQ ID NO: 2)

YPGCNKRYFKLSHLQ, (SEQ ID NO: 3)

NKRYFKLSHLQMHSRK, (SEQ ID NO: 8)

KRYFKLSHLQMHSRK, (SEQ ID NO: 9)

RYFKLSHLQMHSRKH, (SEQ ID NO: 11)

YFKLSHLQMHSRKHT, (SEQ ID NO: 12)

FKLSHLQMHSRKHTG, (SEQ ID NO: 13)
and

KLSHLQMHSRKHTGE. (SEQ ID NO: 14)

5. The composition or kit according to claim 1, wherein the cancer antigen peptide D is a peptide consisting of the amino acid sequence selected from:

RYFKLSHLQMHSRK, (SEQ ID NO: 39)

YFKLSHLQMHSRK, (SEQ ID NO: 40)

FKLSHLQMHSRK, (SEQ ID NO: 41)

KLSHLQMHSRK, (SEQ ID NO: 42)

AYPGCNKRYFKLSHLQMH, (SEQ ID NO: 43)

AYPGCNKRYFKLSHLQMHSRK, (SEQ ID NO: 44)

RYFKLSHLQMH, (SEQ ID NO: 45)

GCNKRYFKLSHL, (SEQ ID NO: 46)

FKLSHLQMHSRKHTGE, (SEQ ID NO: 47)

RYFKLSHLQMHSRKHT, (SEQ ID NO: 48)

RYFKLSHLQMHSRKHTGE, (SEQ ID NO: 49)

(SEQ ID NO: 50)

```
                                                    (SEQ ID NO: 52)
KLSHLQMHSRKH, (SEQ ID NO: 53)
AYPGCNKRYFKLSHLQMHSR, (SEQ ID NO: 54)
AYPGCNKRYFKLSHLQMHS, (SEQ ID NO: 55)
AYPGCNKRYFKLSHLQM, (SEQ ID NO: 56)
AYPGCNKRYFKLSHLQ, (SEQ ID NO: 57)
YFKLSHLQMHSRKHTGE, (SEQ ID NO: 58)
RYFKLSHLQMHSRKHTG, (SEQ ID NO: 59)
RYFKLSHLQMHSR, (SEQ ID NO: 60)
RYFKLSHLQMHS, (SEQ ID NO: 61)
RYFKLSHLQM, (SEQ ID NO: 62)
YPGCNKRYFKLSHL, (SEQ ID NO: 63)
PGCNKRYFKLSHL, (SEQ ID NO: 64)
CNKRYFKLSHL, (SEQ ID NO: 65)
NKRYFKLSHL, (SEQ ID NO: 66)
KLSHLQMHSRKHTG, (SEQ ID NO: 67)
KLSHLQMHSRKHT,
and

KLSHLQMHSRK.
```

6. The composition or kit according to claim 1, wherein the compound or a pharmaceutically acceptable salt thereof is the compound of formula (4):

$$\text{CRMFPNAPYL (SEQ ID NO: 35),} \atop | \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: AYPGCNKRYFKLSHL (SEQ ID NO: 2) or a pharmaceutically acceptable salt thereof.

7. The composition or kit according to claim 1, wherein the compound or a pharmaceutically acceptable salt thereof is the compound of formula (4):

$$\text{CRMFPNAPYL (SEQ ID NO: 35),} \atop | \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: YPGCNKRYFKLSHLQ (SEQ ID NO: 3) or a pharmaceutically acceptable salt thereof.

8. The composition or kit according to claim 1, wherein the compound or a pharmaceutically acceptable salt thereof is the compound of formula (4):

$$\text{CRMFPNAPYL (SEQ ID NO: 35),} \atop | \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: NKRYFKLSHLQMHSRK (SEQ ID NO: 8) or a pharmaceutically acceptable salt thereof.

9. The composition or kit according to claim 1, wherein the compound or a pharmaceutically acceptable salt thereof is the compound of formula (4):

$$\text{CRMFPNAPYL (SEQ ID NO: 35),} \atop | \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: KRYFKLSHLQMHSRK (SEQ ID NO: 9) or a pharmaceutically acceptable salt thereof.

10. The composition or kit according to claim 1, wherein the compound or a pharmaceutically acceptable salt thereof is the compound of formula (4):

$$\text{CRMFPNAPYL (SEQ ID NO: 35),} \atop | \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKH (SEQ ID NO: 11) or a pharmaceutically acceptable salt thereof.

11. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: YFKLSHLQMHSRKHT (SEQ ID NO: 12) or a pharmaceutically acceptable salt thereof.

12. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: FKLSHLQMHSRKHTG (SEQ ID NO: 13) or a pharmaceutically acceptable salt thereof.

13. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: KLSHLQMHSRKHTGE (SEQ ID NO: 14) or a pharmaceutically acceptable salt thereof.

14. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: RYFKLSHLQMHSRK (SEQ ID NO: 39) or a pharmaceutically acceptable salt thereof.

15. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: AYPGCNKRYFKLSHLQMH (SEQ ID NO: 43) or a pharmaceutically acceptable salt thereof.

16. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: AYPGCNKRYFKLSHLQMHSRK (SEQ ID NO: 44) or a pharmaceutically acceptable salt thereof.

17. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: RYFKLSHLQMH (SEQ ID NO: 45) or a pharmaceutically acceptable salt thereof.

18. The composition or kit according to claim 1, wherein the compound or a pharmaceutically acceptable salt thereof is the compound of formula (4):

$$\begin{array}{l} \text{CRMFPNAPYL (SEQ ID NO: 35),} \\ | \\ \text{CYTWNQMNL (SEQ ID NO: 17)} \end{array} \quad (4)$$

wherein C—C shown in the formula means that the C residues are linked together by a disulfide bond,
or a pharmaceutically acceptable salt thereof, and the cancer antigen peptide D or a pharmaceutically acceptable salt thereof is a peptide consisting of the amino acid sequence: GCNKRYFKLSHL (SEQ ID NO: 46) or a pharmaceutically acceptable salt thereof.

19. The composition or kit according to claim 1, wherein the compound or a pharmaceutically acceptable salt thereof is the compound of formula (4):

$$\text{CRMFPNAPYL (SEQ ID NO: 35),} \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKHT (SEQ ID NO: 48) or a pharmaceutically acceptable salt thereof.

20. The composition or kit according to claim 1, wherein the compound or a pharmaceutically acceptable salt thereof is the compound of formula (4):

$$\text{CRMFPNAPYL (SEQ ID NO: 35),} \atop \text{CYTWNQMNL (SEQ ID NO: 17)} \quad (4)$$

wherein C—C shown in the formula means that the C residues are linked together by a disulfide bond, or a pharmaceutically acceptable salt thereof, and the cancer antigen peptide D or a pharmaceutically acceptable salt thereof is a peptide consisting of the amino acid sequence: RYFKLSHLQMHSRKHTGE (SEQ ID NO: 49) or a pharmaceutically acceptable salt thereof.

21. The composition or kit according to claim 1, wherein the compound or a pharmaceutically acceptable salt thereof and the cancer antigen peptide D or a pharmaceutically acceptable salt thereof are formulated in separate compositions.

22. The composition or kit according to claim 1, wherein the compound or a pharmaceutically acceptable salt thereof and the cancer antigen peptide D or a pharmaceutically acceptable salt thereof are incorporated in a single composition.

23. The composition or kit according to claim 1, wherein the cancer antigen peptide D is a peptide which induces WT1-specific helper T cells by binding to an MHC class II molecule selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602, and DRB5*0102.

24. The composition or kit according to claim 1, wherein the cancer antigen peptide D is a peptide which induces WT1-specific helper T cells by binding to an MHC class II molecule selected from the group consisting of DRB1*0101, DRB1*0405, DRB1*1502, DPB1*0201, DPB1*0202 and DQB1*0601.

25. A pharmaceutical composition comprising the composition according to claim 1, and a pharmaceutically acceptable carrier.

26. The composition or kit according to claim 1, wherein the composition or kit is the composition.

27. The composition or kit according to claim 1, wherein the composition or kit is the kit.

* * * * *